United States Patent
Bean et al.

(10) Patent No.: US 11,021,443 B2
(45) Date of Patent: Jun. 1, 2021

(54) CHARGED ION CHANNEL BLOCKERS AND METHODS FOR USE

(71) Applicants: President and Fellows of Harvard College, Cambridge, MA (US); Children's Medical Center Corporation, Boston, MA (US)

(72) Inventors: Bruce P. Bean, Waban, MA (US); Clifford J. Woolf, Newton, MA (US); Jinbo Lee, Andover, MA (US); Sooyeon Jo, Auburndale, MA (US); David Roberson, Cambridge, MA (US); Sebastien Talbot, Everett, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/749,885

(22) PCT Filed: Aug. 3, 2016

(86) PCT No.: PCT/US2016/045354
§ 371 (c)(1),
(2) Date: Feb. 2, 2018

(87) PCT Pub. No.: WO2017/024037
PCT Pub. Date: Feb. 9, 2017

(65) Prior Publication Data
US 2018/0237392 A1    Aug. 23, 2018

Related U.S. Application Data

(60) Provisional application No. 62/200,205, filed on Aug. 3, 2015.

(51) Int. Cl.
  *A61K 31/452* (2006.01)
  *C07D 295/037* (2006.01)
  (Continued)

(52) U.S. Cl.
  CPC .......... *C07D 211/34* (2013.01); *A61K 31/452* (2013.01); *A61K 45/06* (2013.01);
  (Continued)

(58) Field of Classification Search
  CPC . C07D 295/037; C07D 211/14; A61K 31/452
  (Continued)

(56) References Cited

U.S. PATENT DOCUMENTS

| | | |
|---|---|---|
| 812,554 A | 2/1906 | Einhorn |
| 1,889,645 A | 11/1932 | Otto |

(Continued)

FOREIGN PATENT DOCUMENTS

| | | |
|---|---|---|
| CA | 982148 | 1/1976 |
| CA | 2717042 A1 | 9/2009 |

(Continued)

OTHER PUBLICATIONS

Anderson, Chem & Biol (2003), vol. 10, pp. 787-797. (Year: 2003).*

(Continued)

*Primary Examiner* — Craig D Ricci
*Assistant Examiner* — Janet L Coppins
(74) *Attorney, Agent, or Firm* — Wolf, Greenfield & Sacks, P.C.

(57) ABSTRACT

The invention provides compounds, compositions, methods, and kits for the treatment of pain, itch, and neurogenic inflammation.

18 Claims, 10 Drawing Sheets

(51) Int. Cl.
  *C07D 211/34* (2006.01)
  *A61K 45/06* (2006.01)
  *C07C 237/04* (2006.01)
  *C07D 207/08* (2006.01)
  *C07D 211/14* (2006.01)
  *C07D 207/16* (2006.01)

(52) U.S. Cl.
  CPC .......... *C07C 237/04* (2013.01); *C07D 207/08* (2013.01); *C07D 211/14* (2013.01); *C07D 295/037* (2013.01); *C07D 207/16* (2013.01)

(58) Field of Classification Search
  USPC ....................................................... 514/330
  See application file for complete search history.

(56) References Cited

U.S. PATENT DOCUMENTS

| | | | |
|---|---|---|---|
| 2,441,498 | A | 5/1948 | Loefgren et al. |
| 2,689,248 | A | 9/1954 | Clinton et al. |
| 2,799,679 | A | 7/1957 | Thuresson et al. |
| 2,955,111 | A | 10/1960 | Thuresson et al. |
| 3,160,662 | A | 12/1964 | Magnus et al. |
| 3,177,252 | A | 4/1965 | Leon |
| 3,519,631 | A | 7/1970 | Jerchel et al. |
| 3,773,939 | A | 11/1973 | Janssen |
| 3,812,147 | A | 5/1974 | Adams et al. |
| 3,900,481 | A | 8/1975 | Banitt et al. |
| 3,931,195 | A | 1/1976 | Dykstra et al. |
| 4,069,309 | A | 1/1978 | Ciaudelli et al. |
| 4,070,347 | A | 1/1978 | Schmitt |
| 4,141,718 | A | 2/1979 | Martin |
| 4,233,055 | A | 11/1980 | Martin et al. |
| 4,293,539 | A | 10/1981 | Ludwig et al. |
| 4,757,128 | A | 7/1988 | Domb et al. |
| 4,877,805 | A | 10/1989 | Kligman |
| 4,975,282 | A | 12/1990 | Cullis et al. |
| 4,980,378 | A | 12/1990 | Wong et al. |
| 4,994,213 | A | 2/1991 | Aitcheson et al. |
| 5,000,958 | A | 3/1991 | Fountain et al. |
| 5,023,087 | A | 6/1991 | Yau-Young |
| 5,032,582 | A | 7/1991 | Abra |
| 5,049,388 | A | 9/1991 | Knight et al. |
| 5,082,866 | A | 1/1992 | Wong et al. |
| 5,169,637 | A | 12/1992 | Lenk et al. |
| 5,176,907 | A | 1/1993 | Leong |
| 5,194,266 | A | 3/1993 | Abra et al. |
| 5,194,581 | A | 3/1993 | Leong |
| 5,356,633 | A | 10/1994 | Woodle et al. |
| 5,409,704 | A | 4/1995 | Bally et al. |
| 5,480,971 | A | 1/1996 | Houghten et al. |
| 5,552,155 | A | 6/1996 | Jones |
| 5,591,317 | A | 1/1997 | Pitts, Jr. |
| 5,688,525 | A | 11/1997 | Adler-Moore et al. |
| 5,747,470 | A | 5/1998 | Becherer et al. |
| 5,783,683 | A | 7/1998 | Morrison |
| 5,874,104 | A | 2/1999 | Adler-Moore et al. |
| 5,883,228 | A | 3/1999 | Darnell, Jr. et al. |
| 5,952,451 | A | 9/1999 | Zhao |
| 6,008,318 | A | 12/1999 | Zhao |
| 6,051,576 | A | 4/2000 | Ashton et al. |
| 6,083,996 | A | 7/2000 | Buyuktimkin et al. |
| 6,103,255 | A | 8/2000 | Levene |
| 6,118,020 | A | 9/2000 | Buyuktimkin et al. |
| 6,153,212 | A | 11/2000 | Mao et al. |
| 6,355,637 | B1 | 3/2002 | Axt et al. |
| 6,362,197 | B1 | 3/2002 | Page et al. |
| 6,413,961 | B1 | 7/2002 | Demopulos et al. |
| 6,432,937 | B1 | 8/2002 | Hallgren |
| 6,623,040 | B1 | 9/2003 | Foley et al. |
| 6,709,406 | B2 | 3/2004 | Laserow |
| 6,766,319 | B1 | 7/2004 | Might |
| 6,825,190 | B2 | 11/2004 | Moon et al. |
| 6,884,782 | B2 | 4/2005 | Huang et al. |
| 7,166,590 | B2 | 1/2007 | Seko et al. |
| 7,429,673 | B2 | 9/2008 | Morazzoni et al. |
| 7,446,226 | B2 | 11/2008 | Helsing et al. |
| 7,705,004 | B2 | 4/2010 | Song et al. |
| 8,138,339 | B2 | 3/2012 | Bauer et al. |
| 8,143,412 | B2 | 3/2012 | Priebe et al. |
| 8,258,144 | B2 | 9/2012 | Song et al. |
| 8,822,537 | B2 | 9/2014 | Buyuktimkin et al. |
| 9,603,817 | B2 | 3/2017 | Bean et al. |
| 10,179,116 | B2 | 1/2019 | Bean et al. |
| 10,729,664 | B2 | 8/2020 | Woolf et al. |
| 2003/0105126 | A1 | 6/2003 | Demopulos et al. |
| 2003/0152637 | A1 | 8/2003 | Chasin et al. |
| 2003/0166629 | A1 | 9/2003 | Choi et al. |
| 2004/0146590 | A1 | 7/2004 | Iadarola et al. |
| 2004/0220187 | A1 | 11/2004 | Stephenson et al. |
| 2004/0266870 | A1* | 12/2004 | Allegretti ............ C07C 233/40 514/554 |
| 2005/0009016 | A1 | 1/2005 | Moskowitz et al. |
| 2005/0025765 | A1 | 2/2005 | DiMauro et al. |
| 2005/0090557 | A1 | 4/2005 | Muhammad et al. |
| 2005/0142596 | A1 | 6/2005 | Krolewski et al. |
| 2005/0152957 | A1 | 7/2005 | Cleary et al. |
| 2005/0233398 | A1* | 10/2005 | Chu .................... C07C 275/40 435/7.92 |
| 2005/0277680 | A1 | 12/2005 | Priebe et al. |
| 2006/0036098 | A1 | 2/2006 | Kim et al. |
| 2006/0062739 | A1 | 3/2006 | Hofmann et al. |
| 2006/0100272 | A1 | 5/2006 | Maniar |
| 2006/0106020 | A1 | 5/2006 | Rodgers et al. |
| 2006/0134008 | A1 | 6/2006 | Deaver |
| 2006/0183906 | A1 | 8/2006 | Rodgers et al. |
| 2007/0135461 | A1 | 6/2007 | Rodgers et al. |
| 2007/0149469 | A1 | 6/2007 | Korherr |
| 2007/0149506 | A1 | 6/2007 | Arvanitis et al. |
| 2008/0188500 | A1 | 8/2008 | Arvanitis et al. |
| 2008/0312212 | A1 | 12/2008 | Collingwood et al. |
| 2009/0054485 | A1 | 2/2009 | Gleich et al. |
| 2009/0060898 | A1 | 3/2009 | Kandimalla et al. |
| 2009/0162333 | A1 | 6/2009 | Pays et al. |
| 2009/0270478 | A1 | 10/2009 | Feddia et al. |
| 2010/0098685 | A1 | 4/2010 | Zhu et al. |
| 2010/0099772 | A1 | 4/2010 | Bean et al. |
| 2010/0113416 | A1 | 5/2010 | Friedman et al. |
| 2010/0120781 | A1 | 5/2010 | Neamati |
| 2011/0086818 | A1 | 4/2011 | Bean et al. |
| 2012/0022142 | A1 | 1/2012 | Jadhav et al. |
| 2012/0129867 | A1 | 5/2012 | Bauer et al. |
| 2012/0172429 | A1 | 7/2012 | Woolf et al. |
| 2012/0195902 | A1 | 8/2012 | Friedman et al. |
| 2015/0087552 | A1 | 3/2015 | Jensen et al. |
| 2015/0087714 | A1 | 3/2015 | Bean et al. |
| 2017/0319517 | A1 | 11/2017 | Bean et al. |
| 2018/0237392 | A1 | 8/2018 | Bean et al. |
| 2018/0303945 | A1 | 10/2018 | Adams et al. |
| 2019/0216747 | A1 | 7/2019 | Woolf et al. |
| 2020/0231545 | A1 | 7/2020 | Bean et al. |

FOREIGN PATENT DOCUMENTS

| | | |
|---|---|---|
| CN | 101156851 A | 4/2008 |
| CN | 101347427 A | 1/2009 |
| DE | 2 162 744 A1 | 7/1972 |
| DE | 2 235 745 A1 | 2/1973 |
| DE | 2657728 A1 | 7/1977 |
| DE | 2915250 A1 | 10/1980 |
| DE | 150423 | 9/1981 |
| DE | 151036 | 9/1981 |
| DE | 100 39 449 A1 | 7/2003 |
| EP | 0586106 A1 | 3/1994 |
| GB | 866604 A | 4/1961 |
| JP | S52-78840 A | 7/1977 |
| JP | 2000-143635 A | 5/2000 |
| JP | 2001-513106 A | 8/2001 |
| JP | 2002-517438 | 6/2002 |
| JP | 2003-516966 A | 5/2003 |
| JP | 2003-516982 | 5/2003 |
| JP | 2006-522832 A | 10/2006 |
| JP | 2008-514648 A | 5/2008 |
| JP | 2009-520700 A | 5/2009 |

(56) References Cited

FOREIGN PATENT DOCUMENTS

| | | |
|---|---|---|
| JP | 2011-513484 A | 4/2011 |
| JP | 6205133 B2 | 9/2017 |
| WO | WO 1985/00599 A1 | 2/1985 |
| WO | WO 1996/40061 A1 | 12/1996 |
| WO | WO-98/24428 A1 | 6/1998 |
| WO | WO-98/37896 A1 | 9/1998 |
| WO | WO-99/11252 A2 | 3/1999 |
| WO | WO-99/63985 A1 | 12/1999 |
| WO | WO-01/44192 A1 | 6/2001 |
| WO | WO-01/44218 A1 | 6/2001 |
| WO | WO-01/45678 A2 | 6/2001 |
| WO | WO-2004/012757 A2 | 2/2004 |
| WO | WO 2005/014849 A2 | 7/2004 |
| WO | WO-2004/110423 A1 | 12/2004 |
| WO | WO-2005/089206 A2 | 9/2005 |
| WO | WO-2005/117981 A1 | 12/2005 |
| WO | WO-2006/010587 A1 | 2/2006 |
| WO | WO-2006/065722 A2 | 6/2006 |
| WO | WO 2006/133588 A1 | 12/2006 |
| WO | WO-2007/071055 A1 | 6/2007 |
| WO | WO-2008/063603 A2 | 5/2008 |
| WO | WO 2008/063603 A3 | 5/2008 |
| WO | WO-2009/114139 A2 | 9/2009 |
| WO | WO-2010/017996 A1 | 2/2010 |
| WO | WO 2010/078300 A1 | 7/2010 |
| WO | WO 2011/006073 A1 | 1/2011 |
| WO | WO- 2011/006073 A1 | 1/2011 |
| WO | WO-2011/133474 A2 | 10/2011 |
| WO | WO-2012/030912 A1 | 3/2012 |
| WO | WO-2012/162394 A2 | 11/2012 |
| WO | 2014/025761 A1 | 2/2014 |
| WO | WO 2017/024037 A1 | 2/2017 |
| WO | WO 2018/214980 A1 | 11/2018 |

OTHER PUBLICATIONS

Lukacs et al, Scientific Reports (2018), vol. 8, pp. 1-11. (Year: 2018).*

Ross, S.B. and Ackerman, S.B., J. of Pharm. & Exp. Therapeutics (1972), vol. 182 (2), pp. 351-361. (Year: 1972).*

Thiel, Nature Biotech (2004), vol. 22 (5), pp. 513-519. (Year: 2004).*

Nanya, Nihon Yakurigaku Zassh (1963), vol. 59, pp. 113-122. (Year: 1963).*

Senda etal, Pharmaceutica Acta Helvetiae (1963), vol. 38, pp. 470-473. (Year: 1963).*

International Search Report and Written Opinion for International Application No. PCT/US16/45354, dated Dec. 7, 2016 (14 pages).

AU 208-236902, Jul. 11, 2019, Examination Report.

CA 2767646, Nov. 1, 2017, Canadian Office Action.

CN 201410034926.2, Jul. 23, 2015, Chinese Office Action.

EP 10797919.7, Oct. 29, 2012, Extended European Search Report.

EP 18211462, Apr. 23, 2019, Extended European Search Report.

JP 2017-086446, Apr. 16, 2019, Japanese Office Action.

PCT/US2007/024174, May 20, 2009, Written Opinion.

PCT/US16/45354, Dec. 7, 2016, International Search Report and Written Opinion.

PCT/US2011/32924, Apr. 9, 2012, Written Opinion.

International Preliminary Report on Patentability and Written Opinion for International Application No. PCT/US2013/070908, dated Jun. 2, 2015 (8 pages).

Schwarz et al., "Lumbar intrathecal administration of the quaternary lidocaine derivative, QX-314, produces neurotoxicity in mice," Can. J. Anaesth. 55(1):473931 (Abstract Only) (2008).

Taylor et al., "Persistent cardiovascular and behavioral nociceptive responses to subcutaneous formalin require peripheral nerve input," J Neurosci. 15(11):7575-7584 (1995).

Rathmell et al. "Assessment of Differential Sensory Blockade Using QX-314 and Capsaicin in Large Animals," <http://www.abstractsonline.com/submit/SubmitPrinterFriendlyVersion.asp?ControlKey% . . . > Presentation No. PW 233. 12th World Congress on Pain Itinerary Planner, Glasgow, Scotland: International Association for the Study of Pain, 2008. Retrieved Online Jan. 31, 2008 (2 pages).

Examiner's Report for Australian Patent Application No. 2010271269, dated Sep. 9, 2015 (4 pages).

Holmdahl G, et al. A substance P antagonist, [D-Pro2, D-Trp7,9]SP, inhibits inflammatory responses in the rabbit eye Science. Nov. 27, 1981;214(4524):1029-31.

Steinhoff et al., "Neurophysiological, Neuroimmunological, and Neuroendocrine Basis of Pruritus," J. Invest Dermatol. 126(8):1705-1718 (2006).

International Preliminary Report on Patentability for International Application No. PCT/US2007/024174 dated May 26, 2009 (20 pages).

Talbot et al., "Silencing Nociceptor Neurons Reduces Allergic Airway Inflammation," Neuron. 87(2):341-54 (2015) (15 pages).

Leffler et al., "The Vanilloid Receptor TRPV1 is Activated and Sensitized by Local Anesthetics in Rodent Sensory Neurons," J. Clin. Invest. 118:763-776 (2008).

Hunter et al. "The Contribution of Peripheral Sensory Neuronal Input towards The Maintenance of Neuropathic Pain" Soc Neurosci. 21:1411 (1995). (Abstract Only).

Clare et al., "Voltage-gated sodium channels as therapeutic targets," Drug Discovery Today. 5(11):506-520 (2000).

Gerner et al., "Capsaicin Combined with Local Anesthetics Preferentially Prolongs Sensory/Nociceptive Block in Rat Sciatic Nerve," Anesthesiology 109:872-878 (2008).

International Search Report of International Application No. PCT/US2010/41537, dated Oct. 18, 2010 (4 pages).

Jia et al., "TRPV1 receptor: a target for the treatment of pain, cough, airway disease and urinary incontinence," Drug News Perspect. 18(3):165-71 (2005). Abstract only.

Carr, "Neuroimmunology: Adding insult to allergy," Nat Rev Neurosci. 16(8):444 (2015).

Kalso et al., "Sodium channel blockers in neuropathic pain," Current Pharmaceutical Design. 11(23):3005-11 (2005). Abstract Only.

McGivern et al., "Voltage-Gated Calcium Channels as Targets for the Treatment of Chronic Pain," Curr. Drug Targets CNS Neurol. Disord. 3:457-478 (2004).

Triggle, "The pharmacology of ion channels: with particular reference to voltage-gated Ca2+ channels," Eur J Pharmacol. 375(1-3):311-25 (1999).

Dux et al., "Inhibition of the neurogenic inflammatory response by lidocaine in rat skin," Inflamm Res. 45(1):10-3 (1996).

Gerner et al., "Spinal Tonicaine: Potency and Differential Blockade of Sensory and Motor Functions," Anesthesiology 92:1350-1360 (2000).

Meyers et al., "Lighting up the Senses: FM1-43 Loading of Sensory Cells through Nonselective Ion Channels," J. Neurosci. 23:4054-4065 (2003).

Mizogami et al., "Local anesthetics adsorbed onto infusion balloon," Anesth Analg. 99(3):764-8 (2004).

Ferrarelli, "Allergic sensations fuel asthma," Sci Signal. 8(387):ec201 (2015).

European Patent Office Communication pertaining to European Patent Application No. 11007949.8-2112, dated Feb. 17, 2012 (11 pages).

Omana-Zapata et al., "QX-314 inhibits ectopic nerve activity associated with neuropathic pain," Brain Res. 771:228-237 (1997).

Appel et al., "Intensive blood-pressure control in hypertensive chronic kidney disease," N Engl J Med. 363(10): 918-29 (2010).

McCleskey, "Neuroscience: a local route to pain relief," Nature. 449(7162):545-6 (2007).

Wan et al., "Apolipoprotein L1, a novel Bcl-2 homology domain 3-only lipid-binding protein, induces autophagic cell death," J Biol Chem. 283(31): 21540-9 (2008).

Office Action for Australian Patent Application No. 2009223739, dated Aug. 9, 2013 (4 pages).

Office Action for Australian Patent Application No. 2007322033, dated Apr. 23, 2012 (3 pages).

"Target neurons to relieve asthma," Nature. 523:8-9 (2015).

Office Action for Canadian Patent Application No. 2,668,652, dated Sep. 18, 2013 (4 pages).

(56) References Cited

OTHER PUBLICATIONS

Breznan et al., "The lipid composition of high-density lipoprotein affects its re-absorption in the kidney by proximal tubule epithelial cells," Biochem J. 379(Pt 2):343-9 (2004).
D'Agati et al., "Focal segmental glomerulosclerosis," N Engl J Med. 365(25):2398-411 (2011).
Bentley et al., "Variation in APOL1 Contributes to Ancestry-Level Differences in HDLc-Kidney Function Association," Int J Nephrol. 748984 (2012) (10 pages).
Lundberg JM, et al. Vascular permeability changes and smooth muscle contraction in relation to capsaicin-sensitive substance P afferents in the guinea-pig. Acta Physiol Scand. Feb. 1984;120(2):217-27.
NCBI Blast for Accession No. NC_000022.10. Retrieved on Jun. 9, 2015 (2 pages).
Office Action for Chinese Patent Application No. 200780050131.9, dated Sep. 13, 2013 (7 pages).
Office Action for Canadian Patent Application No. 2,668,652, dated May 6, 2016 (4 pages).
Office Action for Chinese Patent Application No. 200780050131.9, dated Jun. 4, 2012 (10 pages).
NCBI Blast for Accession No. NM_003661.3. Retrieved on Jun. 9, 2015 (5 pages).
Bley, "Recent developments in transient receptor potential vanilloid receptor 1 agonist-based therapies," Expert Opin Investig Drugs. 13(11):1445-56 (2004).
NCBI Blast for Accession No. NM_001136540.1. Retrieved on Jun. 9, 2015 (5 pages).
NCBI Blast for Accession No. BC127186.1. Retrieved on Jun. 9, 2015 (3 pages).
Office Action for Chinese Patent Application No. 200980117485.X, dated Nov. 23, 2011 (10 pages).
Office Action for Chinese Patent Application No. 200980117485.X, dated Oct. 24, 2012 (24 pages).
Notice of Reasons for Rejection for Japanese Patent Application No. 2014-015120, dated Aug. 25, 2015 (5 pages).
Office Action for Chinese Patent Application No. 200980117485.X, dated Feb. 24, 2014 (9 pages).
NCBI Blast for Accession No. AAI43039.1. Retrieved on Jun. 9, 2015 (2 pages).
Office Action for Chinese Patent Application No. 200780050131.9, dated Feb. 23, 2011 (9 pages).
Kiberstis, "Letter and reviews from Science (1189125)," E-mail to Martin Pollak dated Mar. 16, 2010 (3 pages).
NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).
Li et al., "Distribution and effect of apoL-I genotype on plasma lipid and apolipoprotein levels in Chinese normalipidemic and endogenous hypertriglyceridemic subjects," Clin Chim Acta. 403(1-2):152-5 (2009).
Communication Pursuant to Article for 94(3) EPC for European Application No. 10797919.7, dated Jul. 19, 2013 (12 pages).
Office Action for Chinese Patent Application No. 201410034926.2, dated May 24, 2016 (8 pages).
Final Rejection for Japanese Patent Application No. 2009-537235, dated Oct. 1, 2013 (6 pages).
Paul, "Genes linked to kidney disease," Genetics Abstract, <http://geneticabstracts.blogspot.com/2008/10/genes-linked-to-kidney-disease.html>, retrieved on Aug. 22, 2011 (2 pages).
Vanhollebeke et al., "Distinct roles of haptoglobin-related protein and apolipoprotein L-I in trypanolysis by human serum," Proc Natl Acad Sci USA. 104(10):4118-23 (2007).
Vanhollebeke et al., "Human Trypanosoma evansi infection linked to a lack of apolipoprotein L-I," N Engl J Med. 355(26):2752-6 (2006).
International Search Report and Written Opinion of the International Searching Authority for International Application No. PCT/US12/39145, dated Dec. 7, 2012 (14 pages).

Office Action for Korean Patent Application No. 10-2009-7012908, dated May 14, 2013 (7 pages).
Office Action for U.S. Appl. No. 12/515,429, dated Oct. 7, 2011 (21 pages).
Igakuno ayumi, Vik. 167, No. 2, 1993, pp. 118-121.
Office Action for U.S. Appl. No. 12/515,429, dated Apr. 27, 2011 (17 pages).
Field et al., "Identification of the alpha2-delta-1 subunit of voltage-dependent calcium channels as a molecular target for pain mediating the analgesic actions of pregabalin," Proc Natl Acad Sci U S A. 103(46):17537-42 (2006).
Molina-Portela et al., "Distinct roles of apolipoprotein components within the trypanosome lytic factor complex revealed in a novel transgenic mouse model," J Exp Med. 205(8):1721-8 (2008).
Kaufman et al., "Transgenic analysis of a 100-kb human beta-globin cluster-containing DNA fragment propagated as a bacterial artificial chromosome," Blood. 94(9):3178-84 (1999).
Fishman et al., "Intravenous Lidocaine for Treatment-resistant Pruritus," Am J Med. 102(6):584-585 (1997).
Communication from European Patent Office for EP Application 11 007 949.8, dated Jun. 7, 2018 (6 pages).
Partial European Search Report for European Application No. 11 00 7949, dated Jun. 15, 2012 (16 pages).
Hahnenkamp et al., "Local anaesthetics inhibit signalling of human NMDA receptors recombinantly expressed in Xenopus laevis oocytes: role of protein kinase C," Br J Anaesth. 96(1):77-87 (2006).
Perez-Reyes, "Molecular physiology of low-voltage-activated T-type calcium channels," Physiol Rev. 83(1):117-61 (2003).
Vanhamme et al., "The trypanosome lytic factor of human serum and the molecular basis of sleeping sickness," Int J Parasitol 34(8):887-98 (2004).
Allen et al., "Clinical relevance of the neurotrophins and their receptors," Clin Sci (Lond). 110(2):175-91 (2006).
Examination Report for Australian Patent Application No. 2010271269, dated Jun. 29, 2016 (3 pages).
Anger et al., "Medicinal chemistry of neuronal voltage-gated sodium channel blockers," J. Med. Chem. 44(2):115-137 (2001).
Office Action for Chinese Patent Application No. 201410034926.2, dated Jul. 23, 2015 (13 pages).
Binshitok et al., "Inhibition of nociceptors by TRPV-1 mediated entry of impermeant sodium channel blockers," Nature. 449(7162):607-10 (2007).
Gribkoff, "Voltage-gated sodium channels in spinal ganglia: Tempting targets for new pain medications," Drug Discov Today. 3(4):585-91 (2006).
Birklein et al., "Neuropeptides, neurogenic inflammation and complex regional pain syndrome (CRPS)," Neurosci Lett. 437:199-202 (2008).
Ruparel et al., "Homologous and heterologous desensitization of capsaicin and mustard oil responses utilize different cellular pathways in nociceptors," Pain. 135(3):271-9 (2008).
Page et al., "The human apolipoprotein L gene cluster: identification, classification, and sites of distribution," Genomics 74(1):71-8 (2001).
Bonjardim et al., "Nociceptive behavior induced by mustard oil injection into the temporomandibular joint is blocked by a peripheral non-opioid analgesic and a central opioid analgesic," Pharmacol Biochem Behav. 91:321-326 (2009).
Amir et al., "The role of sodium channels in chronic inflammatory and neuropathic pain," J Pain. 7(5 Suppl 3):S1-29 (2006).
Shiyi, "Experimental study on analgesic effects of Epidural Capsaicin." Chin J Pain Med. 1(10):37-41 (2004) (English Abstract Provided).
Eller et al., "High affinity interaction of mibefradil with voltage-gated calcium and sodium channels," British Journal of Pharmacology, 130(3):669-677 (2000).
Cahalan et al., "Interactions between quaternary lidocaine, the sodium channel gates, and tetrodotoxin," Biophys J. 27(1):39-55 (1979).
European Patent Office Communication for European Patent Application No. 11007950.6, dated Feb. 27, 2012 (14 pages).
Strichartz et al., "The inhibition of sodium currents in myelinated nerve by quarternary derivatives of lidocaine," J Gen Physiol. 62:37-57 (1973).

(56) References Cited

OTHER PUBLICATIONS

Stys et al., "Tertiary and quaternary local anesthetics protect CNS white matter from anoxic injury at concentrations that do not block excitability," J Neurophysiol. 67:236-240 (1992).
European Patent Office Communication for European Patent Application No. 07862114.1, dated Sep. 23, 2009 (11 pages).
Kawamata et al., "Effects of systemic administration of lidocaine and QX-314 on hyperexcitability of spinal dorsal horn neurons after incision in the rat," Pain. 122(1-2):68-80 (2006).
Sullivan et al., "Synergistic inhibition of lysophosphatidic acid signaling by charged and uncharged local anesthetics," Anesth Analg. 88(5):1117-24 (1999).
Office Action for U.S. Appl. No. 14/496,629, dated May 12, 2016 (20 pages).
Gentry et al., "Local Anesthetics Noncompetitively Inhibit Function of Four Distinct Nicotinic Acetylcholine Receptor Subtypes," J Pharmacol Exp Ther. 299(3):1038-48 (2001).
Bautista et al., "Fire in the hole: pore dilation of the capsaicin receptor TRPV1," Nat Neurosci. 11(5):528-9 (2008).
International Preliminary Report on Patentability and Written Opinion for International Application No. PCT/US2010/041537, dated Jan. 10, 2012 (7 pages).
Szallasi et al., "The vanilloid receptor TRPV1: 10 years from channel cloning to antagonist proof-of-concept," Nat Rev Drug Discov. 6(5):357-72 (2007) (17 pages).
Wang et al., "N-Butyl Tetracaine as a Neurolytic Agent for Ultralong Sciatic Nerve Block," Anesthesiology 85:1386-1394 (1996). <http://journals.lww.com/anesthesiology/pages/articleviewer.aspx?year=1996&issue=1200 . . . > retrieved Dec. 15, 2008 (5 pages).
Yeh, "Sodium inactivation mechanism modulates QX-314 block of sodium channels in squid axons," Biophys J. 24(2):569-74 (1978).
International Search Report for International Application No. PCT/US2007/024174 dated Oct. 6, 2008 (9 pages).
International Search Report for International Application No. PCT/US2009/001541 dated Nov. 2, 2009.
Wood et al., "Voltage-gated sodium channel blockers; target validation and therapeutic potential," Current Topics in Medicinal Chemistry, 5(6):529-537 (2005). Abstract Only.
Office Action for Canadian Patent Application No. 2,767,646, dated Apr. 11, 2016 (4 pages).
Ikoma et al., "The neurobiology of itch," Nat Rev Neurosci. 7(7):535-47 (2006).
Ni et al., "Thermal sensitivity of isolated vagal pulmonary sensory neurons: role of transient receptor potential vanilloid receptors," Am J Physiol Regul Integr Comp Physiol. 291(3):R541-50 (2006).
Woolf, "Evidence for a central component of post-injury pain hypersensitivity," Nature. 306:686-688 (1983).
Canadian Office Action for Canadian Patent Application No. 2,668,652, dated Jul. 22, 2014 (3 pages).
Nielsen et al., "Bioreversible quaternary N-acyloxymethyl derivatives of the tertiary amines bupivacaine and lidocaine-synthesis, aqueous solubility and stability in buffer, human plasma and simulated intestinal fluid" European Journal of Pharmaceutical Sciences 24:433-440 (2005).
Adams et al., "The Bcl-2-regulated apoptosis switch: mechanism and therapeutic potential," available in PMC Sep. 29, 2009, published in final edited form as: Curr Opin Immunol. 19(5):488-96 (2007) (14 pages).
Written Opinion for International Application No. PCT/US2010/41537, dated Oct. 18, 2010 (3 pages).
Hartman et al., "Global changes in STAT target selection and transcription regulation upon interferon treatments," Genes Dev. 19(24):2953-68 (2005).
International Preliminary Report on Patentability and Written Opinion for Itnernational Application No. PCT/US2009/001541, dated Sep. 14, 2010 (9 pages).
Vieira et al. "Effect of ricinoleic acid in acute and subchronic experimental models of inflammation," Med of Inflam. 9(5):223-228 (2000).

Hellwig et al., "TRPV1 Acts as Proton Channel to Induce Acidification in Nociceptive Neurons," The Journal of Biological Chemistry 279:34553-34561 (2004).
NCBI Blast for Accession No. NM_145343.2. Retrieved on Jun. 9, 2015 (5 pages).
Office Action for Chinese Patent Application No. 200980117485.X, dated Apr. 23, 2013 (11 pages).
NCBI Blast for Accession No. CAQ09089.1. Retrieved on Jun. 9, 2015 (2 pages).
Yanagidate et al., "Local anesthetics," Handb Exp Pharmacol. 177:95-127 (2006).
NCBI Blast for Accession No. AAI42721.1. Retrieved on Jun. 9, 2015 (2 pages).
Freedman et al., "The apolipoprotein L1 (APOL1) gene and nondiabetic nephropathy in African Americans," J Am Soc Nephrol. 21(9):1422-6 (2010) (5 pages).
Bochner et al. "Immunological aspects of allergic asthma," Annu. Rev. Immunol. 12:295-335 (1994).
Exetended European Search Report for European Patent Application No. 11007949.8, dated Oct. 11, 2012 (32 pages).
Tzur et al., "Missense mutations in the APOL1 gene are highly associated with end stage kidney disease risk previously attributed to the MYH9 gene," Hum Genet. 128(3):345-50 (2010).
Office Action for Japanese Patent Application No. 2010-550687, dated Oct. 1, 2013 (6 pages).
Office Action in U.S. Appl. No. 13/404,725, dated Aug. 26, 2013 (11 pages).
Communication from European Patent Office for EP Application 10797919.7, dated Apr. 17, 2015 (7 pages).
Juengst, "What next for human gene therapy? Gene transfer often has multiple and unpredictable effects on cells," BMJ 326(7404):1410-1 (2003).
Jasmin et al., "The Cold Plate as a Test of Nociceptive Behaviors: Description and Application to the Study of Chronic Neuropathic and Inflammatory Pain Models," Pain 75:367-382 (1998).
Office Action for Canadian Patent Application No. 2,767,646, dated Nov. 1, 2017 (3 pages).
Office Action for Japanese Application No. 2012-519763, dated Jun. 23, 2015 (4 pages).
Wang et al., "Rapid analysis of gene expression (RAGE) facilitates universal expression profiling," Nucelic Acids Res. 27(23):4609-18 (1999).
Extended European Search Report for European Patent Application No. 15002768.8, dated Nov. 24, 2015 (9 pages).
Hahn et al., "Neuromyotonia in hereditary motor neuropathy," J Neurol Neurosurg Psychiatry. 54:230-5 (1991).
Bessac et al., "Breathtaking TRP channels: TRPA1 and TRPV1 in airway chemosensation and reflex control," Available in PMC Dec. 1, 2009, published in final edited form as: Physiology (Bethesda). 23:360-70 (2008) (20 pages).
Schwarz et al., "Effects of QX-314 on membrane properties of neurons in the ventrobasal thalamus," Proc West Pharmacol Soc. 45:29-31 (2002).
Snutch, "Targeting chronic and neuropathic pain: the N-type calcium channel comes of age," NeuroRx. 2(4):662-70 (2005).
Binshtok et al. "Lidocaine targets entry of the impermeant sodium channel blocker QX-314 into nociceptors to produce long-lasting regional analgesia," Program No. 170.6./KK27 2008 Neuroscience Meeting Planner. Washington, D.C.: Society for Neuroscience, 2008 (1 page). Online.
Donner et al., "New Generation Anticonvulsants for the Treatment of Epilepsy in Children," NeuroRx: The Journal of the American Society for Experimental NeuroTherapeutics, 3:170-180 (2006).
European Patent Office Communication pertaining to Application No. 07862114.1-2112, dated Sep. 15, 2011 (10 pages).
Tanelian et al., "Sodium channel-blocking agents: Their use in neuropathic pain conditions," Pain Forum. 4(2):75-80 (1995).
Lim et al., "The Quaternary Lidocaine Derivative, QX-314, Produces Long-lasting Local Anesthesia in Animal Models In Vivo," Anesthesiology 107:305-311 (2007).
Grantham et al., "Fluspirilene Block of N-Type Calcium Current in NGF-Differentiated PC12 Cells," Br. J. Pharmacol. 111:483-488 (1994).

(56) References Cited

OTHER PUBLICATIONS

Page et al., "Polymorphisms in the Apolipoprotein L1 gene and their effects on blood lipid and glucose levels in middle age males," Genes Nutr. 1(2):133-5 (2006).
Rich et al., "Quaternary quinidine derivatives as a tool to study: block of human potassium channels," Biophys J. 66(2):A143 (1994).
Wang et al., "Quaternary Ammonium Derivative of Lidocaine as a Long-acting Local Anesthetic," Anesthesiology 83:1293-1301 (1995). <http://journals.lww.com/anesthesiology/pages/articleviewer.aspx?year=1995&issue=1200 . . . > retrieved Dec. 15, 2008 (6 pages).
Kutchai et al., "Inhibition of the Na,K-ATPase of canine renal medulla by several local anesthetics," Pharmacol Res. 43(4):399-403 (2001).
Kochegarov, "Pharmacological modulators of voltage-gated calcium channels and their therapeutical application," Cell Calcium. 33(3):145-62 (2003).
Duchateau et al., "Apolipoprotein L, a new human high density lipoprotein apolipoprotein expressed by the pancreas. Identification, cloning, characterization, and plasma distribution of apolipoprotein L," J Biol Chem. 272(41):25576-82 (1997).
Written Opinion for International Application No. PCT/US2009/001541, dated Nov. 2, 2009 (8 pages).
Hu et al., "Human apolipoprotein L1 (ApoL1) in cancer and chronic kidney disease (Review Paper)," available in PMC Apr. 5, 2012, published in final edited form as: FEBS Lett. 586(7):947-55 (2012) (19 pages).
International Search Report and Written Opinion for International Application No. PCT/US13/70908, dated Apr. 23, 2014 (14 pages).
NCBI Blast for Accession No. Z82215.1. Retrieved on Jun. 9, 2015 (31 pages).
Yaksh, "Calcium channels as therapeutic targets in neuropathic pain," J Pain 7:S13-S30 (2006).
English translation of Office Action for Chinese Patent Application No. 201080040830.7, dated Mar. 8, 2013 (14 pages).
Extended European Search Report for European Patent Application No. 09718704.1, dated Dec. 11, 2012 (11 pages).
International Search Report for International Application No. PCT/US11/32924, dated Apr. 9, 2012 (6 pages).
Lee et al., "Role of TRPV1 in inflammation-induced airway hypersensitivity," Curr Opin Phamacol. 9(3):243-9 (2009).
Geppetti et al., "The transient receptor potential vanilloid 1: role in airway inflammation and disease," Eur J Pharmacol. 533(1-3):207-14 (2006).
Gibson et al., "The human serum resistance associated gene is ubiquitous and conserved in Trypanosoma brucei rhodesiense throughout East Africa," Infect Genet Evol. 1(3):207-14 (2002).
English Translation of Japanese Patent Office Communication dated Sep. 18, 2012, in Japanese Patent Application No. 2009-537235 (6 pages).
Puopolo et al. "Permeation and block of TRPV1 channels by cationic local anesthetics." Program No. 628.11. Neuroscience Meeting Planner, Sep. 10, 2008, Washington, D.C: Society for Neuroscience. Online (2 pages).
Examination Report for Australian Patent Application No. 2016262678, dated Oct. 13, 2017 (4 pages).
Cao, "Voltage-gated calcium channels and pain," Pain. 126(1-3):5-9 (2006).
Kirkpatrick et al., "Comparison of the effects of procaine, chlorpromazine and their quaternary derivatives on nerve action potentials," Res Commun Chem Pathol Pharmacol. 1(1):149-155 (1970).
Frazier et al., "The site of action and active form of local anesthetics. II. Experiments with quaternary compounds," J. Pharmacol. Exp. Ther. 171:45-51 (1970).
Office Action for South Korean Application No. 10-2009-7012908, dated May 14, 2013 (7 pages).
Winkelman et al., "Inhibition of the A-type K+ channels of dorsal root ganglion neurons by the long-duration anesthetic butamben," J Pharmacol Exp Ther. 314(3):1177-86 (2005).

Bley et al., "Extracellular application of QX-314 blocks sodium channels and causes local anesthesia," Soc Neurosci. 21:1820 (Abstract 716.7) (1995).
Woolf et al., "Neuropathic pain: aetiology, symptoms, mechanisms, and management," Lancet. 353(9168):1959-64 (1999).
NCBI Blast for Accession No. AF305224.1. Retrieved on Jun. 9, 2015 (2 pages).
Office Action for Chinese Patent Application No. 200780050131.9, dated Apr. 3, 2013 (8 pages).
NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).
Caceres et al., "A sensory neuronal ion channel essential for airway inflammation and hyperreactivity in asthma," Proc Natl Acad Sci U S A. 106(22):9099-104 (2009).
Curtis et al., "The Mechanism of Action of Local Anesthesia by Tetraethylammonium Derivatives," Anesthesiology 54:270-277 (1981).
Owsianik et al., "Permeation and selectivity of TRP channels," Annu Rev Physiol. 68:685-717 (2006).
Chen et al., "Differential Blockade of Nerve Injury-induced Thermal and Tactile Hypersensitivity by Systemically Administered Brain-penetrating and Peripherally Restricted Local Anesthetics," J. Pain 5:281-289 (2004).
Summons to Attend Oral Proceedings pursuant to Rule 115(1) EPC for European Patent Application No. 10797919.7, dated Apr. 17, 2015 (7 pages).
W.M. Edmondstone, "Chest pain and non-respiratory symptoms in acute asthma," Postgrad Med J 76(897):413-414 (2000).
Gribkoff, "The Role of Voltage-Gated Calcium Channels in Pain and Nociception," Semin. Cell Dev. Biol. 17:555-564 (2006).
NCBI Blast for Accession No. NP_003652.2. Retrieved on Jun. 9, 2015 (3 pages).
Written Opinion of the International Searching Authority for International Application No. PCT/US2007/024174 (18 pages).
Nielsen et al., "Assessment of the combined approach of N-alkylation and salt formation to enhance aqueous solubility of tertiary amines using bupivacaine as a model drug," Eur J of Pharm Sci. 24(1):85-93 (2005).
Lecordier et al., "C-terminal mutants of apolipoprotein L-I efficiently kill both Trypanosoma brucei brucei and Trypanosoma brucei rhodesiense," PLoS Pathog 5(12):e1000685 1-11 (2009).
Genovese et al., "Association of trypanolytic ApoL1 variants with kidney disease in African Americans," Science. 329(5993):841-5 (2010).
Qu et al., "Molecular determinants of drug access to the receptor site for antiarrhythmic drugs in the cardiac Na+ channel," Proc Natl Acad Sci USA. 92:11839-11843 (1995).
Extended European Search Report for European Patent Application No. 10797919.7, dated Oct. 29, 2012 (15 pages).
Blumberg, "Lighting a backfire to quench the blaze: A combined drug approach targeting the vanilloid receptor TRPV1," Molecular Interventions 7:310-312 (2007).
Written Opinion of the International Searching Authority for International Application No. PCT/US2011/32924, dated Apr. 9, 2012 (8 pages).
Hunt et al., "Treatment of asthma with nebulized lidocaine: a randomized, placebo-controlled study," J Allergy Clin Immunol. 113(5):853-9 (2004).
Australian Examination Report for Application No. 2012236902 dated Jul. 11, 2019.
Canadian Office Action for Canadian Patent Application No. 2,767,646, dated Nov. 1, 2017.
Chinese Office Action for Chinese Patent Application No. 201410034926.2, dated Jul. 23, 2015.
Extended European Search Report for European Patent Application No. 10797919.7, dated Oct. 29, 2012.
Extended European Search Report dated Apr. 23, 2019 for Application No. 18211462.9.
Japanese Office Action dated Apr. 16, 2019 for Application No. JP 2017-086446.
Written Opinion of the International Searching Authority for International Application No. PCT/US2007/024174.

(56) References Cited

OTHER PUBLICATIONS

International Search Report and Written Opinion for International Application No. PCT/US16/45354, dated Dec. 7, 2016.
Andre et al., Transient receptor potential ankyrin receptor 1 is a novel target for pro-tussive agents. Br J Pharmacol. Nov. 2009; 158(6):1621-8.
Berge et al., Pharmaceutical salts. J. Pharmaceutical Sciences 1977; 66(1):1-19.
Binshtok et al., Coapplication of lidocaine and the permanently charged sodium channel blocker QX-314 produces a long-lasting nociceptive blockade in rodents. Anesthesiology, 2009; 111(1):127-37.
Birrell et al., TRPA1 Agonists Evoke Coughing in Guinea-pig and Human Volunteers. Am J Respir Crit Care Med. Dec. 1, 2009; 180(11):1042-7.
Chiu et al., Bacteria activate sensory neurons that modulate pain and inflammation. Nature. Sep. 5, 2013; 501(7465):52-7. doi: 10.1038/nature12479. Epub Aug. 21, 2013.
Gennaro, Remington: The Science and Practice of Pharmacy, 20th edition, 2000, Lippincott Williams & Wilkins, Philadelphia.
Geppetti et al., The concept of neurogenic inflammation. BJU Int. Mar. 2008; 101 Suppl 3:2-6.
Green, Gastrin-releasing peptide, substance P and cytokines in rheumatoid arthritis. Arthritis Res. Ther. 2005; 7(3):111-3.
Gross et al., Role of neuropeptides in inflammatory bowel disease. Inflamm Bowel Dis 2007; 13(7):918-32.
Hill et al., TRPA1 is Differentially Modulated by the Amphipathic Molecules Trinitrophenol and Chlorpromazine J Biol Chem. 2007; 282:7145-7153.
Hille, The pH-dependent rate of action of local anesthetics on the node of Ranvier. Journal of General Physiology. 1977; 69(4), 475-96.
Joos et al., Role of tachykinins in asthma. Allergy 2000; 55(4):321-37.
Lin et al., Alternative splicing in the voltage-sensing region of N-Type CaV2.2 channels modulates channel kinetics. J Neurophysiol. Nov. 2004; 92(5):2820-30.
Liu et al., Potential independent action of sigma receptor ligands through inhibition of the Kv2.1 channel. Oncotarget. Aug. 29, 2017; 8(35): 59345-59358.
Longobardo et al., Effects of a quaternary bupivacaine derivative on delayed rectifier K+ currents. British Journal of Pharmacology. 2000;130(2): 391-401.
Lucioni et al., Botulinum toxin type A inhibits sensory neuropeptide release in rat bladder models of acute injury and chronic inflammation. BJU Int. Feb. 2008; 101(3):366-70.
March, Advanced Organic Chemistry: Reactions, Mechanisms and Structure, John Wiley & Sons, Inc., 1992, p. 617.
Moriya et al., Identification of 2-aminobenzimidazoles as potent melanin-concentrating hormone 1-receptor (MCH1R) antagonists. Bioorganic Med. Chem. Lett. 2009; 19(13):3568-3572.
Nazif et al., Neural upregulation in interstitial cystitis. Urology Apr. 2007; 69(4 Suppl):24-33.
Norman et al., Farnesyl and α-ionylideneethyl tertiary and quaternary amines: their influence on abscisic acid biosynthesis by Cercospora rosicola. Agricultural and Biological Chemistry 1985; 49(10):2893-8.
O'Connor et al., The role of substance P in inflammatory disease. J Cell Physiol 2004; 201(2):167-80.
O'Dell et al., Fatty acyl amides of endogenous tetrahydroisoquinolines are active at the recombinant human TRPV1 receptor. Bioorg Med Chem 2007; 15(18):6164-6149.
Paliani-Katsitadze et al., Comparative study of the antiarrhythmic effects of bonnecor and some mesidides of α-azacycloalkanecarboxylic acids. Eksperimental'naya i Klinicheskaya Farmakologiya. 1994; 57(3), 15-17.
Ren et al., Interactions between the immune and nervous systems in pain. Nat Med. Nov. 2010; 16(11):1267-76. Epub Oct. 14, 2010.

Renz et al., The role of neurotrophins in bronchial asthma: contribution of the pan-neurotrophin receptor p75. Prog Brain Res. 2004; 146:325-33.
Seko et al., Structure—Activity Study and Analgesic Efficacy of Amino Acid Derivatives as Ntype Calcium Channel Blockers Bioorganic & Medicinal Chemistry Letters Aug. 20, 2001; 11(16):2067-2070.
Spitzker et al., Mechanisms of potassium- and capsaicin-induced axonal calcitonin gene-related peptide release: involvement of L- and T-type calcium channels and TRPV1 but not sodium channels. Neuroscience 2008; 151(3):836-42.
Tarlap et al., Chemical modification of lyophilized proteins in nonaqueous environments. J Protein Chem. Apr. 1997;16(3):183-93.
Yamazaki et al., Syntheses of N1-(2-diethylaminoethyl)-p-aminobenzamide (Procainamide). J Pharm. Soc. Japan 1953; 73(3):294-97.
Singaporean Search Report, dated Mar. 12, 2019, in connection with Application No. 11201800919X.
Singaporean Search Report, dated Sep. 20, 2019, in connection with Application No. 11201800919X.
Aracava et al., Interactions of bupivacaine with ionic channels of the nicotinic receptor. Analysis of single-channel currents. Molecular Pharmacology. 1984; 26(2): 304-13.
Bernatowicz et al., 1H-Pyrazole-1-carboxamidine hydrochloride an attractive reagent for guanylation of amines and its application to peptide synthesis. J Org Chem. Apr. 1992;57(8):2497-2502.
Bernatowicz et al., Urethane protected derivatives of 1-guanylpyrazole for the mild and efficient preparation of guanidines. Tetranderon Lett.May 1993;34(21):3389-3392.
Brill, Esters of Aminobenzoic Acids. J Am. Chem. Soc. 1921; 43(6):1320-1323.
Clark et al., Derivatives of 3:4-xylidine and related compounds as inhibitors of influenza virus: relationships between chemical structure and biological activity. Br J Pharmacol Chemother. Dec. 1958;13(4):424-35.
Clinton et al., Derivatives of 4-Amino-2-hydroxybenzoic Acid. II. J Am. Chem. Soc. 1952; 74(3):592-598.
Creveling et al., Batrachotoxin-induced depolarization and [3H]batrachotoxinin-A 20α-benzoate binding in a vesicular preparation from guinea pig cerebral cortex: inhibition by local anesthetics. Molecular Pharmacology. 1983; 23(2), 350-8.
Fourneau et al., Stereoisomerism and local anesthetic action. Bull. Sci. Pharmacol. 1928; 35:273.
Guy, Neurogenic Factors in Contact Dermatitis. AMA Arch Derm Syphilol. 1952; 66(1):1-8.
Herrington et al., Identification of Novel and Selective KV2 Channel Inhibitors. Molecular Pharmacology. Dec. 2011; 80(6): 959-964.
Ikeda et al., Interactions of bupivacaine with ionic channels of the nicotinic receptor. Electrophysiological and biochemical studies. Molecular Pharmacology. 1984; 26(2), 293-303.
Kim et al., Monosubstituted guanidines from primary amines and aminoiminomethanesulfonic acid. Tetrahedron Lett. Dec. 1988;29(26):3183-3186.
Levine et al., The contribution of neurogenic inflammation in experimental arthritis. J Immunol. 1985; 135(2):843-847.
Macpherson et al., Noxious compounds activate TRPA1 ion channels through covalent modification of cysteines. Nature. Feb. 1, 2007; 445(7127):541-5.
Mayer et al., A RNA-Based Approach towards Small-Molecule Inhibitors. ChemBioChem 2009; 10(12):1993-1996.
Nguyen et al., Colitis induced by proteinase-activated receptor-2 agonists is mediated by a neurogenic mechanism. Canadian J. Phys. Pharm. 2003; 81(9):920-927.
Poss et al., A mild and efficient method for the preparation of guanidines. Tetrahedron Lett. Sep. 1992;33(40):5933-5936.
Preissl et al., Development of an assay for Complex I/Complex III of the respiratory chain using solid supported membranes and its application in mitochondrial toxicity screening in drug discovery. Assay Drug Dev Technol. Apr. 2011;9(2):147-56.
Ross et al., Formation of a piperidinium derivative from N-(5'-chloropentyl)-N-methylaminoaceto-2,6-xylidide in relation to the

(56) References Cited

OTHER PUBLICATIONS sustained local anaesthetic action on the sciatic nerve of the guinea-pig in vivo. Nat New Biol. Apr. 28, 1971;230(17):274-5.
Schlama et al., One-Step Synthesis of Chiral Guanidinium Salts from Phosgeniminium Salts. J. Org. Chem.1997; 62(12):4200-4202.
Sexton et al., 12-Lipoxygenase-derived eicosanoids protect against myocardial ischemia/reperfusion injury via activation of neuronal TRPV1. FASEB J. Sep. 2007; 21(11):2695-703.
Swarbrick et al., Encyclopedia of Pharmaceutical Technology, 1988-1999, Marcel Dekker, New York.
Taylor-Clark et al., Prostaglandin-induced activation of nociceptive neurons via direct interaction with transient receptor potential A1 (TRPA1). Mol Pharmacol. Feb. 2008;73(2):274-81.
U.S. Appl. No. 12/515,429, filed Dec. 21, 2009, Bean et al.
U.S. Appl. No. 14/496,629, filed Sep. 25, 2014, Bean et al.
U.S. Appl. No. 15/470,324, filed Mar. 27, 2017, Bean et al.
U.S. Appl. No. 16/245,895, filed Jan. 11, 2019, Bean et al.
U.S. Appl. No. 16/562,083, filed Sep. 5, 2019, Bean et al.
U.S. Appl. No. 13/382,834, filed Mar. 26, 2012, Woolf et al.
U.S. Appl. No. 16/216,489, filed Dec. 11, 2018, Woolf et al.
U.S. Appl. No. 16/246,885, filed Jan. 14, 2019, Woolf et al.
SG11201800919X, Mar. 12, 2019, Singaporean Search Report.
SG11201800919X, Sep. 20, 2019, Singaporean Search Report.
International Preliminary Report on Patentability for International Application No. PCT/US2016/045354, dated Feb. 15, 2018.
[No Author Listed], Wikipedia Page for Lidocaine. //en.wikipedia.org/wiki/lidocaine. [last accessed Sep. 22, 2020]. 1 page.
[No Author Listed], Wikipedia Page for Etidocaine. //en.wikipedia.org/wiki/etidocaine. [last accessed Sep. 22, 2020]. 1 page.
Covino et al., Pharmacokinetic Interaction of Local Anesthetics and Diazepam. Neue Aspekte in der Regionalanaesthesie 2. 1981;138:45-50.
McNeal et al., 2. [3H]Batrachotoxinin A 20α-Benzoate Binding to Voltage-Sensitive Sodium Channels: A Rapid and Quantitative Assay for Local Anesthetic Activity in a Variety of Drugs. J Med Chem. Mar. 1985;28(3):381-8. doi: 10.1021/jm00381a019.
Kalinin et al., Synthesis, local anaesthetic and antiarrhythmic activities of N-alkyl derivatives of proline anilides. Eur J Med Chem. 2013;63:144-150.
BR 112018002296-9, Jul. 28, 2020, Brazilian Office Action.
JP 2018-506119, Jul. 28, 2020, Japanese Office Action.

\* cited by examiner

FIG. 4A
FIG. 4B
FIG. 4C
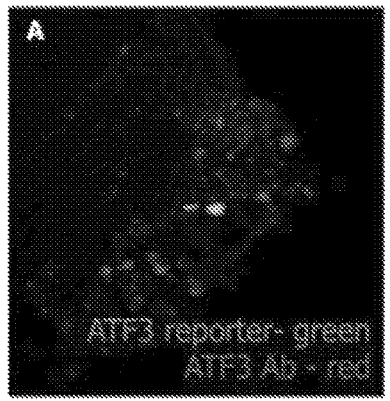
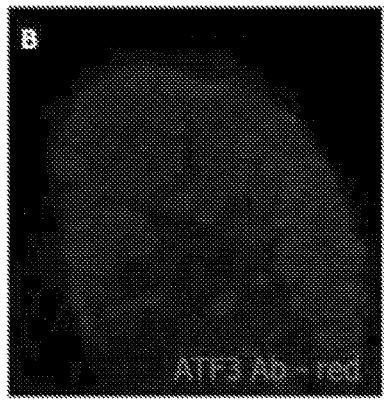
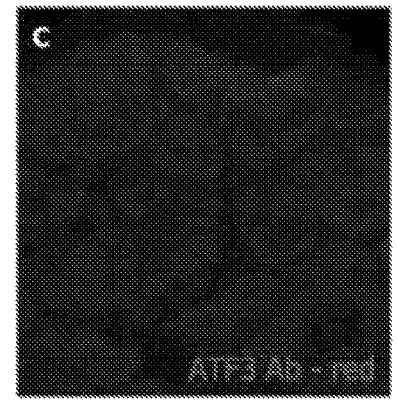

CHARGED ION CHANNEL BLOCKERS AND METHODS FOR USE

RELATED APPLICATIONS

This application is a national stage filing under 35 U.S.C. § 371 of international PCT application, PCT/US2016/045354, filed Aug. 3, 2016, which claims priority under 35 U.S.C. § 119(e) to U.S. Provisional Application, U.S. Ser. No. 62/200,205, filed on Aug. 3, 2015 each of which is incorporated herein by reference.

BACKGROUND OF THE INVENTION

The invention features compositions and methods for selective inhibition of pain-and itch sensing neurons (nociceptors and pruriceptors) and treatment of neurogenic inflammation by targeting nociceptors with drug molecules of small molecule weight, while minimizing effects on non-pain-sensing neurons or other types of cells. According to the method of the invention, small, hydrophilic drug molecules gain access to the intracellular compartment of pain-sensing neurons via entry through large pore receptor/ion channels that are present in pain- and itch-sensing neurons but to a lesser extent or not at all in other types of neurons or in other types of tissue.

Local anesthetics such as lidocaine and articaine act by inhibiting voltage-dependent sodium channels in neurons. These anesthetics block sodium channels and thereby the excitability of all neurons (an excitable cells in the cardiovascular system), not just pain-sensing neurons (nociceptors). Thus, while the goal of topical or regional anesthesia is to block transmission of signals in nociceptors to prevent pain, administration of local anesthetics also produces unwanted or deleterious effects such as general numbness from block of low threshold pressure and touch receptors, motor deficits from block of motor axons and other complications from block of autonomic fibers. Local anesthetics are relatively hydrophobic molecules that gain access to their blocking site on the sodium channel by diffusing into or through the cell membrane. Charged derivatives of these compounds (such as QX-314, a quaternary nitrogen derivative of lidocaine), which are not membrane-permeant, have no effect on neuronal sodium channels when applied to the external surface of the nerve membrane but can block sodium channels if somehow introduced inside the cell, for example by diffusion from a micropipette used for whole-cell electrophysiological recording from isolated neurons. Pain- and itch-sensing neurons differ from other types of neurons in expressing (in most cases) the TRPV1 receptor/channel, activated by painful heat or by capsaicin, the pungent ingredient in chili pepper. Other types of receptors selectively expressed in various types of pain-sensing and itch-sensing (pruriceptor) neurons include but are not limited to TRPA1, and P2X(2/3) receptors.

Neuropathic, inflammatory, and nociceptive pain differ in their etiology, pathophysiology, diagnosis, and treatment. Nociceptive pain occurs in response to the activation of a specific subset of high threshold peripheral sensory neurons, the nociceptors by intense or noxious stimuli. It is generally acute, self-limiting and serves a protective biological function by acting as a warning of potential or on-going tissue damage. It is typically well-localized. Examples of nociceptive pain include but are not limited to traumatic or surgical pain, labor pain, sprains, bone fractures, burns, bumps, bruises, injections, dental procedures, skin biopsies, and obstructions.

Inflammatory pain is pain that occurs in the presence of tissue damage or inflammation including postoperative, post-traumatic pain, arthritic (rheumatoid or osteoarthritis) pain and pain associated with damage to joints, muscle, and tendons as in axial low back pain, severe nociceptive pain may transition to inflammatory pain if there is associated tissue injury.

Neuropathic pain is a common type of chronic, non-malignant pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, surgery, herniation of an intervertebral disk, spinal cord injury, diabetes, infection with herpes zoster (shingles), HIV/AIDS, late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs.

Neuropathic pain is frequently described as "burning," "electric," "tingling," or "shooting" in nature. It is often characterized by chronic dynamic allodynia (defined as pain resulting from a moving stimulus that does not ordinarily elicit a painful response, such as light touch) and hyperalgesia (defined as an increased sensitivity to a normally painful stimulus), and may persist for months or years beyond the apparent healing of any damaged tissues.

Pain may occur in patients with cancer, which may be due to multiple causes; inflammation, compression, invasion, metastatic spread into bone or other tissues.

There are some conditions where pain occurs in the absence of a noxious stimulus, tissue damage or a lesion to the nervous system, called dysfunctional pain and these include but are not limited to fibromyalgia, tension type headache, and irritable bowel disorders.

Migraine is a headache associated with the activation of sensory fibers innervating the meninges of the brain.

Itch (pruritus) is a dermatological condition that may be localized and generalized and can be associated with skin lesions (rash, atopic eczema, wheals). Itch accompanies many conditions including but not limited to stress, anxiety, UV radiation from the sun, metabolic and endocrine disorders (e.g., liver or kidney disease, hyperthyroidism), cancers (e.g., lymphoma), reactions to drugs or food, parasitic and fungal infections, allergic reactions, diseases of the blood (e.g., polycythemia vera), and dermatological conditions. Itch is mediated by a subset of small diameter primary sensory neurons, the pruriceptor, that share many features of nociceptor neurons, including but not limited to expression of TRPV1 channels. Certain itch mediators—such as eicosanoids, histamine, bradykinin, ATP, and various neurotrophins have endovanilloid functions. Topical capsaicin suppresses histamine-induced itch. Pruriceptors like nociceptors are therefore a suitable target for this method of delivering ion channel blockers.

Neurogenic inflammation is a mode of inflammation mediated by the efferent (motor) functions of sensory neurons, in which pro-inflammatory mediator molecules released in the periphery by pain-sensing neurons (nociceptors) both activate a variety of inflammatory pathways in immune cells and also act on the vascular system to alter blood flow and capillary permeability.

Neurogenic inflammation contributes to the peripheral inflammation elicited by tissue injury, autoimmune disease, infection, allergy, exposure to irritants in a variety of tissues, and is thought to play an important role in the pathogenesis of numerous disorders (e.g. migraine, arthritis, rhinitis, gastritis, colitis, cystitis, and sunburn). One way to reduce neurogenic inflammation is to block excitability in nociceptors, thereby preventing the activation of nociceptor peripheral terminals and the release of pro-inflammatory chemicals.

Despite the development of a variety of therapies for pain, itch, and neurogenic inflammation, there is a need for additional agents.

SUMMARY OF THE INVENTION

In a first aspect, the invention features a quaternary amine compound having formula (I)

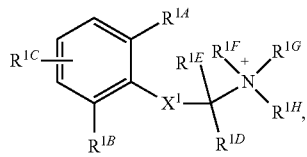

(I)

wherein $R^{1F}$ and $R^{1G}$ together complete a heterocyclic ring having at least one nitrogen atom; and wherein each of $R^{1A}$, $R^{1B}$, and $R^{1C}$ is independently selected from H, halogen, $C_{1-4}$ alkyl, $C_{2-4}$ alkenyl, $C_{2-4}$ alkynyl, $OR^{1I}$, $NR^{1J}R^{1K}$, $NR^{1L}C(O)R^{1M}$, $S(O)R^{1N}$, $SO_2R^{1O}$, $R^{1P}$, $SO_2NR^{1Q}R^{1R}$, $SO_3R^{1S}$, $CO_2R^{1T}$, $C(O)R^{1U}$, and $C(O)NR^{1V}R^{1W}$; and each of $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, and $R^{1W}$ is, independently, selected from H, $C_{1-4}$ alkyl, $C_{2-4}$ alkenyl, $C_{2-4}$ alkynyl, and $C_{2-4}$ heteroalkyl; wherein $X^1$ is selected from —$CR^{1X}R^{1Y}$—, —$NR^{1Z}C(O)$—, —OC(O)—, —SC(O)—, —$C(O)NR^{1AA}$—, —$CO_2$—, and —OC(S)—; and each of $R^{1X}$, $R^{1Y}$, $R^{1Z}$, and $R^{1AA}$ is independently selected from H, $C_{1-4}$ alkyl, $C_{2-4}$ alkenyl, $C_{2-4}$ alkynyl, and $C_{2-4}$ heteroalkyl; wherein each of $R^{1D}$ and $R^{1E}$ is independently selected from H, $C_{1-4}$ alkyl, $C_{2-4}$ alkenyl, $C_{2-4}$ alkynyl, $C_{2-4}$ heteroalkyl, optionally substituted with halogen, $C_{3-8}$ cyclic alkyl, aryl, or heteroaryl, and $C_{3-6}$ cycloalkyl or $R^{1D}$ and $R^{1E}$ together form a 3-6-membered heterocyclic or heteroalkyl ring; and wherein $R^{1H}$ is selected from $C_{1-4}$ alkyl, $C_{2-4}$ alkenyl, $C_{2-4}$ alkynyl, $C_{2-4}$ heteroalkyl, optionally substituted with halogen, $C_{3-8}$ cyclic alkyl, aryl, or heteroaryl, and $C_{3-6}$ cycloalkyl.

In some embodiments, $X^1$ is —NHC(O)—. In some embodiments, each of $R^{1A}$ and $R^{1B}$ is independently selected from H, halogen, $C_{1-4}$ alkyl, $C_{2-4}$ alkenyl, $C_{2-4}$ alkynyl, and $NR^{1J}R^{1K}$; and each of $R^{1J}$ and $R^{1K}$ is independently selected from H, $C_{1-4}$ alkyl, $C_{2-4}$ alkenyl, $C_{2-4}$ alkynyl, and $C_{2-4}$ heteroalkyl; or wherein at least one $R^{1C}$ is present. In certain other embodiments, $R^{1D}$ is $C_{1-4}$ alkyl optionally substituted with halogen, $C_{3-8}$ cyclic alkyl, aryl, or heteroaryl, $R^{1E}$ is H and $C_{1-4}$ alkyl optionally substituted with halogen, $C_{3-8}$ cyclic alkyl, aryl, or heteroaryl, or $R^{1H}$ is $C_{1-4}$ alkyl optionally substituted with halogen, $C_{3-8}$ cyclic alkyl, aryl, or heteroaryl.

In some embodiments, the compound is a compound in Table 1. In some embodiments, the compound is:

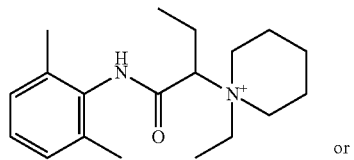

(Compound 6)

or

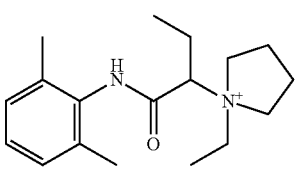

(Compound 3)

In a second aspect, the invention features a quaternary amine compound having formula (II)

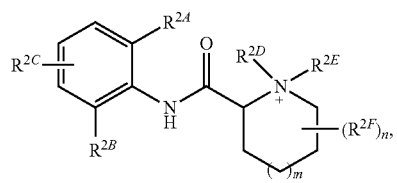

(II)

wherein m is 0 or 1; wherein each of $R^{2A}$, $R^{2B}$, and $R^{2C}$, is independently selected from H, halogen, $C_{1-4}$ alkyl, $C_{2-4}$ alkenyl, $C_{2-4}$ alkynyl, $CF_3$, $OR^2H$, $NR^{2I}R^{2J}$, $NR^{2K}C(O)R^{2L}$, $S(O)R^{2M}$, $SO_2R^{2N}R^{2O}$, $SO_2NR^{2P}R^{2Q}$, $SO_3R^{2R}$, $CO_2R^{2S}$, $C(O)R^{2T}$, and $C(O)NR^{2U}R^{2V}$; and each of $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, and $R^{2V}$ is, independently, selected from H, $C_{1-4}$ alkyl, $C_{2-4}$ alkenyl, $C_{2-4}$ alkynyl, and $C_{2-4}$ heteroalkyl; wherein n is 0, 1, 2, 3, 4, 5, 6, 7, 8, or 9 and each $R^{2F}$ is, independently, selected from halogen, $C_{1-4}$ alkyl, $C_{2-4}$ alkenyl, $C_{2-4}$ alkynyl, $CF_3$, $OR^2H$, $NR^{2I}N^{2J}$, $NR^{2K}C(O)R^{2L}$, $S(O)R^{2M}$, $SO_2R^{2N}R^{2O}$, $SO_2NR^{2P}R^{2Q}$, $SO_3R^{2R}$, $CO_2R^{2S}$, $C(O)R^{2T}$, and $C(O)NR^{2U}R^{2V}$; and each of $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, and $R^{2V}$ is, independently, selected from H, $C_{1-4}$ alkyl, $C_{2-4}$ alkenyl, $C_{2-4}$ alkynyl, and $C_{2-4}$ heteroalkyl; and wherein each of $R^{2D}$ and $R^{2E}$ is, independently, selected from $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl In some embodiments, each of $R^{2D}$ and $R^{2E}$ is $C_{1-4}$ alkyl that is optionally substituted with halogen, cyclic alkyl, aryl, or heteroaryl. In another embodiment, each of $R^{2A}$, $R^{2B}$, and $R^{2C}$ is independently selected from H, halogen, $C_{1-4}$ alkyl, and $CF_3$; or wherein at least one $R^{2C}$ is present; or wherein at least one $R^{2F}$ is present. In certain embodiments, the compound is a compound in Table 2. In some embodiments, the compound is

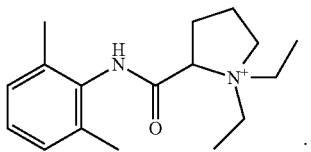
(Compound 14)

In a third aspect, the invention features a quaternary amine compound having general formula (III)

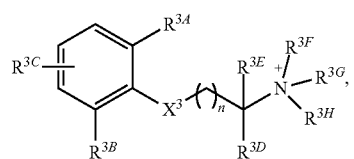
(III)

wherein
n is 0, 1, 2, or 3; wherein
each of $R^{3A}$, $R^{3B}$, and $R^{3C}$ is independently selected from H, halogen, $C_{1-4}$ alkyl, $C_{2-4}$ alkenyl, $C_{2-4}$ alkynyl, $OR^{3I}$, $NR^{3J}R^{3K}$, $NR^{3L}C(O)R^{3M}$, $S(O)R^{3N}$, $SO_2R^{3O}$, $R^{3P}$, $SO_2NR^{3Q}R^{3R}$, $SO_3R^{3S}$, $CO_2R^{3T}$, $C(O)R^{3U}$, and $C(O)NR^{3V}R^{3W}$; and each of $R^{3I}$, $R^{3J}R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, and $R^{3W}$ is independently selected from H, $C_{1-4}$ alkyl, $C_{2-4}$ alkenyl, $C_{2-4}$ alkynyl, and $C_{2-4}$ heteroalkyl; wherein
$X^3$ is selected from —NHC(O)—, and —C(O)NH; wherein
each of $R^{3D}$ and $R^{3E}$ can, independently, be selected from H, $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl, or $R^{1D}$ and $R^{1E}$ together can form a 3-6-membered heterocyclic or heteroalkyl ring; and wherein
each of $R^{3F}$, $R^{3G}$, and $R^{3H}$ is independently selected from $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl In particular embodiments, $X^3$ is —NHC(O)—. In other embodiments, n is 0 or 1. In some embodiments, each of $R^{3A}$, $R^{3B}$, and $R^{3C}$ is independently selected from H, $C_{1-4}$ alkyl, and $NR^{3J}R^{3K}$; and each of $R^{3J}$ and $R^{3K}$ is independently selected from H, $C_{1-4}$ alkyl, $C_{2-4}$ alkenyl, $C_{2-4}$ alkynyl, and $C_{2-4}$ heteroalkyl. In yet another embodiment, each of $R^{3E}$, $R^{3F}$, and $R^{3G}$ is independently selected from $C_{1-4}$ alkyl optionally substituted with halogen, cyclic alkyl, aryl, or heteroaryl, and $C_{3-6}$ cycloalkyl. In particular embodiments, the compound is any one of Compound Nos. 21-24 in Table 3. In yet another embodiment, the compound is

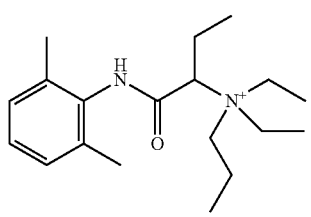
(Compound 21)

In a fourth aspect, the invention also features a composition including the quaternary amine compound of any one of the compounds in Tables 1-3 or a compound of formulas I through III and a pharmaceutically acceptable excipient. The composition can be formulated for oral, intravenous, intramuscular, rectal, cutaneous, subcutaneous, topical, transdermal, sublingual, nasal, inhalation, vaginal, intrathecal, epidural, or ocular administration.

In a fifth aspect, the invention features a method for treating pain, itch, or a neurogenic inflammatory disorder in a patient, the method including administering to the patient a composition including the quaternary amine compound of any one of the compounds in Tables 1-3 or a compound of formulas I through III, wherein the compound inhibits one or more voltage-gated ion channels present in nociceptors and/or pruriceptors when applied to the internal face of the channels but does not substantially inhibit the channels when applied to the external face of the channels, and wherein the compound is capable of entering nociceptors or pruriceptors through a channel-forming receptor when the receptor is activated and inhibiting the one or more voltage-gated ion channels present in the nociceptors.

In certain embodiments, the channel-forming receptor is a transient receptor potential ion channel (TRP channel-forming receptor). In other embodiments, the TRP channel-forming receptor is activated by an exogenous or endogenous agonist. In yet other embodiments, the TRP channel-forming receptor is TRPA1 or TRPV1. In particular embodiments, the compound is capable of entering nociceptors or pruriceptors through the TRPA1 or TRPV1 receptor when the receptor is activated. In yet other embodiments, the compound inhibits voltage-gated sodium channels. In yet another embodiment, the pain is selected from the group consisting of neuropathic pain, inflammatory pain, nociceptive pain, pain due to infections, and procedural pain, or wherein the neurogenic inflammatory disorder is selected from the group consisting of allergic inflammation, asthma, chronic cough, conjunctivitis, rhinitis, psoriasis, inflammatory bowel disease, and interstitial cystitis, atopic dermatitis. In particular embodiments, the compositions of the invention include a quaternary amine compound selected from the group consisting of:

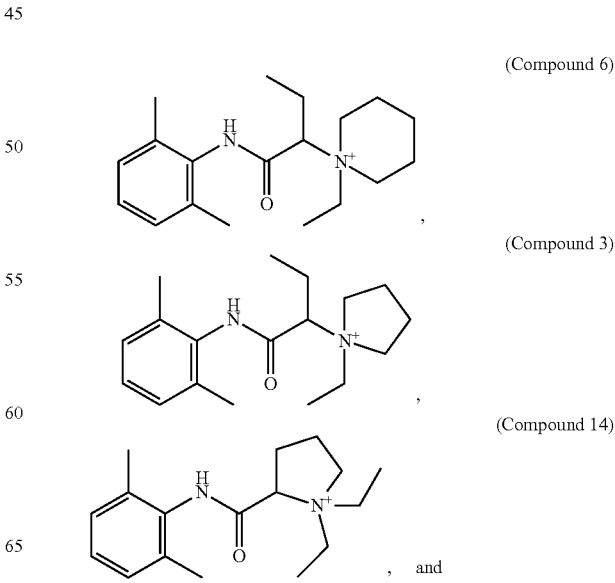

, and (Compound 21)

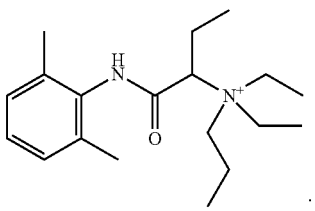

Definitions

By "biologically active" is meant that a molecule, including biological molecules, such as nucleic acids, peptides, polypeptides, and proteins, exerts a physical or chemical activity on itself or other molecule. For example, a "biologically active" molecule may possess, e.g., enzymatic activity, protein binding activity (e.g., antibody interactions), or cytotoxic activities (e.g., anti-cancer properties).

Biologically active agents that can be used in the methods and kits described herein include, without limitation, an antibody or antibody fragment, an antibiotic, a polynucleotide, a polypeptide, a protein, an anti-cancer agent, a growth factor, and a vaccine.

By "inflammation" is meant any types of inflammation, such those caused by the immune system (immune-mediated inflammation) and by the nervous system (neurogenic inflammation), and any symptom of inflammation, including redness, heat, swelling, pain, and/or loss of function.

By "neurogenic inflammation" is meant any type of inflammation mediated or contributed to by neurons (e.g. nociceptors) or any other component of the central or peripheral nervous system.

The term "pain" is used herein in the broadest sense and refers to all types of pain, including acute and chronic pain, such as nociceptive pain, e.g. somatic pain and visceral pain; inflammatory pain, dysfunctional pain, idiopathic pain, neuropathic pain, e.g., centrally generated pain and peripherally generated pain, migraine, and cancer pain.

The term "nociceptive pain" is used to include all pain caused by noxious stimuli that threaten to or actually injure body tissues, including, without limitation, by a cut, bruise, bone fracture, crush injury, burn, and the like. Pain receptors for tissue injury (nociceptors) are located mostly in the skin, musculoskeletal system, or internal organs.

The term "somatic pain" is used to refer to pain arising from bone, joint, muscle, skin, or connective tissue. This type of pain is typically well localized.

The term "visceral pain" is used herein to refer to pain arising from visceral organs, such as the respiratory, gastrointestinal tract and pancreas, the urinary tract and reproductive organs. Visceral pain includes pain caused by tumor involvement of the organ capsule. Another type of visceral pain, which is typically caused by obstruction of hollow viscus, is characterized by intermittent cramping and poorly localized pain. Visceral pain may be associated with inflammation as in cystitis or reflux esophagitis.

The term inflammatory pain includes pain associates with active inflammation that may be caused by trauma, surgery, infection and autoimmune diseases.

The term "neuropathic pain" is used herein to refer to pain originating from abnormal processing of sensory input by the peripheral or central nervous system consequent on a lesion to these systems.

The term "procedural pain" refers to pain arising from a medical, dental or surgical procedure wherein the procedure is usually planned or associated with acute trauma.

The term "itch" is used herein in the broadest sense and refers to all types of itching and stinging sensations localized and generalized, acute intermittent and persistent. The itch may be idiopathic, allergic, metabolic, infectious, drug-induced, due to liver, kidney disease, or cancer. "Pruritus" is severe itching.

By "patient" is meant any animal. In one embodiment, the patient is a human. Other animals that can be treated using the methods, compositions, and kits of the invention include but are not limited to non-human primates (e.g., monkeys, gorillas, chimpanzees), domesticated animals (e.g., horses, pigs, goats, rabbits, sheep, cattle, llamas), and companion animals (e.g., guinea pigs, rats, mice, lizards, snakes, dogs, cats, fish, hamsters, and birds).

Compounds useful in the invention include but are not limited to those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein.

By "low molecular weight" is meant less than about 500 Daltons.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include but are not limited to acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include but are not limited to sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, isobutyl, sec-butyl, tert-butyl, and cyclobutyl.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group. By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl, heteroalkyl, heteroaryl, and/or aryl groups, resulting in a positive charge at the nitrogen atom.

By "charged moiety" is meant a moiety which gains a proton at physiological pH thereby becoming positively charged (e.g., ammonium, guanidinium, or amidinium) or a moiety that includes a net formal positive charge without protonation (e.g., quaternary ammonium). The charged moiety may be either permanently charged or transiently charged.

As used herein, the term "parent" refers to a channel blocking compound which can be modified by quaternization or guanylation of an amine nitrogen atom present in the parent compound. The quaternized and guanylated compounds are derivatives of the parent compound. The guanidyl derivatives described herein are presented in their uncharged base form. These compounds can be administered either as a salt (i.e., an acid addition salt) or in their uncharged base form, which undergoes protonation in situ to form a charged moiety.

By "therapeutically effective amount" means an amount sufficient to produce a desired result, for example, the reduction or elimination of pain, itch, or neurogenic inflammation in a patient (e.g., a human) suffering from a condition, disease, or illness that is caused wholly or in part by neurogenic inflammation (e.g. asthma, arthritis, colitis, contact dermatitis, diabetes, eczema, cystitis, gastritis, migraine headache, psoriasis, rhinitis, rosacea, or sunburn).

Other features and advantages of the invention will be apparent from the following detailed description, and from the claims.

BRIEF DESCRIPTION OF THE DRAWINGS

FIGS. 2A and 2C show time course (0, 1, 6, and 24 hours) of changes in thermal nociceptive sensitivity measured as response latency (seconds) to a constant radiant heat source applied to the plantar surface of hind paw in mice co-treated with 20 μL (injected in the left hindpaw) of CFA (50% emulsion) and saline, and when the CFA was co-applied with QX-314 (1%, hollow square), N-ethyl etidocaine (Compound 21, 1%; dark square), or ACS8180-3B (Compound 3, 1%; solid triangle). FIGS. 2B and 2D show the nociceptive heat pain response time before CFA treatment and after treatment with the different compounds 1 hour post CFA injection. The data are means±SEM of 8-16 mice per group. The statistical comparison with pre-CFA (*) and with CFA+Vehicle (+) is indicated by +P<0.05; ++P<0.01 and +++,*** P<0.001.

FIG. 3A shows thermal nociceptive threshold observed between the contra and ipsilateral paw of rats that received (1 hour prior to testing) an acute intraplantar injection (50 μl) of saline, QX-314 (0.5%), or N-ethyl etidocaine (Compound 21) (0.5%). FIG. 3B shows thermal nociceptive threshold observed in rats that underwent surgical incision to their left hindpaw following injection of saline, QX-314, or N-ethyl etidocaine (Compound 21) compared to their contralateral paw. The data are means±SEM of 8 rats per group. The statistical comparison with the contralateral paw (*) is indicated by *** P<0.001.

FIGS. 4A-4C are results showing that N-ethyl-etidocaine (Compound 21) does not induce neurotoxicity. Representative picture of ATF3 (dark shading, FIGS. 4A-4C) expression in mice dorsal root ganglion slice exposed 8 weeks earlier to an acute hindpaw injection of CFA+N-ethyl-etidocaine (Compound 21) (1%, 20 μl).

DETAILED DESCRIPTION OF THE INVENTION

Figure 1A:
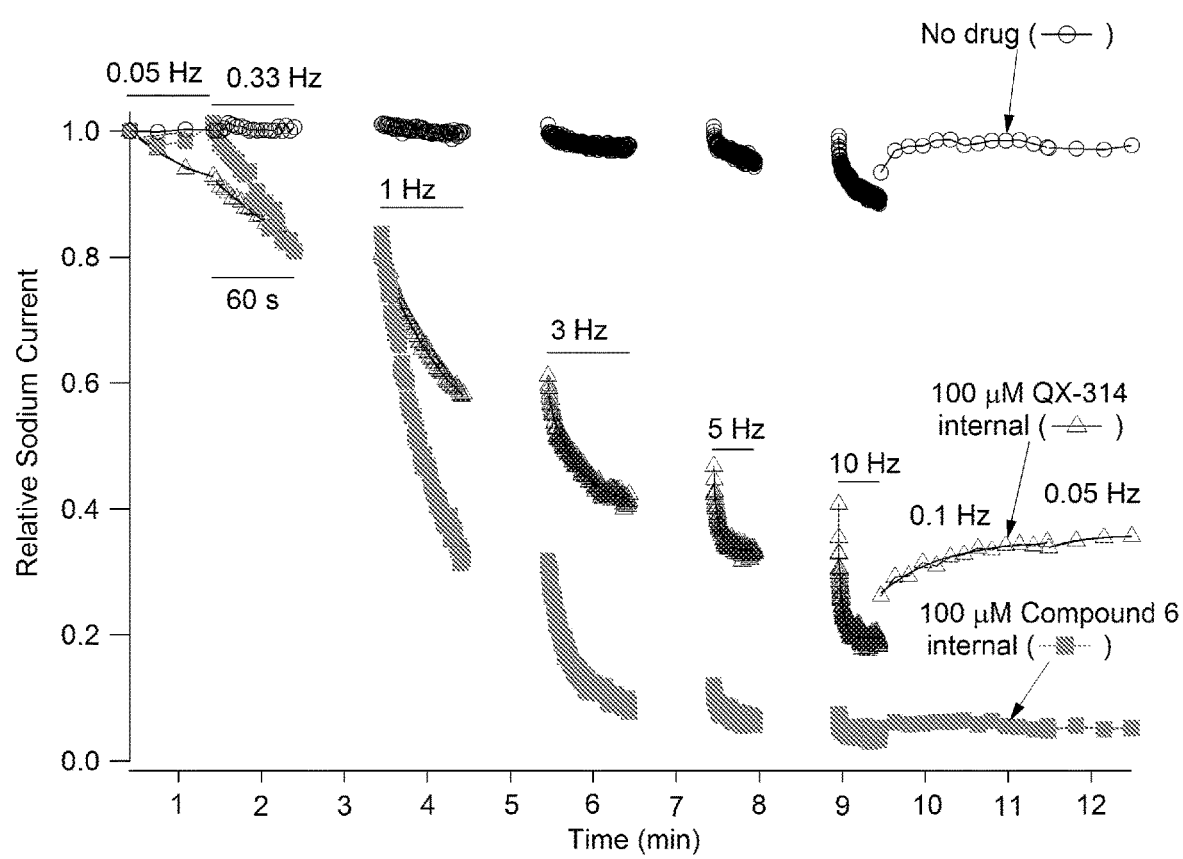
FIG. 1A shows use-dependent block of $Na_v1.7$ sodium channels by 100 μM QX-314 (middle trace) or the sodium channel blocker compound, BW 8186 (Compound 6) (bottom trace) applied intracellularly in whole-cell patch clamp recordings, with currents through sodium channels elicited by depolarizing voltage pulses applied at increasing frequencies, with rest periods in between to assay recovery from use-dependence. Top trace shows the lack of significant block when the same protocol was applied in the absence of drug.

We have identified new quaternary ammonium compounds that are capable of passing through open TRP channel-forming receptors that are expressed on nociceptors and/or pruriceptors but not on motor neurons that are more potent than QX-314 as ion channel blockers when applied inside cells. Because they are positively charged, the ion channel blockers of the present invention are not membrane-permeant and thus cannot enter cells that do not express TRP channel-forming receptors. Since TRP channel-forming receptors are often more active in tissue conditions associated with pain (such as inflammation) due to release of endogenous ligands or activation by thermal stimuli, the ion channel blockers of the invention can be used alone to selectively target activated nociceptors in order to effectively treat (e.g., eliminate or alleviate) pain, itch, or neurogenic inflammation. The ion channel blockers of the invention can also be used in combination with one or more exogenous TRP channel-forming receptor agonists to selectively target nociceptors in order to effectively treat (e.g., eliminate or alleviate) pain, itch, or neurogenic inflammation.

Voltage-dependent ion channels in pain-sensing neurons are currently of great interest in developing drugs to treat pain. Blocking voltage-dependent sodium channels in pain-sensing neurons can block pain signals by interrupting initiation and transmission of the action potential, and blocking calcium channels can prevent neurotransmission of the pain signal to the second order neuron in the spinal cord. Moreover, blocking voltage-dependent sodium channels in nociceptors can reduce or eliminate neurogenic inflammation by preventing activation of nociceptor peripheral terminals and the release thereof pro-inflammatory chemicals.

Heretofore, a limitation in designing small organic molecules that block sodium channels or calcium channels is that they must be active when applied externally to the target cell. The vast majority of such externally-applied molecules are hydrophobic and can pass through membranes. Because of this, they will enter all cells and thus have no selectivity for affecting only nociceptors.

Some inhibitors, such as the cationic lidocaine derivative QX-314, are membrane-impermeant and are only effective when present inside the nociceptor cell, and thus must pass through the cell membrane via a channel or receptor, such as a transient receptor potential ion channel (TRP channels, e.g., TRPAV1, TRPA1, and P2X(2/3)), in order to produce an effect. Under normal circumstances, most TRP channels in nociceptors are not active but require a noxious thermal, mechanical, or chemical stimulus to activate them. For example, TRP channels in nociceptors can be activated by an exogenous TRP ligand (i.e. TRP agonist) such as capsaicin, which opens the TRPV1 channel. Thus, one approach to selectively targeting nociceptors is to co-administer the membrane-impermeant ion channel inhibitor with an exogenous TRP ligand that permits passage of the inhibitor through the TRP channel into the cell. In addition to capsaicin, the exogenous TRP ligand can also be another capsaicinoid, mustard oil, or lidocaine. In another example, TRP channels may be active in response to exogenous irritant activators such as inhaled acrolein from smoke or chemical warfare agents such as tear gas.

Under certain circumstances, TRP channels can be activated in the absence of exogenous TRP agonists/ligands by endogenous inflammatory activators that are generated by tissue damage, infection, autoimmunity, atopy, ischemia, hypoxia, cellular stress, immune cell activation, immune mediator production, and oxidative stress. Under such conditions, endogenous molecules (e.g., protons, lipids, and reactive oxygen species) can activate TRP channels expressed on nociceptors, allowing membrane-impermeant, voltage-gated ion channel blockers to gain access to the inside of the nociceptor through the endogenously-activated TRP channels. Endogenous inflammatory activators of TRP channels include, for example, prostaglandins, nitric oxide (NO), peroxide ($H_2O_2$), cysteine-reactive inflammatory mediators like 4-hydroxynonenal, endogenous alkenyl aldehydes, endocannabinoids, and immune mediators (e.g., interleukin 1 (IL-1), nerve growth factor (NGF), and bradykinin, whose receptors are coupled to TRP channels).

The invention is described in more detail below.

Charged Ion Channel Blockers

Compounds that can be used in the compositions, kits, and methods of the invention include compounds of formulas (I).

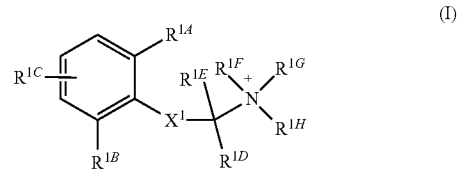

(I)

In formula (I), $R^{1F}$ and $R^{1G}$ together complete a heterocyclic ring having at least one nitrogen atom. In preferred embodiments, the heterocyclic ring is a 6-membered ring or a 5-membered ring. In addition, each of $R^{1A}$, $R^{1B}$, and $R^{1C}$ can, independently, be selected from H, halogen, $C_{1-4}$ alkyl, $C_{2-4}$ alkenyl, $C_{2-4}$ alkynyl, $OR^{1J}$, $NR^{1J}R^{1K}$, $NR^{1L}C(O)R^{1M}$, $S(O)R^{1N}$, $SO_2R^{1O}R^{1P}$, $SO_2NR^{1Q}$, $R^{1R}$, $SO_3R^{1S}$, $CO_2R^{1T}$, $C(O)R^{1U}$, and $C(O)NR^{1V}R^{1W}$; and each of $R^{1J}$, $R^{1J}R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, and $R^{1W}$ can, independently, be selected from H, $C_{1-4}$ alkyl, $C_{2-4}$ alkenyl, $C_{2-4}$ alkynyl, and $C_{2-4}$ heteroalkyl. In preferred embodiments, the compounds of the invention have at least one independent $R^{1C}$. $X^1$ can be selected from —$CR^{1X}R^{1Y}$—, —$NR^{1Z}C(O)$—, —OC(O)—, —SC(O)—, —$C(O)NR^{1AA}$—, —$CO_2$—, and —OC(S)—. In a preferred embodiment, $X^1$ is —NHC(O)—. Each of $R^{1X}$, $R^{1Z}$, and $R^{1AA}$ can, independently, be selected from H, $C_{1-4}$ alkyl, $C_{2-4}$ alkenyl, $C_{2-4}$ alkynyl, and $C_{2-4}$ heteroalkyl. Each of $R^{1D}$ and $R^{1E}$ can, independently, be selected from H, $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl, or $R^{1D}$ and $R^{1E}$ together can form a 3-6-membered ring (cyclic alkyl or heterocyclic). $R^{1H}$ can be selected from $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl. Exemplary compounds of formula (I) include those listed in Table 1. These compounds can be prepared using methods analogous to those described in Examples 1-6.

TABLE 1

| Compound No. | Molecular Structure | Molecular Weight | % Inhibition at 100 μM |
|---|---|---|---|
| 1 | 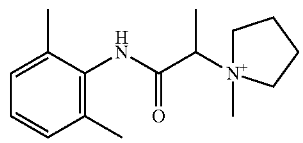 [SMILES: Cc1cccc(C)c1NC(=O)C(C)[N+]1(C)CCCC1] | 261.39 | 40 |
| 2 | 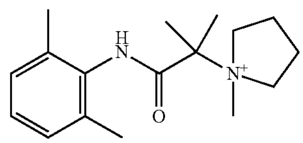 [SMILES: Cc1cccc(C)c1NC(=O)C(C)(C)[N+]1(C)CCCC1] | 275.42 | 42 |
| 3 | 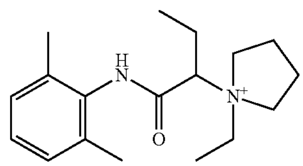 [SMILES: CCC(C(=O)Nc1c(C)cccc1C)[N+]1(CC)CCCC1] | 289.44 | 78 |
| 4 | 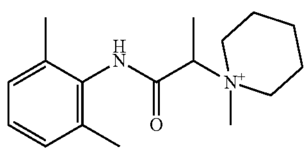 [SMILES: Cc1cccc(C)c1NC(=O)C(C)[N+]1(C)CCCCC1] | 275.42 | 43 |
| 5 | 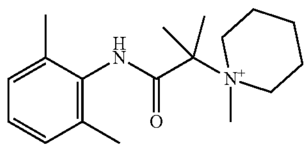 [SMILES: Cc1cccc(C)c1NC(=O)C(C)(C)[N+]1(C)CCCCC1] | 289.44 | 34 |
| 6 | 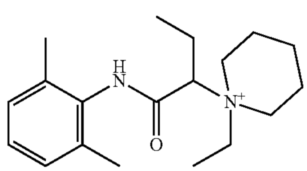 [SMILES: CCC(C(=O)Nc1c(C)cccc1C)[N+]1(CC)CCCCC1] | 303.47 | 83 |
| 7 | 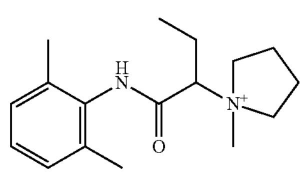 [SMILES: CCC(C(=O)Nc1c(C)cccc1C)[N+]1(C)CCCC1] | 275.42 | TBD |
| 8 | 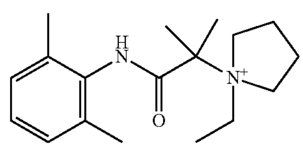 [SMILES: CC[N+]1(C(C)(C)C(=O)Nc2c(C)cccc2C)CCCC1] | 289.23 | TBD |
| 9 | 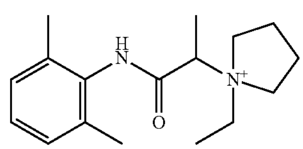 [SMILES: CC[N+]1(C(C)C(=O)Nc2c(C)cccc2C)CCCC1] | 275.42 | TBD |
| 10 | | 289.44 | TBD |
| 11 | | 303.47 | TBD |
| 12 | | 289.44 | TBD |

Compounds that can be used in the compositions, kits, and methods of the invention include compounds of formulas (II).

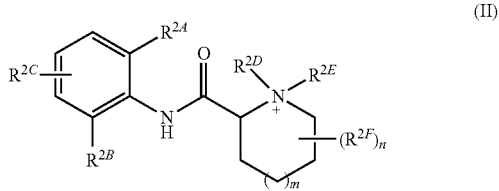

(II)

In formula (II), m can be 0 or 1, each of $R^{2A}$, $R^{2B}$, and $R^{2C}$ can, independently, be selected from H, halogen, $C_{1-4}$ alkyl, $C_{2-4}$ alkenyl, $C_{2-4}$ alkynyl, $CF_3$, $OR^{2H}$, $NR^{2I}R^{2J}$, $NR^{2K}C(O)R^{2L}$, $S(O)R^{2M}$, $SO_2R^{2N}R^{2O}$, $SO_2NR^{2P}R^{2Q}$, $SO_3R^{2R}$, $CO_2R^{2S}$, $C(O)R^{2T}$, and $C(O)NR^{2U}R^{2V}$; and each of $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, and $R^{2V}$ can, independently, be selected from H, $C_{1-4}$ alkyl, $C_{2-4}$ alkenyl, $C_{2-4}$ alkynyl, and $C_{2-4}$ heteroalkyl. n can be 0, 1, 2, 3, 4, 5, 6, 7, 8, or 9, and each $R^{2F}$ can, independently be selected from halogen, $C_{1-4}$ alkyl, $C_{2-4}$ alkenyl, $C_{2-4}$ alkynyl, $CF_3$, $OR^{2H}$, $NR^{2I}R^{2J}$, $NR^{2K}C(O)R^{2L}$, $S(O)R^{2M}$, $SO_2R^{2N}R^{2O}$, $SO_2NR^{2P}R^{2Q}$, $SO_3R^{2R}$, $CO_2R^{2S}$, $C(O)R^{2T}$, and $C(O)NR^{2U}R^{2V}$; and each of $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, and $R^{2V}$ can, independently, be selected from H, $C_{1-4}$ alkyl, $C_{2-4}$ alkenyl, $C_{2-4}$ alkynyl, and $C_{2-4}$ heteroalkyl. In preferred embodiments, the compounds of the invention have at least one independent $R^{2C}$. In another embodiment, compounds of the invention have at least one $R^{2F}$ and up to nine $R^{2F}$. $R^{2D}$ and $R^{2E}$ can be selected from $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl. Exemplary compounds of formula (II) include those listed in Table 2. These compounds can be prepared using methods analogous to those described in Examples 7-10.

TABLE 2

| Compound No. | Molecular Structure | Molecular Weight | % Inhibition at 100 μM |
|---|---|---|---|
| 13 | 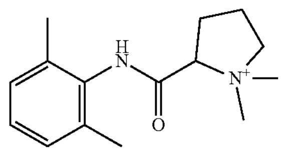 [SMILES: Cc1cccc(C)c1NC(=O)C1CCC[N+]1(C)C] | 247.36 | 33 |
| 14 | 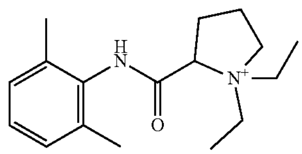 [SMILES: CC[N+]1(CC)CCCC1C(=O)Nc1c(C)cccc1C] | 275.42 | 62 |
| 15 | 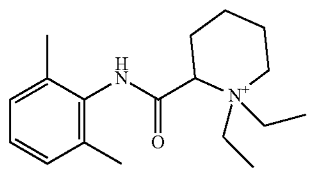 [SMILES: CC[N+]1(CC)CCCCC1C(=O)Nc1c(C)cccc1C] | 289.44 | 40 |
| 16 | 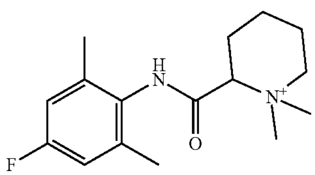 [SMILES: Cc1cc(F)cc(C)c1NC(=O)C1CCCC[N+]1(C)C] | 279.38 | 70 |
| 17 | 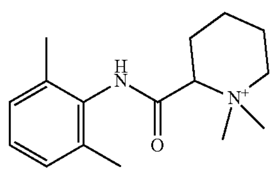 [SMILES: Cc1cccc(C)c1NC(=O)C1CCCC[N+]1(C)C] | 261.39 | TBD |
| 18 | 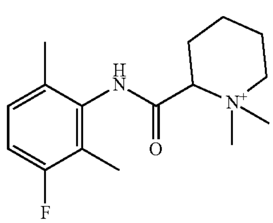 [SMILES: Cc1ccc(F)c(C)c1NC(=O)C1CCCC[N+]1(C)C] | 279.38 | TBD |
| 19 | | 315.36 | TBD |
| 20 | | 369.33 | TBD |

Compounds that can be used in the compositions, kits, and methods of the invention include compounds of formulas (III).

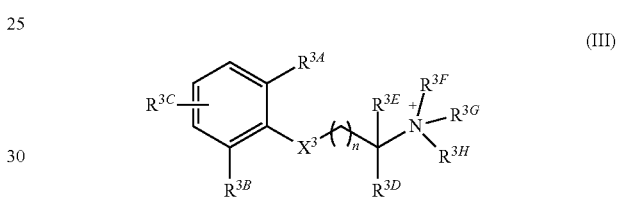

(III)

In formula (III), n can be 0, 1, 2, or 3, each of $R^{3A}$, $R^{3B}$, and $R^{3C}$ can, independently, be selected from H, halogen, $C_{1-4}$ alkyl, $C_{2-4}$ alkenyl, $C_{2-4}$ alkynyl, $OR^{3I}$, $NR^{3J}R^{3K}$, $NR^{3L}C(O)R^{3M}$, $S(O)R^{3N}$, $SO_2R^{3O}R^{3P}$, $SO_2NR^{3Q}R^{3R}$, $SO_3R^{3S}$, $CO_2R^{3T}$, $C(O)R^{3U}$, and $C(O)NR^{3V}R^{3W}$; and each of $R^{3I}$, $R^{3J}R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, and $R^{3W}$ can, independently, be selected from H, $C_{1-4}$ alkyl, $C_{2-4}$ alkenyl, $C_{2-4}$ alkynyl, and $C_{2-4}$ heteroalkyl. $X^3$ can be selected from —NHC(O)—, and —C(O)NH. Each of $R^{3D}$ and $R^{3E}$ can, independently, be selected from H, $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl, or $R^{3D}$ and $R^{3E}$ together can form a 3-6-membered ring (cyclic alkyl or heterocyclic). Each of $R^{3F}$, $R^{3G}$, and $R^{3H}$ can be selected from $C_{1-4}$ alkyl, $C_{2-4}$ alkenyl, $C_{2-4}$ alkynyl, $C_{2-4}$ heteroalkyl, optionally substituted with halogen, cyclic alkyl, aryl, or heteroaryl, and $C_{3-6}$ cycloalkyl. Exemplary compounds of formula (III) include those listed in Table 3. These compounds can be prepared using methods analogous to those described in Examples 11-14.

TABLE 3

| Compound No. | Molecular Structure | Molecular Weight | % Inhibition at 100 μM |
|---|---|---|---|
| 21 | 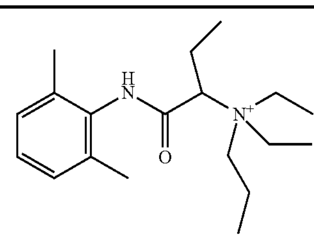 | 305.49 | 97 |

TABLE 3-continued

| Compound No. | Molecular Structure | Molecular Weight | % Inhibition at 100 μM |
|---|---|---|---|
| 22 | 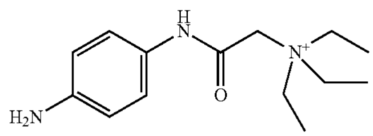 [SMILES: CC[N+](CC)(CC)CC(=O)Nc1ccc(N)cc1] | 250.37 | 0 |
| 23 | 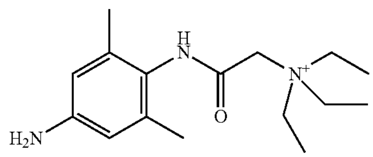 [SMILES: CC[N+](CC)(CC)CC(=O)Nc1c(C)cc(N)cc1C] | 278.42 | 56 |
| 24 | 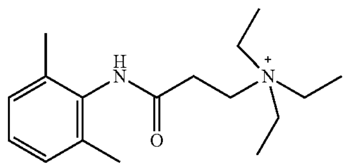 [SMILES: CC[N+](CC)(CC)CCC(=O)Nc1c(C)cccc1C] | 277.43 | 15 |
| 25 | 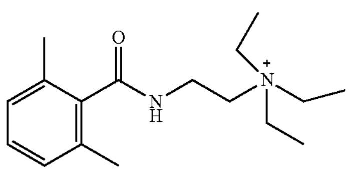 [SMILES: CC[N+](CC)(CC)CCNC(=O)c1c(C)cccc1C] | 277.43 | 3 |
| 26 | 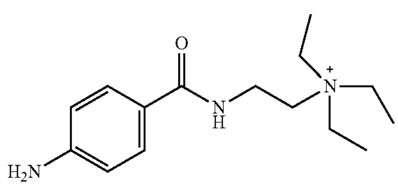 [SMILES: CC[N+](CC)(CC)CCNC(=O)c1ccc(N)cc1] | 264.39 | TBD |
| 27 | 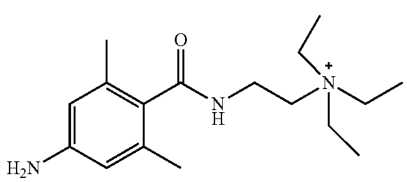 [SMILES: CC[N+](CC)(CC)CCNC(=O)c1c(C)cc(N)cc1C] | 292.45 | TBD |

Synthesis

The synthesis of charge-modified ion channel blockers may involve the selective protection and deprotection of alcohols, amines, ketones, sulfhydryls or carboxyl functional groups of the parent ion channel blocker, the linker, the bulky group, and/or the charged group. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994.

Charge-modified ion channel blockers can be prepared using techniques familiar to those skilled in the art. The modifications can be made, for example, by alkylation of the parent ion channel blocker using the techniques described by J. March, Advanced Organic Chemistry: Reactions, Mechanisms and Structure, John Wiley & Sons, Inc., 1992, page 617. The conversion of amino groups to guanidine groups can be accomplished using standard synthetic protocols. For example, Mosher has described a general method for preparing mono-substituted guanidines by reaction of amino-iminomethanesulfonic acid with amines (Kim et al., *Tetrahedron Lett.* 29:3183 (1988)). A more convenient method for guanylation of primary and secondary amines was developed by Bernatowicz employing 1H-pyrazole-1-carboxamidine hydrochloride; 1-H-pyrazole-1-(N,N'-bis(tert-butoxycarbonyl)carboxamidine; or 1-H-pyrazole-1-(N,N'-bis (benzyloxycarbonyl)carboxamidine. These reagents react with amines to give mono-substituted guanidines (see Bernatowicz et al., *J. Org. Chem.* 57:2497 (1992); and Bernatowicz et al., *Tetrahedron Lett.* 34:3389 (1993)). In addition, Thioureas and S-alkyl-isothioureas have been shown to be useful intermediates in the syntheses of substituted guanidines (Poss et al., *Tetrahedron Lett.* 33:5933 (1992)).

Charge-modified ion channel blockers can be prepared by alkylation of an amine nitrogen in the parent compound as shown in Scheme 1.

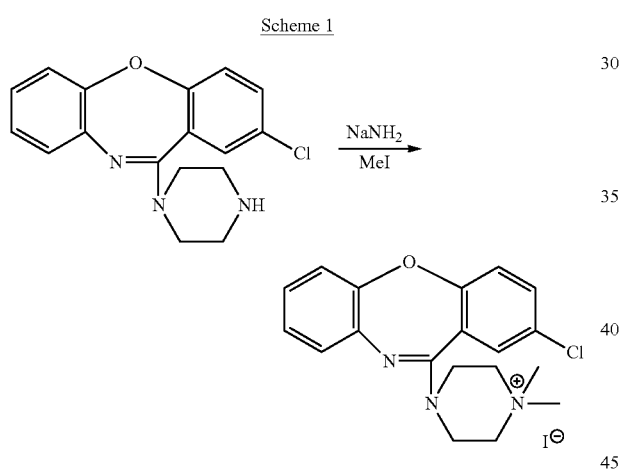

Alternatively, charge-modified ion channel blockers can be prepared by introduction of a guanidine group. The parent compound can be reacted with a cynamide, e.g., methylcyanamide or pyrazole-1-carboxamidine derivatives. Alternatively, the parent compound can be reacted with cyanogens bromide followed by reaction with methylchloroaluminum amide as shown in Scheme 2. Reagents such as 2-(methylthio)-2-imidazoline can also be used to prepare suitably functionalized derivatives (Scheme 3).

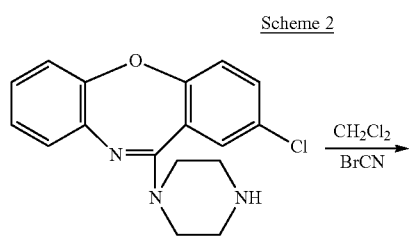

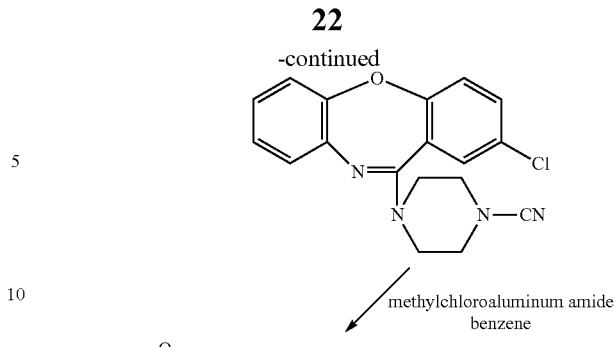

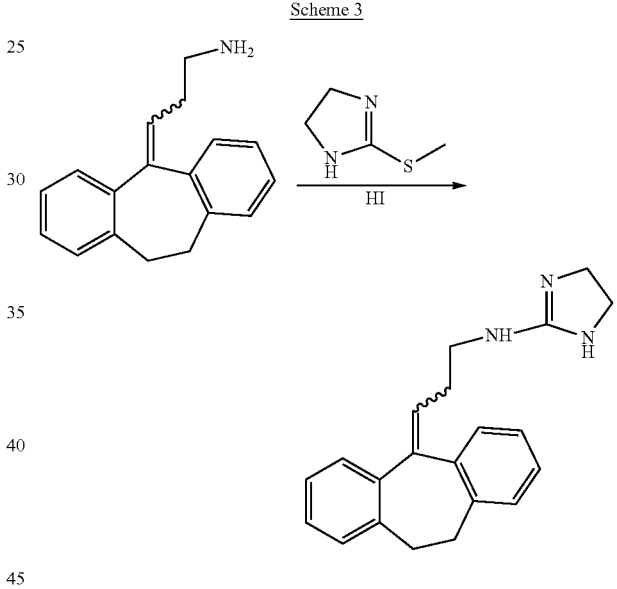

Any ion channel blocker containing an amine nitrogen atom can be modified as shown in Schemes 1-5. Exemplary synthetic schemes for particular charged ion channel blockers of the present invention are further detailed in Examples 1-14.

Exogenous TRP Channel-Forming Receptor Agonists

TRPV1 agonists that can be employed in the methods and kits of the invention include but are not limited to any that activates TRPV1 receptors on nociceptors and allows for entry of at least one inhibitor of voltage-gated ion channels. A suitable TRPV1 agonist is capsaicin or another capsaicinoids, which are members of the vanilloid family of molecules. Naturally occurring capsaicinoids are capsaicin itself, dihydrocapsaicin, nordihydrocapsaicin, homodihydrocapsaicin, homocapsaicin, and nonivamide. Other suitable capsaicinoids and capsaicinoid analogs and derivatives for use in the compositions and methods of the present invention include naturally occurring and synthetic capsaicin derivatives and analogs including, e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl)methyl]-9Z-octa-decanamide, N-oleyl-homovanillamide, triprenyl phenols (e.g., scutigeral), gingerols, piperines, shogaols, guaiacol, eugenol, zingerone, nuvanil, NE-19550, NE-21610, and NE-28345. Additional capsaicinoids, their structures, and methods of their manufacture are described in U.S. Pat. Nos. 7,446,226 and 7,429,673, which are hereby incorporated by reference.

Additional suitable TRPV1 agonists include but are not limited to eugenol, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hydroperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, and SU200 (N-(4-tert-butylbenzyl)-N'-(4-hydroxy-3-methoxybenzyl)thiourea). Still other TRPV1 agonists include amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine.

TRP1A agonists that can be employed in the methods, compositions, and kits of the invention include any that activates TRP1A receptors on nociceptors or pruriceptors and allows for entry of at least one inhibitor of voltage-gated ion channels. Suitable TRP1A agonists include but are not limited to cinnamaldehyde, allyl-isothiocynanate (mustard oil), diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, and 3'-carbamoylbiphenyl-3-yl cyclohexylcarbamate (URB597).

P2X agonists that can be employed in the methods, compositions, and kits of the invention include any that activates P2X receptors on nociceptors or pruriceptors and allows for entry of at least one inhibitor of voltage-gated ion channels. Suitable P2X agonists include but are not limited to 2-methylthio-ATP, 2' and 3'-O-(4-benzoylbenzoyl)-ATP, and ATP5'-O-(3-thiotriphosphate).

Additional Agents

If desired, one or more additional biologically active agents typically used to treat neurogenic inflammation may be used in combination with a composition of the invention described herein. The biologically active agents include, but are not limited to, acetaminophen, NSAIDs, glucocorticoids, narcotics (e.g. opioids), tricyclic antidepressants, amine transporter inhibitors, anticonvulsants, antiproliferative agents, and immune modulators. The biologically active agents can be administered prior to, concurrent with, or following administration of a composition of the invention, using any formulation, dosing, or administration known in the art that is therapeutically effective.

Non-steroidal anti-inflammatory drugs (NSAIDs) that can be administered to a patient (e.g., a human) suffering from neurogenic inflammation in combination with a composition of the invention include, but are not limited to, acetylsalicylic acid, amoxiprin, benorylate, benorilate, choline magnesium salicylate, diflunisal, ethenzamide, faislamine, methyl salicylate, magnesium salicylate, salicyl salicylate, salicylamide, diclofenac, aceclofenac, acemethacin, alclofenac, bromfenac, etodolac, indometacin, nabumetone, oxametacin, proglumetacin, sulindac, tolmetin, ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, sulfinpyrazone, piroxicam, droxicam, lornoxicam, meloxicam, tenoxicam, and the COX-2 inhibitors celecoxib, etoricoxib, lumiracoxib, parecoxib, rofecoxib, valdecoxib, and pharmaceutically acceptable salts thereof.

Glucocorticoids that can be administered to a patient (e.g., a human) suffering from neurogenic inflammation in combination with a composition of the invention include, but are not limited to, hydrocortisone, cortisone acetate, prednisone, prednisolone, methylprednisolone, dexamethasone, betamethasone, triamcinolone, beclometasone, fludrocortisone acetate, deoxycorticosterone acetate, aldosterone, and pharmaceutically acceptable salts thereof.

Narcotics that can be administered to a patient (e.g., a human) suffering from neurogenic inflammation in combination with a composition of the invention include, but are not limited, to tramadol, hydrocodone, oxycodone, morphine, and pharmaceutically acceptable salts thereof.

Antiproliferative and immune modulatory agents that can be administered to a patient (e.g., a human) suffering from neurogenic inflammation in combination with a composition of the invention include, but are not limited to, alkylating agents, platinum agents, antimetabolites, topoisomerase inhibitors, dihydrofolate reductase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF-alpha agonists, TNF-alpha antagonists or scavengers, interleukin 1 (IL-1) antagonists or scavengers, endothelin A receptor antagonists, retinoic acid receptor agonists, hormonal agents, anti-hormonal agents, photodynamic agents, and tyrosine kinase inhibitors.

Formulation of Compositions

The administration of the compounds of the invention may be by any suitable means that results in the reduction of perceived pain sensation at the target region. The compounds of the invention may be contained in any appropriate amount in any suitable carrier substance, and are generally present in amounts totaling 1-95% by weight of the total weight of the composition. The composition may be provided in a dosage form that is suitable for oral, parenteral (e.g., intravenous, intramuscular), rectal, cutaneous, subcutaneous, topical, transdermal, sublingual, nasal, vaginal, intrathecal, epidural, or ocular administration, or by injection, inhalation, or direct contact with the nasal or oral mucosa.

Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound may be formulated in a variety of ways that are known in the art. For example, the first and second agents may be formulated together or separately. Desirably, the first and second agents are formulated together for the simultaneous or near simultaneous administration of the agents.

The individually or separately formulated agents can be packaged together as a kit. Non-limiting examples include but are not limited to kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions.

The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Controlled Release Formulations

Each compound of the invention, alone or in combination with one or more of the biologically active agents as described herein, can be formulated for controlled release (e.g., sustained or measured) administration, as described in U.S. Patent Application Publication Nos. 2003/0152637 and 2005/0025765, each incorporated herein by reference. For example, a compound of the invention, alone or in combination with one or more of the biologically active agents as described herein, can be incorporated into a capsule or tablet that is administered to the site of inflammation.

Any pharmaceutically acceptable vehicle or formulation suitable for local infiltration or injection into a site to be treated (e.g., a painful surgical incision, wound, or joint), that is able to provide a sustained release of compound of the invention, alone or in combination with one or more of the biologically active agents as described herein, may be employed to provide for prolonged elimination or alleviation of inflammation, as needed. Slow release formulations known in the art include specially coated pellets, polymer formulations or matrices for surgical insertion or as sustained release microparticles, e.g., microspheres or microcapsules, for implantation, insertion, infusion or injection, wherein the slow release of the active medicament is brought about through sustained or controlled diffusion out of the matrix and/or selective breakdown of the coating of the preparation or selective breakdown of a polymer matrix. Other formulations or vehicles for sustained or immediate delivery of an agent to a preferred localized site in a patient include, e.g., suspensions, emulsions, gels, liposomes and any other suitable art known delivery vehicle or formulation acceptable for subcutaneous or intramuscular administration.

A wide variety of biocompatible materials may be utilized as a controlled release carrier to provide the controlled release of a compound of the invention, alone or in combination with one or more biologically active agents, as described herein. Any pharmaceutically acceptable biocompatible polymer known to those skilled in the art may be utilized. It is preferred that the biocompatible controlled release material degrade in vivo within about one year, preferably within about 3 months, more preferably within about two months. More preferably, the controlled release material will degrade significantly within one to three months, with at least 50% of the material degrading into non-toxic residues, which are removed by the body, and 100% of the compound of the invention being released within a time period within about two weeks, preferably within about 2 days to about 7 days. A degradable controlled release material should preferably degrade by hydrolysis, either by surface erosion or bulk erosion, so that release is not only sustained but also provides desirable release rates. However, the pharmacokinetic release profile of these formulations may be first order, zero order, bi- or multi-phasic, to provide the desired reversible local anesthetic effect over the desired time period.

Suitable biocompatible polymers can be utilized as the controlled release material. The polymeric material may comprise biocompatible, biodegradable polymers, and in certain preferred embodiments is preferably a copolymer of lactic and glycolic acid. Preferred controlled release materials which are useful in the formulations of the invention include the polyanhydrides, polyesters, co-polymers of lactic acid and glycolic acid (preferably wherein the weight ratio of lactic acid to glycolic acid is no more than 4:1 i.e., 80% or less lactic acid to 20% or more glycolic acid by weight)) and polyorthoesters containing a catalyst or degradation enhancing compound, for example, containing at least 1% by weight anhydride catalyst such as maleic anhydride. Examples of polyesters include polylactic acid, polyglycolic acid and polylactic acid-polyglycolic acid copolymers. Other useful polymers include protein polymers such as collagen, gelatin, fibrin and fibrinogen and polysaccharides such as hyaluronic acid.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539, incorporated herein by reference. Alternatively, copolymers of lactic and glycolic acid may be prepared by any other procedure known to those skilled in the art. Other useful polymers include polylactides, polyglycolides, polyanhydrides, polyorthoesters, polycaprolactones, polyphosphazenes, polyphosphoesters, polysaccharides, proteinaceous polymers, soluble derivatives of polysaccharides, soluble derivatives of proteinaceous polymers, polypeptides, polyesters, and polyorthoesters or mixtures or blends of any of these. Pharmaceutically acceptable polyanhydrides which are useful in the present invention have a water-labile anhydride linkage. The rate of drug release can be controlled by the particular polyanhydride polymer utilized and its molecular weight. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. The polyanhydride polymer may be branched or linear. Examples of polymers which are useful in the present invention include (in addition to homopolymers and copolymers of poly(lactic acid) and/or poly(glycolic acid)) poly[bis(p-carboxyphenoxy) propane anhydride] (PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids. Polyanhydrides may be prepared in accordance with the methods set forth in U.S. Pat. No. 4,757,128, incorporated herein by reference. Polyorthoester polymers may be prepared, e.g., as set forth in U.S. Pat. No. 4,070,347, incorporated herein by reference. Polyphosphoesters may be prepared and used as set forth in U.S. Pat. Nos. 6,008,318, 6,153,212, 5,952,451, 6,051,576, 6,103,255, 5,176,907 and 5,194,581, each of which is incorporated herein by reference.

Proteinaceous polymers may also be used. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-valine, L-tyrosine, and the like.

In additional embodiments, the controlled release material, which in effect acts as a carrier for a compound of the invention, alone or in combination with one or more biologically active agents as described herein, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

In embodiments where the biodegradable polymer comprises a gel, one such useful polymer is a thermally gelling polymer, e.g., polyethylene oxide, polypropylene oxide (PEO-PPO) block copolymer such as Pluronic™ F127 from BASF Wyandotte. In such cases, the local anesthetic formulation may be injected via syringe as a free-flowing liquid, which gels rapidly above 30° C. (e.g., when injected into a patient). The gel system then releases a steady dose of a compound of the invention, alone or in combination with one or more biologically active agents as described herein, at the site of administration.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration will be indicated in many cases.

Parenteral Formulations

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Topical Formulations

A composition of the invention, alone or in combination with one or more of the biologically active agents described herein, can also be adapted for topical use with a topical vehicle containing from between 0.0001% and 25% (w/w) or more of active ingredient(s).

In a preferred combination, the active ingredients are preferably each from between 0.0001% to 10% (w/w), more preferably from between 0.0005% to 4% (w/w) active agent. The cream can be applied one to four times daily, or as needed. Performing the methods described herein, the topical vehicle containing the composition of the invention, or a combination therapy containing a composition of the invention is preferably applied to the site of inflammation on the patient. For example, a cream may be applied to the hands of a patient suffering from arthritic fingers.

The compositions can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The therapeutic agents may also be administered in liposomal formulations that allow therapeutic agents to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; 8,822,537, and PCT Publication No. WO 96/40061. Examples of other appropriate vehicles are described in U.S. Pat. Nos. 4,877,805, 8,822,537, and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil.

The composition can further include a skin penetrating enhancer, such as those described in "Percutaneous Penetration enhancers", (eds. Smith E W and Maibach H I. CRC Press 1995). Exemplary skin penetrating enhancers include alkyl (N,N-disubstituted amino alkanoate) esters, such as dodecyl 2-(N,N dimethylamino) propionate (DDAIP), which is described in patents U.S. Pat. Nos. 6,083,996 and 6,118,020, which are both incorporated herein by reference; a water-dispersible acid polymer, such as a polyacrylic acid polymer, a carbomer (e.g., Carbopol™ or Carbopol 940P™, available from B. F. Goodrich Company (Akron, Ohio)), copolymers of polyacrylic acid (e.g., Pemulen™ from B. F. Goodrich Company or Polycarbophil™ from A. H. Robbins, Richmond, Va.; a polysaccharide gum, such as agar gum, alginate, carrageenan gum, ghatti gum, karaya gum, kadaya gum, rhamsan gum, xanthan gum, and galactomannan gum (e.g., guar gum, carob gum, and locust bean gum), as well as other gums known in the art (see for instance, Industrial Gums: Polysaccharides & Their Derivatives, Whistler R. L., BeMiller J. N. (eds.), 3rd Ed. Academic Press (1992) and Davidson, R. L., Handbook of Water-Soluble Gums & Resins, McGraw-Hill, Inc., N.Y. (1980)); or combinations thereof.

Other suitable polymeric skin penetrating enhancers are cellulose derivatives, such as ethyl cellulose, methyl cellulose, hydroxypropyl cellulose. Additionally, known transdermal penetrating enhancers can also be added, if desired. Illustrative are dimethyl sulfoxide (DMSO) and dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide, N-methyl-2-pyrrolidone, calcium thioglycolate and other enhancers such as dioxolanes, cyclic ketones, and their derivatives and so on.

Also illustrative are a group of biodegradable absorption enhancers which are alkyl N,N-2-(disubstituted amino) alkanoates as described in U.S. Pat. Nos. 4,980,378 and 5,082,866, which are both incorporated herein by reference, including: tetradecyl (N,N-dimethylamino) acetate, dodecyl (N,N-dimethylamino) acetate, decyl (N,N-dimethylamino) acetate, octyl (N,N-dimethylamino) acetate, and dodecyl (N,N-diethylamino) acetate.

Particularly preferred skin penetrating enhancers include isopropyl myristate; isopropyl palmitate; dimethyl sulfoxide; decyl methyl sulfoxide; dimethylalanine amide of a medium chain fatty acid; dodecyl 2-(N,N-dimethylamino) propionate or salts thereof, such as its organic (e.g., hydrochloric, hydrobromic, sulfuric, phosphoric, and nitric acid addition salts) and inorganic salts (e.g., acetic, benzoic, salicylic, glycolic, succinic, nicotinic, tartaric, maleic, malic, pamoic, methanesulfonic, cyclohexanesulfamic, picric, and lactic acid addition salts), as described in U.S. Pat. No. 6,118,020; and alkyl 2-(N,N-disubstituted amino)-alkanoates, as described in U.S. Pat. Nos. 4,980,378 and 5,082,866.

The skin penetrating enhancer in this composition by weight would be in the range of 0.5% to 10% (w/w). The most preferred range would be between 1.0% and 5% (w/w). In another embodiment, the skin penetrating enhancer comprises between 0.5%-1%, 1%-2%, 2%-3%, 3%-4%, or 4%-5%, (w/w) of the composition.

The compositions can be provided in any useful form. For example, the compositions of the invention may be formulated as solutions, emulsions (including microemulsions), suspensions, creams, foams, lotions, gels, powders, or other typical solid, semi-solid, or liquid compositions (e.g., topical sprays) used for application to the skin or other tissues where the compositions may be used. Such compositions may contain other ingredients typically used in such products, such as colorants, fragrances, thickeners (e.g., xanthan gum, a fatty acid, a fatty acid salt or ester, a fatty alcohol, a modified cellulose, a modified mineral material, Krisgel 100™, or a synthetic polymer), antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetrating enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

The compositions can also include other like ingredients to provide additional benefits and improve the feel and/or appearance of the topical formulation. Specific classes of additives commonly use in these formulations include: isopropyl myristate, sorbic acid NF powder, polyethylene glycol, phosphatidylcholine (including mixtures of phosphatidylcholine, such as phospholipon G), Krisgel 100™ distilled water, sodium hydroxide, decyl methyl sulfoxide (as a skin penetrating enhancer), menthol crystals, lavender oil, butylated hydroxytoluene, ethyl diglycol reagent, and 95% percent (190 proof) ethanol.

Formulations for Ophthalmic Administration

The compounds of the invention can also be formulated with an ophthalmically acceptable carrier in sufficient concentration so as to deliver an effective amount of the active compound or compounds to the optic nerve site of the eye. Preferably, the ophthalmic, therapeutic solutions contain one or more of the active compounds in a concentration range of approximately 0.0001% to approximately 1% (weight by volume) and more preferably approximately 0.0005% to approximately 0.1% (weight by volume).

An ophthalmically acceptable carrier does not cause significant irritation to the eye and does not abrogate the pharmacological activity and properties of the charged sodium channel blockers.

Ophthalmically acceptable carriers are generally sterile, essentially free of foreign particles, and generally have a pH in the range of 5-8. Preferably, the pH is as close to the pH of tear fluid (7.4) as possible. Ophthalmically acceptable carriers are, for example, sterile isotonic solutions such as isotonic sodium chloride or boric acid solutions. Such carriers are typically aqueous solutions contain sodium chloride or boric acid. Also useful are phosphate buffered saline (PBS) solutions.

Various preservatives may be used in the ophthalmic preparation. Preferred preservatives include, but are not limited to, benzalkonium potassium, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose and hydroxyethyl cellulose.

Tonicity adjustors may be added as needed or convenient. They include, but are not limited to, salts, particularly sodium chloride, potassium chloride, etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed. Ophthalmically acceptable antioxidants can also be include. Antioxidants include but are not limited to sodium metabisulfite, sodium thiosulfate, acetylcysteine, butylated hydroxyanisole, and butylated hydroxytoluene.

Formulations for Nasal and Inhalation Administration

The pharmaceutical compositions of the invention can be formulated for nasal or intranasal administration. Formulations suitable for nasal administration, when the carrier is a solid, include a coarse powder having a particle size, for example, in the range of approximately 20 to 500 microns which is administered by rapid inhalation through the nasal passage. When the carrier is a liquid, for example, a nasal spray or as nasal drops, one or more of the formulations can be admixed in an aqueous or oily solution, and inhaled or sprayed into the nasal passage.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount, Capsules and cartridges of, for example, gelatin for use in an inhaler or insufflator can be formulated containing a powder mix of the compound and a suitable powder base such as lactose or starch.

Indications

The methods, compositions, and kits of the invention can be used to treat pain or itch associated with any of a number of conditions, including back and neck pain, cancer pain, gynecological and labor pain, fibromyalgia, arthritis and other rheumatological pains, orthopedic pains, post herpetic neuralgia and other neuropathic pains, sickle cell crises, interstitial cystitis, urethritis and other urological pains, dental pain, headaches, postoperative pain, and procedural pain (i.e., pain associated with injections, draining an abscess, surgery, dental procedures, opthalmic procedures, ophthalmic irritation, conjunctivitis (e.g., allergic conjunctivitis), eye redness, dry eye, arthroscopies and use of other medical instrumentation, cosmetic surgical procedures, dermatological procedures, setting fractures, biopsies, and the like).

Since a subclass of nociceptors mediate itch sensation the methods, compositions, and kits of the invention can also be used to treat itch in patients with conditions like dermatitis, infections, parasites, insect bites, pregnancy, metabolic disorders, liver or renal failure, drug reactions, allergic reactions, eczema, and cancer.

The methods, compositions, and kits of the invention can also be used for the treatment of pyrexia (fever), hyperpyrexia, malignant hyperthermia, or a condition characterized by elevated body temperature.

The methods, compositions, and kits of the invention can also be used to treat neurogenic inflammation and neurogenic inflammatory disorders. Inflammation is a complex set of responses to harmful stimuli that results in localized redness, swelling, and pain. Inflammation can be innate or adaptive, the latter driven by antigens and is mediated by immune cells (immune-mediated inflammation). Neurogenic inflammation results from the efferent functions of pain-sensing neurons (nociceptors), wherein neuropeptides and other chemicals that are pro-inflammatory mediators are released from the peripheral terminals of the nociceptors when they are activated. This release process is mediated by calcium influx and exocytosis of peptide containing vesicles, and the pro-inflammatory neuropeptides include substance P, neurokinin A and B (collectively known as tachykinins), calcitonin gene-related peptide (CGRP), and vasoactive intestinal polypeptide (VIP).

The release of peripheral terminal chemicals stimulate a variety of inflammatory responses. First, the release of substance P can result in an increase in capillary permeability such that plasma proteins leak from the intravascular compartment into the extracellular space (plasma extravasation), causing edema. This can be detected as a wheal (a firm, elevated swelling of the skin) which is one component of a triad of inflammatory responses—wheal, red spot, and flare—known as the Lewis triple response.

Second, the release of CGRP causes vasodilation, leading to increased blood flow. This can be detected as a flare, which is another component of the Lewis triple response.

Substance P also has a pro-inflammatory action on immune cells (e.g. macrophages, T-cells, mast cells, and dendritic cells) via their neurokinin-1 (NK1) receptor. This effect has been documented in allergic rhinitis, gastritis, and colitis, and represents an interface between the neurogenic and immune-mediated components of inflammation. Substance P released from one nociceptor may also act on NK1 receptors on neighboring nociceptors to sensitize or activate them, causing a spread of activation and afferent/efferent function. These efferent functions of nociceptors can be triggered by: 1) Direct activation of a nociceptor terminal by a peripheral adequate stimulus applied to the terminal (e.g. a pinch); 2) Indirect antidromic activation of a non-stimulated nociceptor terminal by the axon reflex, wherein action potential input from one terminal of a nociceptor, upon reaching a converging axonal branch point in the periphery, results in an action potential traveling from the branch point down to the peripheral terminal of a non-stimulated terminal; and 3) Activation as a result of activity in nociceptor central terminals in the CNS traveling to the periphery (e.g., primary afferent depolarization of central terminals produced by GABA can be sufficient to initiate action potentials traveling the "wrong way").

Genomic analysis of lung resident ILC2 cells has revealed expression of receptors for several neuropeptides released by sensory neurons, including SP, CGRP and VIP, providing an opportunity for nociceptors to directly communicate with these cells. In particular, VIP is found to be expressed in NaV1.8+ nodose ganglion neurons, including lung afferents in OVA-exposed mice. Cultured nodose ganglion neurons stimulated with capsaicin or IL5 also released VIP while BALF from OVA-exposed mice contained elevated VIP compared to vehicle-challenged mice (Talbot et al., Neuron 2015, in press). These data indicate that VIP is released in the inflamed lung and can be blocked by silencing neurons with charged sodium channel blockers of the present invention. In addition, when CD4+ T cells cultured under $T_H2$ skewing conditions were exposed to recombinant mouse VIP, the transcript levels of IL-13 and IL-5 increased, suggesting that VIP contributes to the competence of $T_H2$ cells to transcribe these type II regulatory cytokines.

Immune mediator release from immune cells can also activate nociceptors. Mast cells are found close to primary nociceptive neurons and contribute to nociceptor sensitization in a number of contexts. Injection of the secretagogue compound 48/80 promotes degranulation of mast cells in the dura and leads to excitation of meningeal nociceptors. Mast cell degranulation also contributes to the rapid onset of nerve growth factor-induced thermal hyperalgesia. Macrophages contribute to nociceptor sensitization by releasing several soluble mediators. Expression of the chemokine macrophage inflammatory protein-1α (MIP-1α) and its receptors CCR1 and CCR5 is increased in macrophages and Schwann cells after partial ligation of the sciatic nerve and contributes to the development of neuropathic pain. Lymphocytes contribute to the sensitization of peripheral nociceptors. T cells infiltrate the sciatic nerve and dorsal root ganglion (DRG) after nerve injury. Hyperalgesia and allodynia induced by nerve injury are markedly attenuated or abrogated in rodents lacking T cells and the immunosuppressant rapamycin attenuates neuropathic pain in rats, partly owing to an effect on T cells. Among the subsets of T cells, type 1 and 2 helper T cells ($T_H1$ and $T_H2$ cells) have been shown to have different roles in neuropathic pain. $T_H1$ cells facilitate neuropathic pain behavior by releasing proinflammatory cytokines (IL-2 and interferon-γ (IFNγ)), whereas $T_H2$ cells inhibit it by releasing anti-inflammatory cytokines (IL-4, IL-10 and IL-13). The complement system also has a role in inflammatory hyperalgesia and neuropathic pain. C5a, an anaphylatoxin, is an important effector of the complement cascade and upon binding to C5aR1 receptors on neutrophils it becomes a potent neutrophil attractant (Ren & Dubner, Nat. Med. 16:1267-1276 (2010)).

Bacterial infections have been shown to directly activate nociceptors, and that the immune response mediated through TLR2, MyD88, T cells, B cells, and neutrophils and monocytes is not necessary for *Staphylococcus aureus*-induced pain in mice (Chiu et al., Nature 501:52-57 (2013)). Mechanical and thermal hyperalgesia in mice is correlated with live bacterial load rather than tissue swelling or immune activation. Bacteria induce calcium flux and action potentials in nociceptor neurons, in part via bacterial N-formylated peptides and the pore-forming toxin α-haemolysin, through distinct mechanisms. Specific ablation of Nav1.8-lineage neurons, which include nociceptors, abrogated pain during bacterial infection, but concurrently increased local immune infiltration and lymphadenopathy of the draining lymph node. Thus, bacterial pathogens produce pain by directly activating sensory neurons that modulate inflammation, an unsuspected role for the nervous system in host-pathogen interactions. Data from Talbot et al., Neuron 2015, in press have also suggested that nociceptors are activated during exposure to allergens in sensitized animals.

In certain disorders, neurogenic inflammation contributes to the peripheral inflammation elicited by tissue injury, autoimmune disease, infection, and exposure to irritants in soft tissue, skin, the respiratory system, joints, the urogenital and GI tract, the liver, and the brain. Neurogenic inflammatory disorders include asthma, rhinitis, conjunctivitis, arthritis, colitis, contact dermatitis, diabetes, eczema, cystitis, gastritis, migraine headache, psoriasis, rhinitis, rosacea, and sunburn. pancreatitis, chronic cough, chronic rhinosinusistis, traumatic brain injury, polymicrobial sepsis, tendinopathies chronic urticaria, rheumatic disease, acute lung injury, exposure to irritants, inhalation of irritants, pollutants, or chemical warfare agents, as described herein.

Assessment of Pain, Itch, and Neurogenic Inflammation

In order to measure the efficacy of any of the methods, compositions, or kits of the invention, a measurement index may be used. Indices that are useful in the methods, compositions, and kits of the invention for the measurement of pain associated with musculoskeletal, immunoinflammatory and neuropathic disorders include a visual analog scale (VAS), a Likert scale, categorical pain scales, descriptors, the Lequesne index, the WOMAC index, and the AUSCAN index, each of which is well known in the art. Such indices may be used to measure pain, itch, function, stiffness, or other variables.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., in U.S. Pat. Nos. 6,709,406 and 6,432,937.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., in U.S. Pat. Nos. 6,623,040 and 6,766,319.

The Lequesne index and the Western Ontario and McMaster Universities (WOMAC) osteoarthritis index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert. Both the WOMAC index and the Lequesne index questionnaires have been extensively validated in OA, including in surgical settings (e.g., knee and hip arthroplasty). Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

Indices that are useful in the methods, compositions, and kits of the invention for the measurement of pain include the Pain Descriptor Scale (PDS), the Visual Analog Scale (VAS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

Itch can be measured by subjective measures (VAS, Lickert, descriptors). Another approach is to measure scratch which is an objective correlate of itch using a vibration transducer or movement-sensitive meters.

The following examples are intended to illustrate the invention, and is not intended to limit it.

EXAMPLES

Experimental Methods
In Vitro Electrophysiology

Whole-cell recordings were made of currents carried by voltage-activated channels in HEK293 cells stably expressing human Nav1.7 channels. Recordings were made using patch pipettes with resistances of 2-3.5 MO when filled with internal solution, consisting of 61 mM CsF, 61 mM CsCl, 9 mM NaCl, 1.8 mM $MgCl_2$, 9 mM EGTA, 14 mM creatine phosphate (tris salt), 4 mM MgATP, and 0.3 mM GTP (tris salt), 9 mM HEPES, pH adjusted to 7.2 with CsOH. The shank of the electrode was wrapped with Parafilm in order to reduce capacitance and allow optimal series resistance compensation without oscillation. Seals were obtained and the whole-cell configuration established with cells in Tyrode's solution (155 mM NaCl, 3.5 mM KCl, 1.5 mM $CaCl_2$, 1 mM $MgCl_2$, 10 mM HEPES, 10 mM glucose, pH adjusted to 7.4 with NaOH) with 10 mM TEACl. To ensure complete dialysis with pipette solution, recordings began after 5 to 10 min after establishment of the whole-cell configuration.

Currents were recorded at room temperature (21-23° C.) with an Axopatch 200 amplifier and filtered at 5 kHz with a low-pass Bessel filter. The amplifier was tuned for partial compensation of series resistance (typically 70-80% of a total series resistance of 4-10 MΩ). Currents were digitized using a Digidata 1322A data acquisition interface controlled by pClamp9.2 software (Axon Instruments) and analyzed using programs written in Igor Pro 4.0 (Wavemetrics, Lake Oswego, Oreg.). Currents were corrected for linear capacitative and leak currents determined using 5 mV hyperpolarizations delivered from the resting potential (usually −80 or −100 mV) and then appropriately scaled and subtracted.

Sodium currents were evoked by 30-msec depolarizations from −100 mV to −20 mV. To assay use-dependent block, pulses were delivered at series of increasing rates: 0.05 Hz for 1-min, 0.33 Hz for 1-min, 1 Hz for 1-min, 3 Hz for 1-min, 5 Hz for 30 seconds, 10 Hz for 30 seconds, with 1 minute rest between each series of pulses. After the series of pulses to induce use-dependent block, the time course of recovery was followed using pulses delivered at 01. Hz (2-min) and 0.05 Hz (1-min).

Animals

Figure 3A:
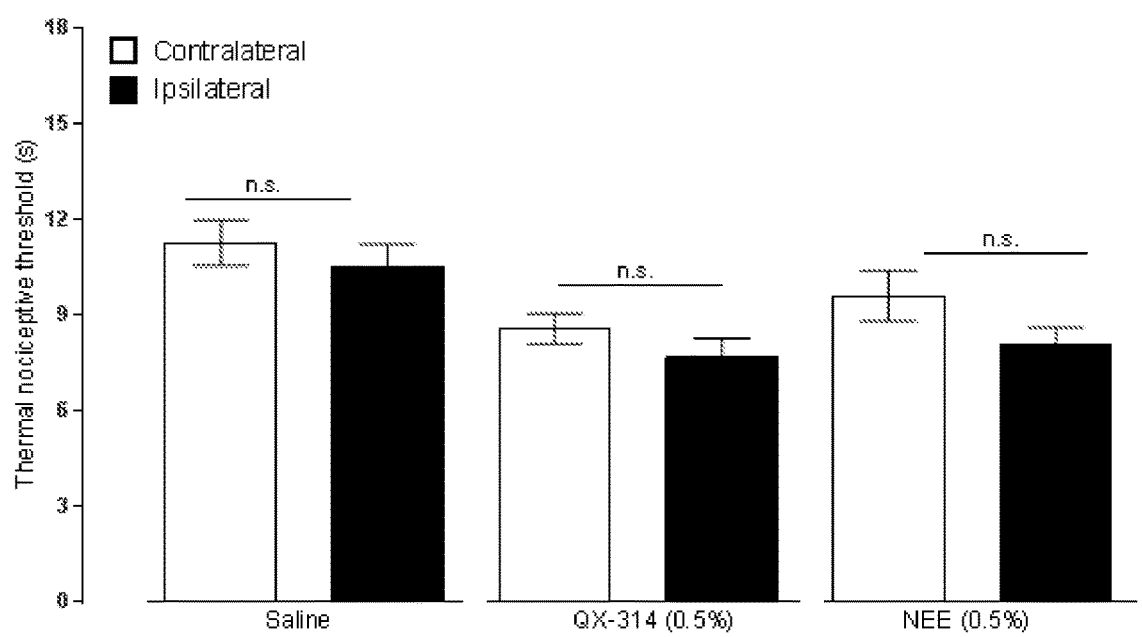
FIGS. 3A-3B are data showing reversal of paw incision-induced thermal hyperalgesia by charged sodium channel blockers.

All procedures were approved by the Institutional Animal Care and Use Committees. Mice and rats were housed in standard environmental conditions (12-h light/dark cycle; 23° C.; food and water ad libitum) at facilities accredited by the Association for Assessment and Accreditation of Laboratory Animal Care. 8-week old male BALB/c (stock number: 001026) and C57BL/6J (stock number 000664) mice were purchased from Jackson Laboratory and respectively used in allergic airway inflammation (FIG. 5) and pain hypersensitivity model (FIGS. 2A-2D). 6-week old male Sprague-Dawley (stock number: 400) rats, 150±25 grams, were purchased from Charles River laboratory and used to assess pain hypersensitivity (FIG. 3).

Immunofluorescence

Upon harvesting, the dorsal root ganglia were fixed overnight in 4% para-formaldehyde, washed in PBS and cryo-protected by sequential sucrose immersion (PBS 10-30% sucrose, Overnight). Ganglia were mounted in O.C.T. (Tissue-tek), and serially cut in 20 μm coronal sections with a cryostat. The sections were thaw-mounted on Fisherbrand superfrost microscopy slides and kept at −80° C. On the day of the experiment, sections were thawed at room temperature for 10 min. Sections were washed in PBS for 5 min, blocked for 1 h at room temperature (PBS, 0.1% Triton X-100, 5% BSA) and exposed to the primary antibodies (Overnight, 4° C.), namely rabbit anti-mouse ATF3 (Sigma, #HPA001562). Sections were then washed three times in PBS (5 min), exposed to the secondary antibodies and DAPI (1:2000. Sigma, #D9542) (2 h, dark), washed, coverslipped with Vectashield (Vector Labs) and observed under confocal microscope (Leica, LSM-710).

Ovalbumin Sensitization and Airway Challenge

Allergic airway inflammation was studied in an ovalbumin (OVA) based model. On day 0 and 7, mice were sensitized by a 200 μl i.p. injections of a solution containing 1 mg/ml ovalbumin (Sigma-Aldrich) and 5 mg/ml aluminum hydroxide (Sigma-Aldrich, Boston, Ma). On day 14-17 (10:00 am) mice were exposed to 6% OVA aerosol for 25 min to induce airways allergic inflammation. Drugs were nebulized on day 18 (10:00 am) and inflammation (BALF cell content)/airway hyper-responsiveness were assessed on day 21 (10:00 am).

Bronchoalveolar Lavage (BAL)

On day 21, mice were anesthetized following an intraperitoneal injection of urethane (dose) and a 20G sterile catheter inserted longitudinally into the trachea. 2 ml of ice cold PBS containing protease inhibitors (Roche) was injected into the lung, harvested and stored on ice. BAL fluid underwent a 400 g centrifugation (15 min; 4° C.), the supernatant was discarded and cells re-suspended in 200 μl.

Airway Inflammatory and Differential Cell Count

Bronchoalveolar lavage fluid (BALF) cells were re-suspended in FACS buffer (PBS, 2% FCS, EDTA), and incubated with Fc block (0.5 mg/ml, 10 min; BD Biosciences). Cells were then stained with monoclonal antibodies (FITC anti-mouse CD45, BD Biosciences, cat no: 553079; PE anti-mouse Syglec-F, BD Biosciences, cat no: 552126; APC anti-mouse GR-1, eBiosciences, cat no: 17-5931-81; PE-Cy7 anti-mouse CD3e, cat no: 25-0031-81; PerCP anti-mouse F4/80, BioLegend, cat no: 123125; PE anti-mouse, BD Bioscience, cat no: 552126; 45 min, 4° C. on ice) before data acquisition on a FACS Canto II (BD Biosciences). A leukocyte differential count was determined during flow cytometry analysis of cells expressing the common leukocyte antigen CD45 (BD Pharmigen; cat no: 553079). Specific cell populations were identified as follows: macrophages as F4/80Hi-Ly6 gNeg, eosinopohils as F4/80Int-Ly6 gLo-SiglecFHi, neutrophils as F4/80Lo-Ly6 gHi-SiglecFNeg, and lymphocytes as F4/80Neg-Ly6 gNeg-CD3Pos. Total BAL cell counts were performed using a standard hemocytometer, with absolute cell numbers calculated as total BAL cell number multiplied by the percentage of cell subpopulation as determined by FACS.

Thermal Hypersensitivity

The compounds were injected in the plantar surface of each animal's right hind paw in 10 μl (mice) or 50 μl (rats) volume of 1:1 emulsion of Complete Freund's Adjuvant (CFA). Thermal hyperalgesia was examined by measuring the latency to withdrawal of the hind paws from a focused beam of radiant heat applied to the plantar surface using a Ugo Basile Plantar Test (Hargreaves) apparatus. For 3 consecutive days, 8 weeks old Sprague Dawley male rat will be habituated for 60 min on the Hargreaves apparatus. On the 4th day, their thermal nociceptive threshold was evaluated. 1 h later, the rats were lightly anesthetized under isoflurane (3% induction, 2% maintenance) and received an intraplantar injection of CFA in the presence or not of the test compounds. Impact of treatment was analyzed 1 h prior and 1, 3, 6 and 24 h post-treatment. Three trials were performed on each paw, by alternating the starting paw, with an interval of 5 minutes. A positive pain reaction was defined as sudden paw withdrawal, flinching, and/or paw licking. With each reading the apparatus was set with a cut-off time of 32 s.

Example 1. Synthesis of 1-(1-(2,6-dimethylphenylamino)-1-oxopropan-2-yl)-1-methylpyrrolidinium chloride (Compound 1)

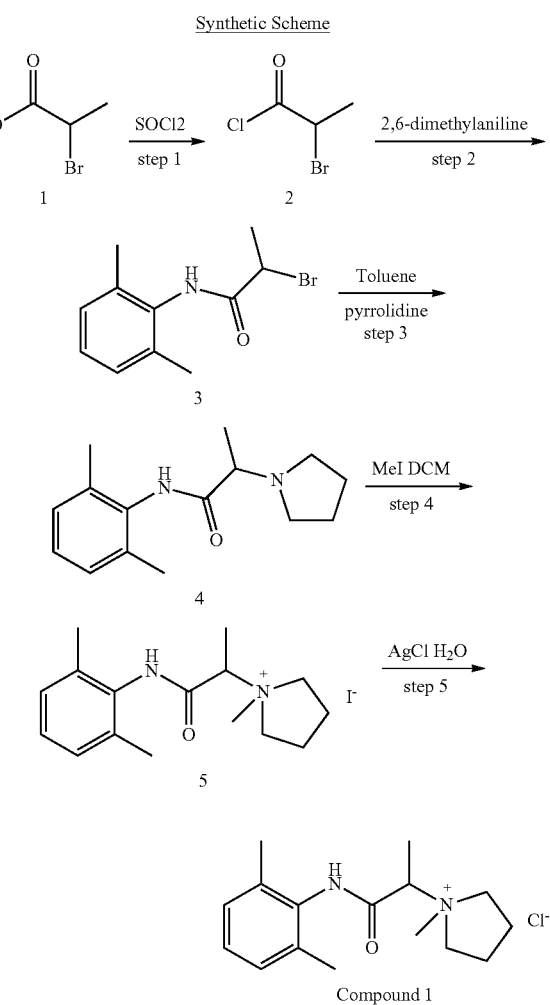

Step 1: Preparation of 2

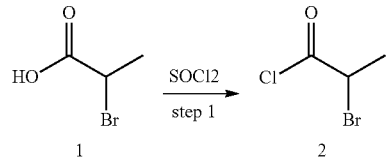

The solution of 1 (5.0 g, 32.86 mmol, 1.0 eq) in 30 mL SOCl$_2$ was refluxed at 8° C. for 2 h. After competition, the reaction mixture was directly concentrated in vacuum to give a residue without further purification (7.8 g, y=120%).

Step 2: Preparation of 3

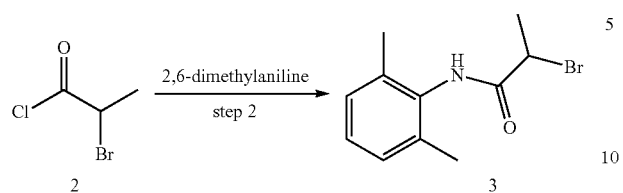

To a solution of 2,6-dimethylaniline (4.6 g, 38.2 mmol, 1.0 eq) in DCM (10 mL) and TEA (4.6 g, 45.8 mmol, 1.2 eq) was added 2 (7.8 g, 45.8 mmol, 1.2 eq) in DCM (20 mL) slowly at ice bath. Then the reaction mixture was warmed to R.T. for 2 h. After competition, the reaction mixture was adjusted to pH=5-6 with 2N HCl, extracted with EA (150 mL×2). The combined organic phases was washed with brine (100 mL), dried over $Na_2SO_4$, filtered and concentrated in vacuum to give a residue. The residue was purified by column chromatography to give the desired product (4.8 g, 50% yield) as gray solid.

Step 3: Preparation of 4

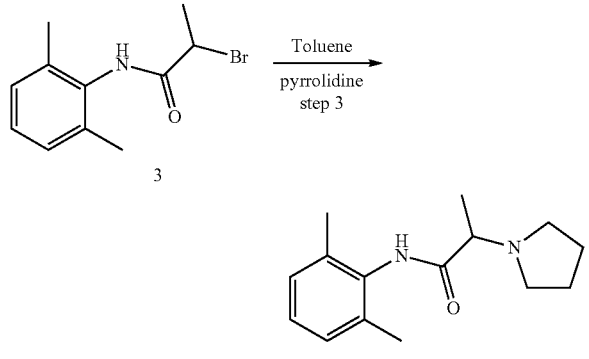

To a solution of 3 (2 g, 7.68 mmol, 1.0 eq) in Toluene (15 mL, c=0.5) was added pyrrolidine (1.17 g, 16.5 mmol, 2.0 eq). The reaction mixture was refluxed at 110° C. for 30 min. After competition, the reaction mixture was directly concentrated in vacuum to give a residue. The residue was purified by column chromatography to give the desired product (1.8 g, 95% yield) as yellow oil.

Step 4: Preparation of 5

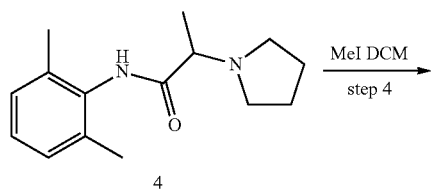

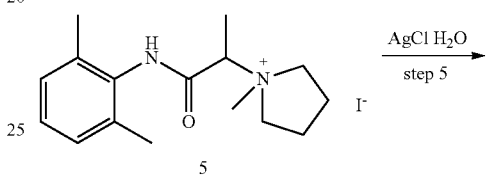

To a solution of 4 (500 mg, 2.03 mmol, 1.0 eq) in DCM (20 mL, c=0.1) was added MeI (721 mg, 5.08 mmol, 2.5 eq) at R.T. overnight. The reaction mixture was directly concentrated in vacuum to give a residue. The residue was washed with EA to give desired product (233 mg, 30% yield).

Step 5: Preparation of Compound 1

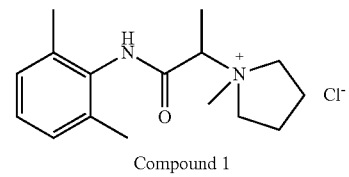

To a solution of 5 (233 mg, 0.602 mmol, 1.0 eq) in $H_2O$ (1.6 mL, c=0.37) was added AgCl (172 mg, 2.0 eq). The reaction mixture was heated at 60° C. overnight. After competition, the reaction mixture was filtered. The filtrate was lyophilized to give desired product. (62 mg, 35% yield) as white solid. $^1$H NMR (300 MHz, DMSO): δ 7.18~7.09 (m, 3H), 4.31 (q, J=7.2 Hz, 1H), 3.65~3.57 (m, 4H), 3.16 (s, 3H), 2.15~2.25 (m, 4H), 2.08 (s, 6H), 1.74 (d, J=6.9 Hz, 3H) ppm. HPLC purity: 100% at 220 nm; Mass: m/z=261.5 (M+1, ESI+).

Example 2. Synthesis of 1-(1-(2,6-dimethylphenylamino)-2-methyl-1-oxopropan-2-yl)-1-methylpyrrolidinium chloride (Compound 2)

Synthetic Scheme

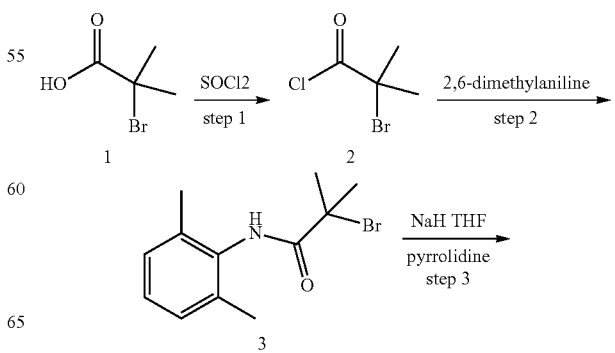

Step 3: Preparation of 4

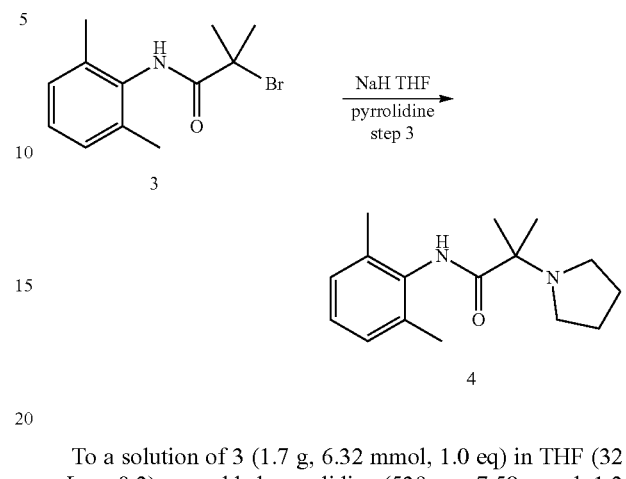

To a solution of 3 (1.7 g, 6.32 mmol, 1.0 eq) in THF (32 mL, c=0.2) was added pyrrolidine (539 mg, 7.58 mmol, 1.2 eq) and NaH (303 mg, 12.64 mmol, 2.0 eq) in THF (32 mL, c=0.2). The reaction mixture was stirred at R.T. for 30 min. After competition, 30 mL $H_2O$ was added slowly, extracted with EA (50 mL×2). The combined organic phases was washed with brine (30 mL), dried over $Na_2SO_4$, filtered and concentrated in vacuum to give a residue. The residue was purified by column chromatography to give the desired product (680 g, 68% yield) as white solid.

Step 1: Preparation of 2

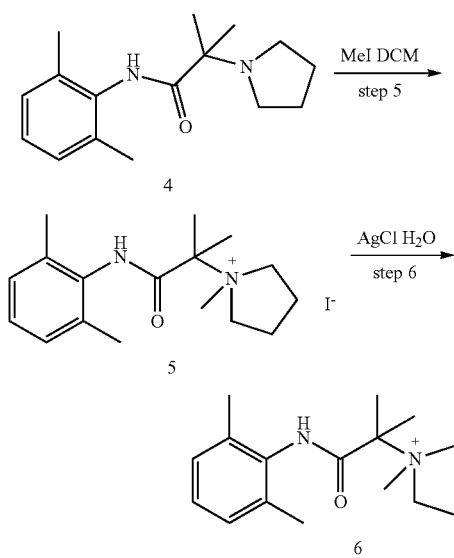

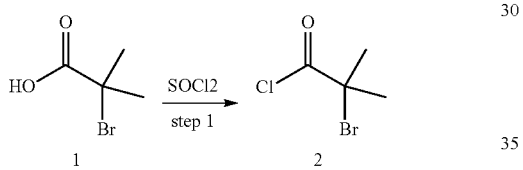

The solution of 1 (10.0 g, 59.88 mmol, 1.0 eq) in 60 mL $SOCl_2$ was refluxed at 80° C. for 2 h. After competition, the reaction mixture was directly concentrated in vacuum to give a residue without further purification (15.0 g, y=132%).

Step 2: Preparation of 3

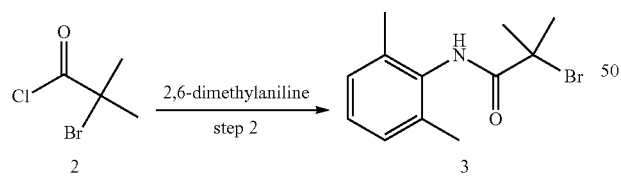

To a solution of 2,6-dimethylaniline (8.16 g, 67.38 mmol, 1.0 eq) in DCM (50 mL) and TEA (8.18 g, 80.86 mmol, 1.2 eq) was added 2 (15.0 g, 80.86 mmol, 1.2 eq) in DCM (50 mL) slowly at ice bath. Then the reaction mixture was warmed to R.T. for 2 h. After competition, the reaction mixture was adjusted to pH=5-6 with 2N HCl, extracted with EA (200 mL×2). The combined organic phases was washed with brine (150 mL), dried over $Na_2SO_4$, filtered and concentrated in vacuum to give a residue. The residue was purified by column chromatography to give the desired product (14.8 g, 82% yield) as solid.

Step 4: Preparation of 5

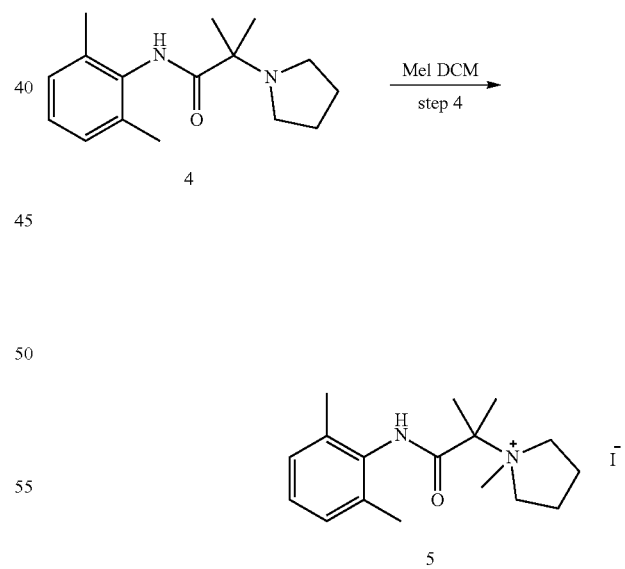

To a solution of 4 (150 mg, 0.577 mmol, 1.0 eq) in MeCN (5.7 mL, c=0.1) was added MeI (245 mg, 1.73 mmol, 3.0 eq). The reaction mixture was refluxed overnight. After competition, the reaction mixture was directly concentrated in vacuum to give a residue. The residue was washed with EA to give desired product (170 mg, 73% yield) as white solid.

Step 5: Preparation of 6

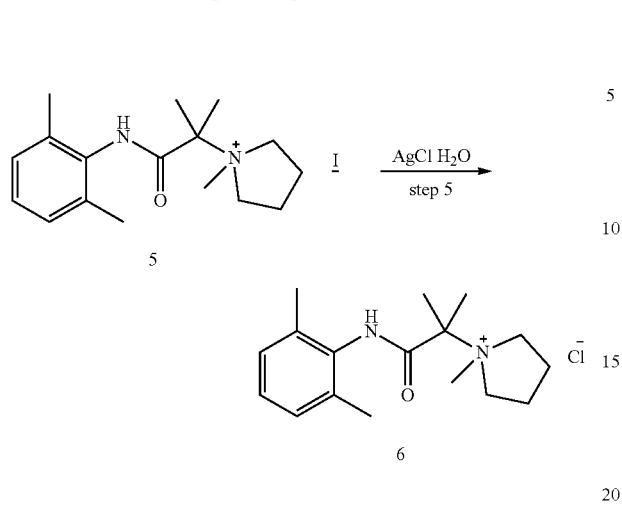

To a solution of 5 (170 mg, 0.423 mmol, 1.0 eq) in H₂O (1.4 mL, c=0.3) was added AgCl (121 mg, 2.0 eq). The reaction mixture was heated at 60° C. overnight. After competition, the reaction mixture was filtered. The filtrate was lyophilized to give desired product. (82 mg, 63% yield) as white solid. $^1$H NMR (300 MHz, DMSO): δ 7.15~7.09 (m, 3H), 3.95~3.85 (m, 2H), 3.53~3.49 (m, 2H), 3.11 (s, 3H), 2.11~2.10 (m, 4H), 2.08 (s, 6H), 1.85 (s, 6H) ppm. HPLC purity: 95.6% at 220 nm; Mass: m/z=261.5 (M+1, ESI+).

Example 3. Synthesis of 1-(1-(2,6-dimethylphenylamino)-1-oxobutan-2-yl)-1-ethylpyrrolidinium chloride (Compound 3)

Synthetic Scheme

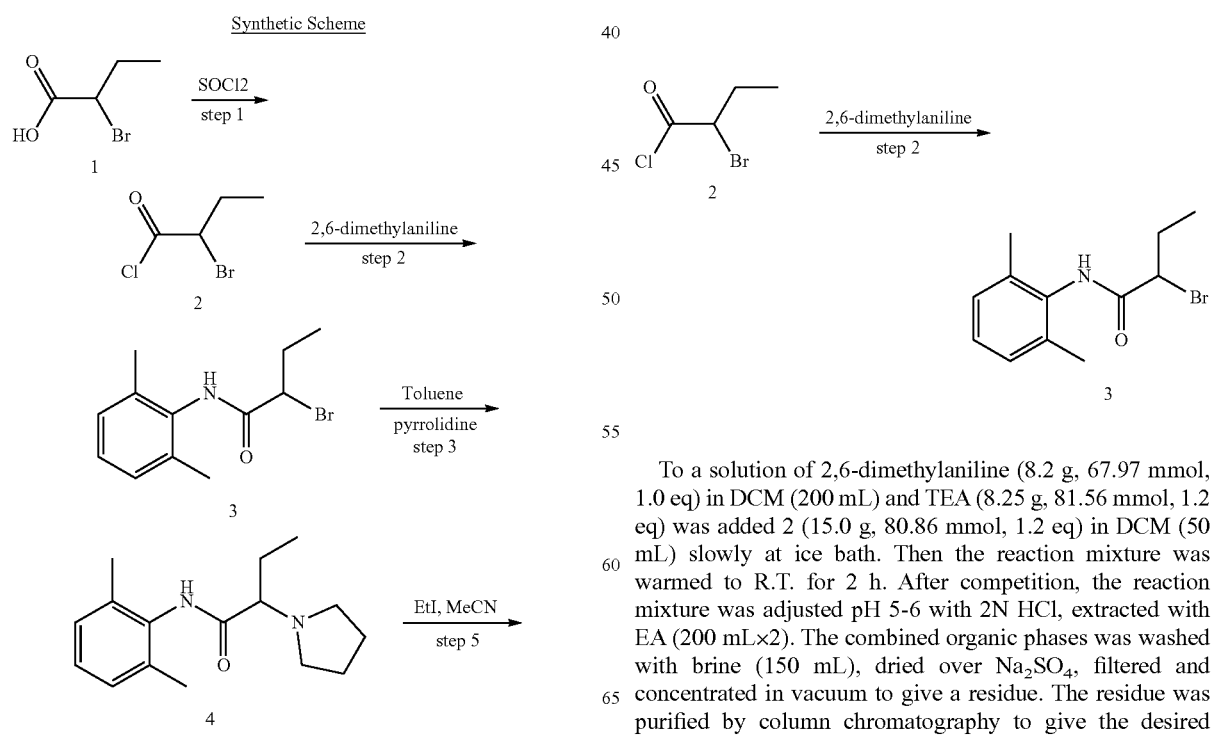

Step 1: Preparation of 2

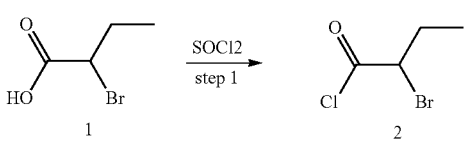

The solution of 1 (10.0 g, 60.2 mmol, 1.0 eq) in 60 mL SOCl₂ was refluxed at 80° C. for 2 h. After competition, the reaction mixture was directly concentrated in vacuum to give a residue without further purification (15.0 g, y=132%).

Step 2: Preparation of 3

To a solution of 2,6-dimethylaniline (8.2 g, 67.97 mmol, 1.0 eq) in DCM (200 mL) and TEA (8.25 g, 81.56 mmol, 1.2 eq) was added 2 (15.0 g, 80.86 mmol, 1.2 eq) in DCM (50 mL) slowly at ice bath. Then the reaction mixture was warmed to R.T. for 2 h. After competition, the reaction mixture was adjusted pH 5-6 with 2N HCl, extracted with EA (200 mL×2). The combined organic phases was washed with brine (150 mL), dried over Na₂SO₄, filtered and concentrated in vacuum to give a residue. The residue was purified by column chromatography to give the desired product (3.0 g, 17% yield) as solid.

Step 3: Preparation of 4

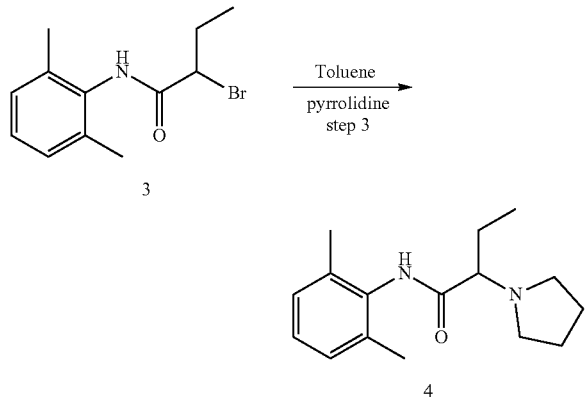

To a solution of 3 (3.0 g, 11.15 mmol, 1.0 eq) in Toluene (22 mL, c=0.5) was added pyrrolidine (1.66 g, 23.42 mmol, 1.2 eq). The reaction mixture was refluxed at 110° C. for 3 h. After competition, the reaction mixture was directly concentrated in vacuum to give a residue. The residue was purified by column chromatography to give the desired product (1.2 g, 41% yield) as white solid.

Step 4: Preparation of 5

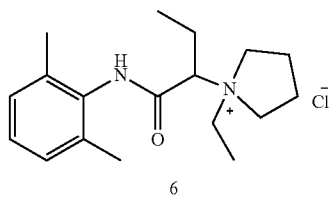

To a solution of 4 (500 mg, 1.921 mmol, 1.0 eq) in MeCN (20 mL, c=0.1) was added EtI (749 mg, 4.802 mmol, 2.5 eq). The reaction mixture was refluxed overnight. After competition, the reaction mixture was directly concentrated in vacuum to give a residue. The residue was washed with EA to give desired product (423 mg, 50% yield) as white solid.

Step 5: Preparation of 6

To a solution of 5 (423 mg, 1.016 mmol, 1.0 eq) in H$_2$O (4 mL, c=0.3) was added AgCl (291 mg, 2.033 mmol, 2.0 eq). The reaction mixture was heated at 60° C. overnight. After competition, the reaction mixture was filtered. The filtrate was lyophilized to give desired product. (83 mg, 63% yield) as white solid. $^1$H NMR (300 MHz, DMSO): δ 10.30 (br, 1H), 7.26~7.19 (m, 3H), 4.23 (q, J=6.15, 1H), 3.95~3.80 (d, J=3.12, 2H), 3.7~03.55 (m, 4H), 3.22 (s, 6H), 2.15~2.11 (m, 6H), 1.47~1.44 (d, J=4.23, 3H), 1.22~1.19 (d, J=4.40, 3H) ppm. HPLC purity: 98% at 220 nm; Mass: m/z=289.5 (M+1, ESI+).

Example 4. Synthesis of 1-(1-(2,6-dimethylphenylamino)-1-oxopropan-2-yl)-1-methylpiperidinium chloride (Compound 4)

Synthetic Scheme

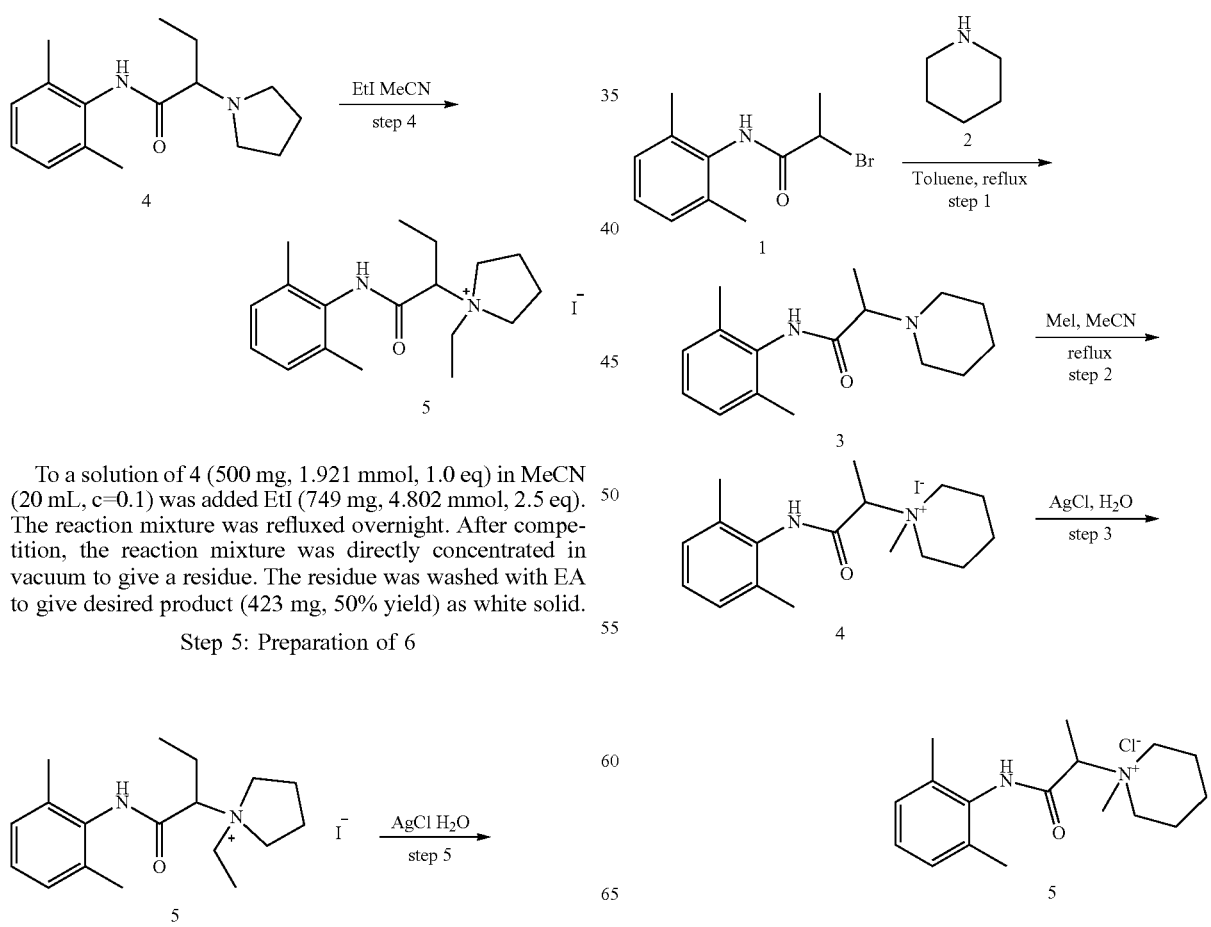

Step 1: Preparation of 3

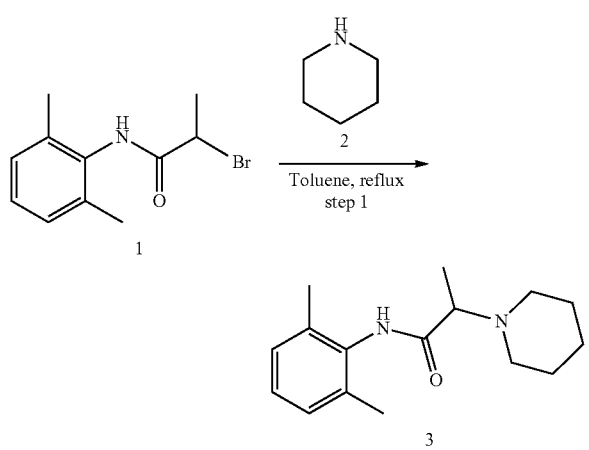

To a solution of 1 (0.5 g, 1.95 mmol, 1.0 eq) in Toluene (10 ml, c=0.2) was added 2 (0.35 g, 4.1 mmol, 2.1 eq). After addition, the mixture was heated to reflux. After completion, the suspension was filtered and the filtrate was concentrated under reduce pressure. The residue was purified by column chromatography to give the desired product (0.4 g, yield=78.9%) as a solid.

Step 2: Preparation of 4

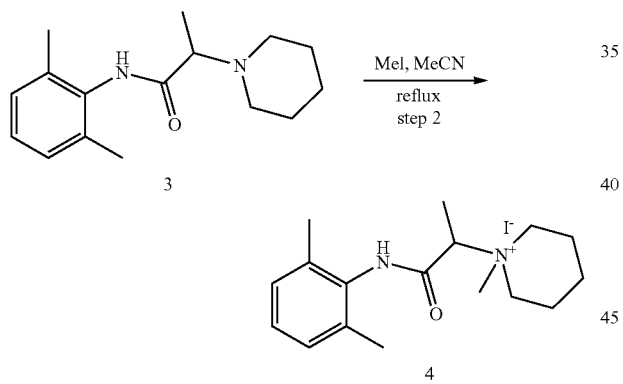

To a solution of 3 (162 mg, 0.62 mmol, 1.0 eq) in MeCN (6 mL, c=0.1) was added MeI (220 mg, 2.5 eq). After addition, the reaction mixture was heated to reflux for 5 h. After completion, the reaction solution was concentrated under reduce pressure to give the product (184 mg, yield=73.8%, HPLC: 93%) as a solid.

Step 3: Preparation of 5

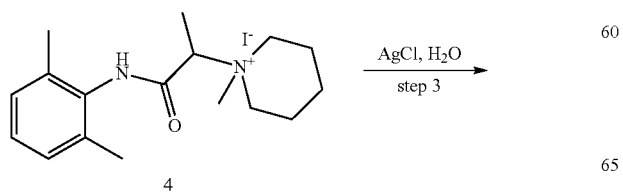

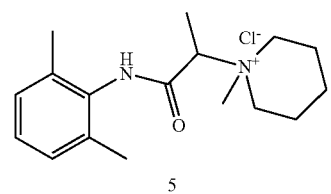

To a solution of 4 (122.7 mg, 0.3 mmol, 1.0 eq) in deionized water (2 ml, c=0.15) was added AgCl (86 mg, 2.0 eq). After addition, the reaction mixture was stirred at 60° C. overnight. After completion, the suspension was filtered and the filtrate was used lyophilization to give the product (89.6 mg, yield=96.1%) as a solid. HPLC purity: 95% at 220 nm; Mass: $M_+$: M−35.5=275.5; 2M−35.5=585.8; M−: M=310.5; M+35.5=345.5. $^1$H NMR (500 MHz, $D_2O$): δ 7.1400~7.1981 (m; 3H), 4.4345 (s; 1H), 3.6625 (s; 1H), 3.5410 (s; 1H), 3.4610 (s; 2H), 3.2348 (s; 3H), 2.1289 (s; 6H), 1.9253 (d, J=28.3 Hz, 4H), 1.7403 (t, 4H), 1.6225 (s; 1H). ppm.

Example 5. Synthesis of 1-(1-(2,6-dimethylphenylamino)-2-methyl-1-oxopropan-2-yl)-1-methylpiperidinium chloride (Compound 5)

Synthetic Scheme

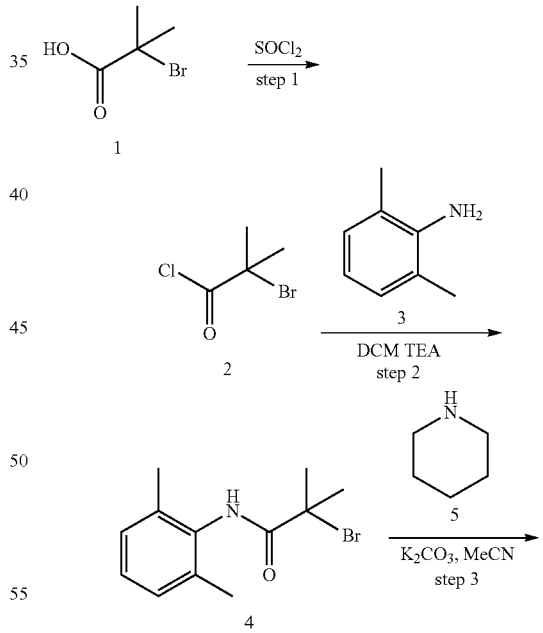

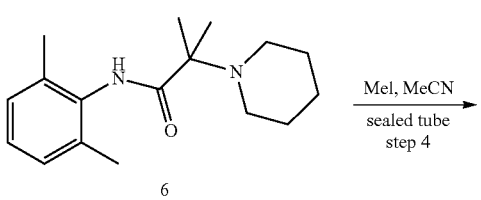

49

-continued

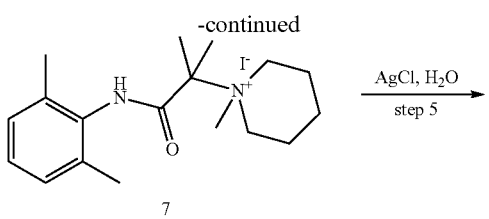

Step 1: Preparation of 2

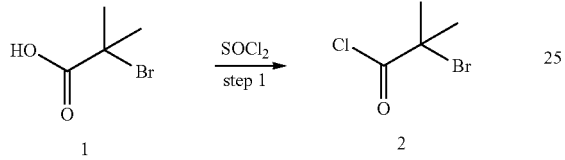

To a mixture of 1 (10.0 g, 59.88 mmol) was added SOCl₂ (60 ml, c=1.0). The mixture was heated to reflux. After completion, the reaction mixture was concentrated under reduce pressure to give the desired product (14.8 g, yield=128.8%) as a yellow oil.

Step 2: Preparation of 4

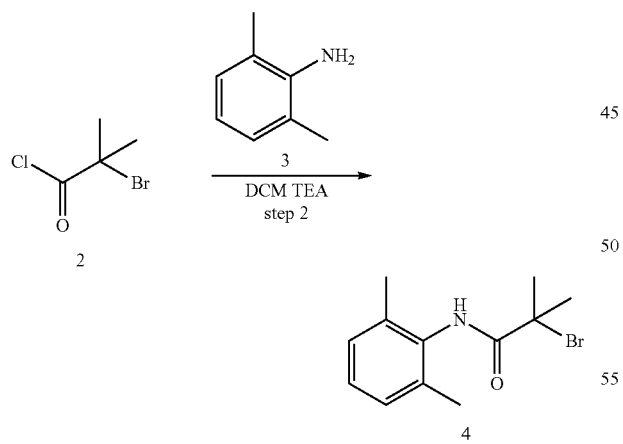

To a mixture of 3 (6.0 g, 50 mmol, 1.0 eq) in DCM (100 ml, c=0.5) was added TEA (10.1 g, 100 mmol, 2 eq). Then the solution was added 2 (14.3 g, 77.1 mmol, 1.5 eq) in DCM (50 ml, c=1). The reaction mixture was stirred at RT. over night. Then the mixture was added water (60 ml) to stratify. The organic phases was washed with brine, dried over Na₂SO₄, filtered and concentrated under reduce pressure. The residue was purified by column chromatography

50 and the cross sample was washed with n-hexane. Combine the solid to give the product (5.7 g, yield=42.2%, HPLC: 99.5%).

Step 3: Preparation of 6

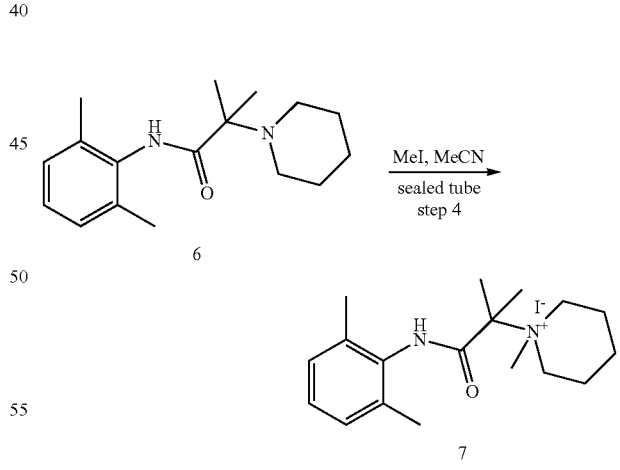

To a solution of 4 (5.3 g, 19.6 mmol, 1.0 eq) and K₂CO₃ (2.7 g, 19.6 mmol, 1.0 eq) in MeCN (98 ml, c=0.2) was added 5 (2.5 g, 29.4 mmol, 1.5 eq). After addition, the mixture was heated to reflux. After completion, the suspension was filtered and the filtrate was concentrated under reduce pressure. The residue was purified by column chromatography to give the desired product (1.7 g, yield=31.6%, HPLC: 96.4%) as a solid.

Step 4: Preparation of 7

6 (1.6 g, 5.8 mmol, 1.0 eq) and MeCN (30 mL, c=0.2) was added in sealed tube. To this solution, MeI (5 mL, 14.0 eq) was added. After addition, the reaction mixture was stirred at 90° C. for 32 h. After completion, the reaction solution was concentrated under reduce pressure. The residue was purified by column chromatography and washed with EA (5 ml×2) to give the product (557 mg, yield=23%, HPLC: 99.6%) as a solid.

Step 4: Preparation of 8

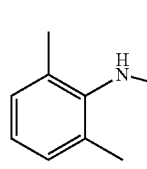

To a solution of 7 (200 mg, 0.48 mmol, 1.0 eq) in deionized water (4 ml, c=0.12) was added AgCl (137.8 mg, 2.0 eq). After addition, the reaction mixture was stirred at RT for 6 h. After completion, the suspension was filtered and the filtrate was used lyophilization to give the product (152 mg, yield=97%) as a solid. HPLC purity: 100% at 220 nm; Mass: M+: M−35.5=289.5; 2M−35.5=613.8; $^1$H NMR (500 MHz, D$_2$O): δ 7.0842~7.1578 (m, 3H), 3.5323 (d, J=7.85 Hz, 4H), 3.1250 (s, 3H), 2.0620 (s, 6H), 1.9314 (m, 2H), 1.7323~1.8119 (m, 9H), 1.3277~1.3543 (m, 2H) ppm.

Example 6. Synthesis of 1-(1-(2,6-dimethylphenylamino)-1-oxobutan-2-yl)-1-ethylpiperidinium (Compound 6)

Synthetic Scheme

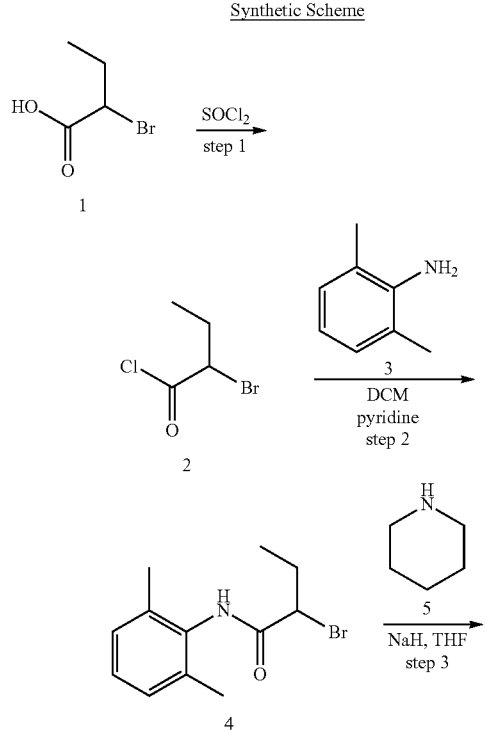

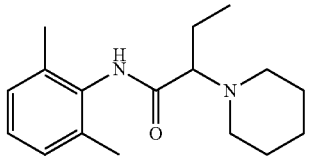

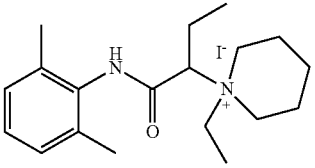

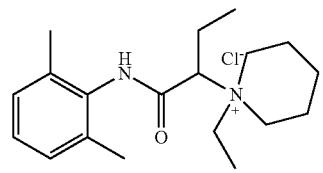

Step 1: Preparation of 2

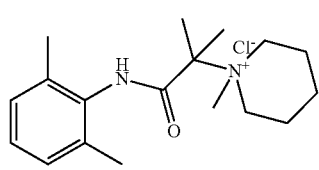

To a mixture of 1 (10.0 g, 59.88 mmol) was added SOCl$_2$ (60 mL, c=1.0). The mixture was heated to reflux. After completion, the reaction mixture was concentrated under reduce pressure to give the desired product (9.2 g, yield=82.8%) as a yellow oil.

Step 2: Preparation of 4

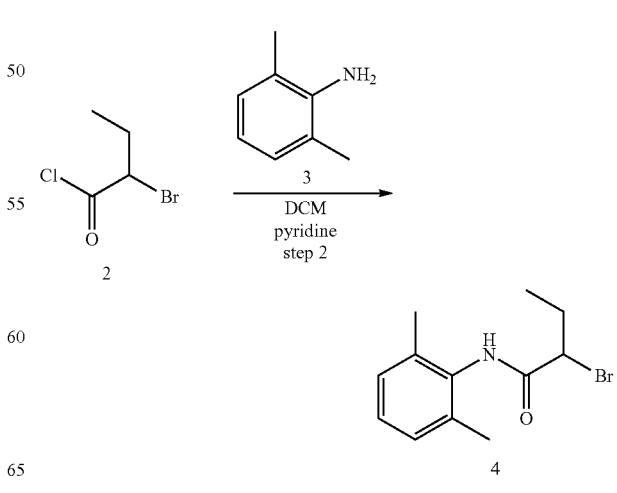

To a mixture of 3 (5.0 g, 41.3 mmol, 1.0 eq) in DCM (100 ml, c=0.5) was added pyridine (4.9 g, 61.95 mmol, 1.5 eq). Then the solution was added 2 (9.2 g, 49.59 mmol, 1.2 eq) in DCM (40 ml, c=1.2). The reaction mixture was stirred at room temperature overnight. Then the solution was added water (50 ml) to stratify. The organic phase was washed with brine, dried over $Na_2SO_4$, filtered and concentrated under reduce pressure. The residue was washed with n-hexane. Combine the solid to give the product (7.8 g, yield=70%, HPLC: 98.6%).

Step 3: Preparation of 6

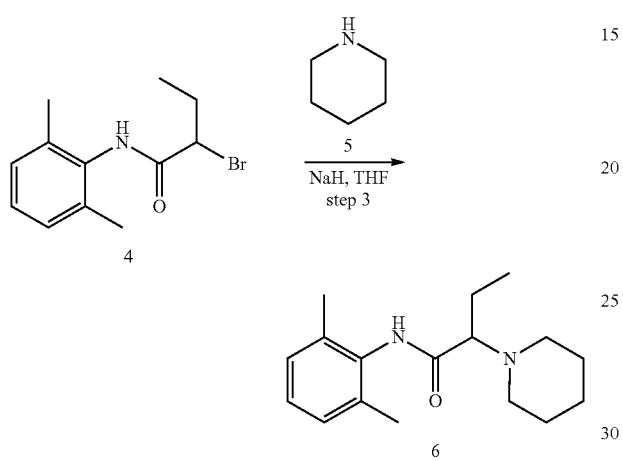

To a solution of NaH (0.35 g, 14.8 mmol, 2.0 eq) in THF (37 mL, c=0.4) was added 5 (0.75 g, 8.8 mmol, 1.2 eq). Then the solution was added 4 (2.0 g, 7.4 mmol, 1.0 eq) in THF (20 mL, c=0.37). After addition, the mixture was stirred at room temperature overnight. After completion, the suspension was added water (20 mL) and EA (50 mL) to stratify. The organic phases were washed with water (50 mL×2). Then the organic phase was adjusted pH to 2, extracted with EA (40 mL×2). The water phases were adjusted pH to 9, then extracted with EA (40×2). The combined organic phases was washed with brine, dried over $Na_2SO_4$, filtered and concentrated under reduce pressure. The residue was washed with n-hexane to give the desired product (0.48 g, yield=24%, HPLC: 99.3%) as a solid.

Step 4: Preparation of 7

6 (0.48 g, 1.75 mmol, 1.0 eq) and MeCN (9 mL, c=0.2) was added in sealed tube. To this solution, EtI (2 mL, 14.0 eq) was added. After addition, the reaction mixture was stirred at 90° C. for 10 h. After completion, the reaction solution was concentrated under reduce pressure. The residue was purified by column chromatography to give the product (470 mg, yield=62.6%, HPLC: 99%) as a solid.

Step 4: Preparation of 8

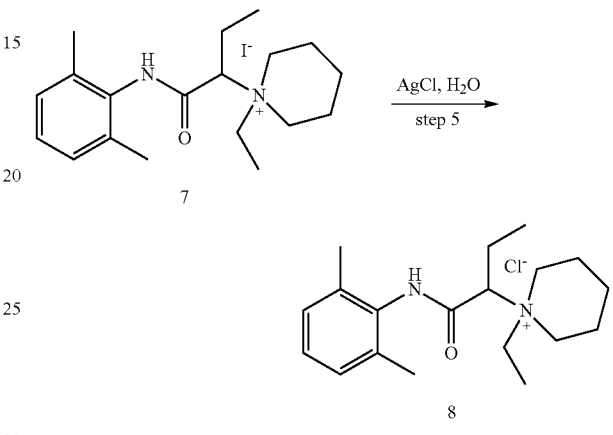

To a solution of 7 (200 mg, 0.465 mmol, 1.0 eq) in deionized water (3 ml, c=0.15) was added AgCl (133 mg, 0.93 mmol, 2.0 eq). After addition, the reaction mixture was stirred at room temperature overnight. After completion, the suspension was filtered and the filtrate was used lyophilization to give the product (141 mg, yield=89.8%) as a solid. HPLC purity: at 220 nm; Mass: M+1=339.4. $^1$H NMR (300 MHz, $D_2O$): δ 7.117 (m, 3H), 4.056 (dd, J=8.1 Hz, 1H), 3.712~3.808 (m, 1H), 3.656 (m, J=13.2 Hz, 2H), 3.510~3.582 (m, 1H), 3.344 (m, 2H), 2.117 (s, 6H), 1.984~2.070 (m, 2H), 1.818 (m, 4H), 1.660 (m, 1H), 1.455 (m, 1H), 1.278 (t, J=7.2 Hz, 3H), 1.107 (t, 3H) ppm.

Example 7. Synthesis of 2-(2,6-dimethylphenylcarbamoyl)-1,1-dimethylpyrrolidinium chloride (Compound 13)

Synthetic Scheme

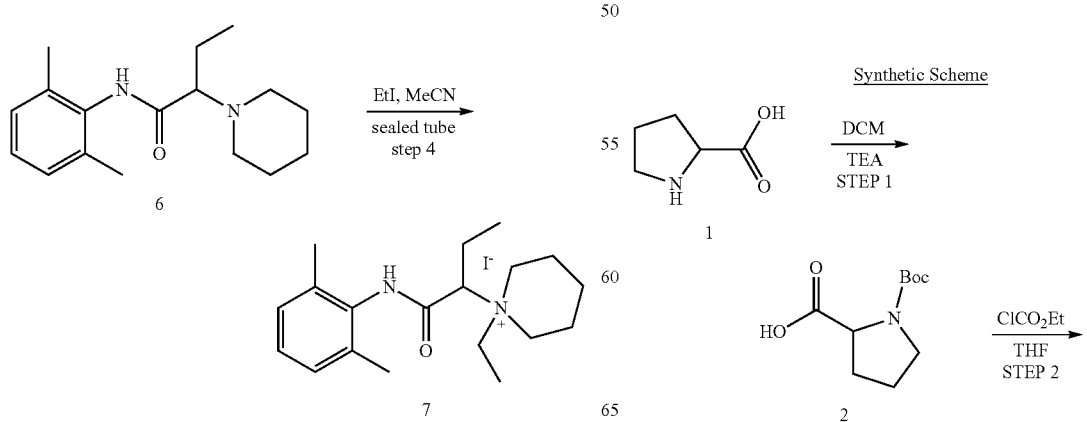

-continued

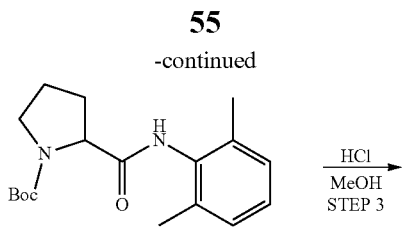

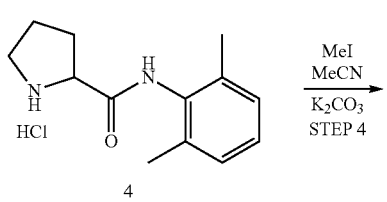

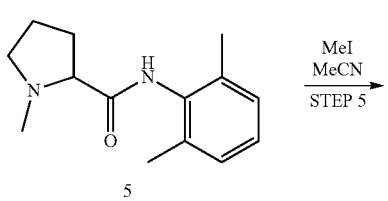

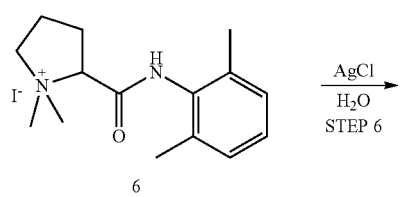

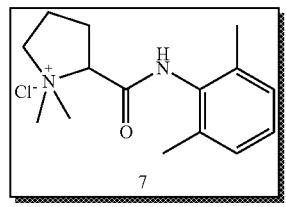

Step 1: Preparation of 2

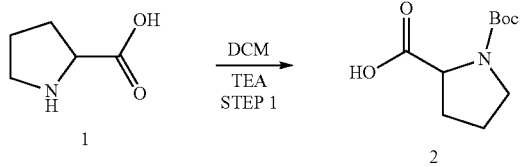 [SMILES: O=C(O)C1CCCN1 ; CC(C)(C)OC(=O)N1CCCC1C(=O)O]

To a mixture of 1 (10 g, 86.9 mmol, 1 eq) in DCM (189 mL, c=0.46) was added TEA (35.2 g, 347.6 mmol, 4 eq) and then dropwise (Boc)₂O (12.57 g, 99.03 mmol, 1.2 eq) at 0° C. After addition, the reaction mixture was warmed slowly to room temperature and stirred for 3 h. The reaction mixture was directed concentrated in vacuum to get a residue without further purification (18 g, 98.36% yield) as white oil.

Step 2: Preparation of 3

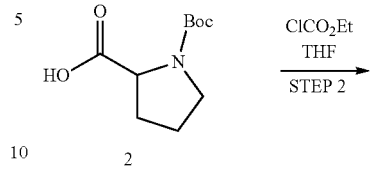

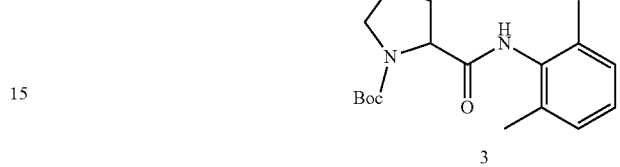

To a mixture of 2 (9 g, 42.6 mmol, 1 eq) in THF (106.5 ml, c=0.4) was added ClCO₂Et (5 g, 46.86 mmol, 1.1 eq) and then dropwise 2,6-dimethylaniline (5.16 g, 42.6 mmol, 1 eq) at 0° C. The reaction mixture was stirred at 60° C. refluxed overnight. After completion, the reaction mixture was turned back to room temperature. Then the mixture was filtered, the filtrate was concentrated in vacuum. The crude product was purified by column chromatography to afford pure product (10.4 g, 74% yield).

Step 3: Preparation of 4

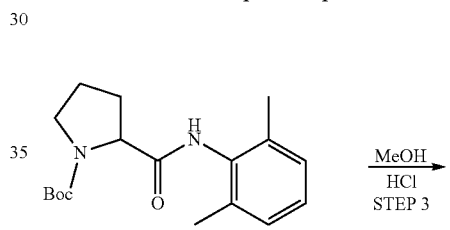

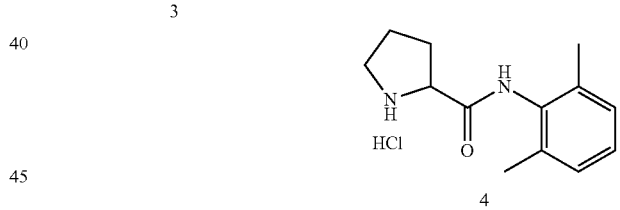

To a solution of 3 (3.4 g, 10.68 mmol, 1 eq) in MeOH (53 mL) was added 4N HCl/MeOH (5.34 mL, 21.36 mmol, 2 eq) at 0° C. After addition, the reaction mixture was stirred at room temperature for 3 h. After completion, the reaction mixture was concentrated in vacuum. The oil was washed with EA and then filtered to afford a white solid (2.02 g, 74.6% yield).

Step 4: Preparation of 5

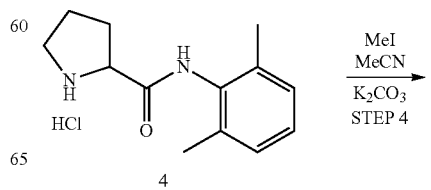

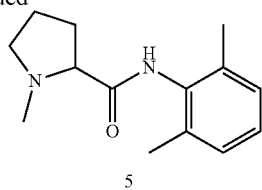

To a solution of 4 (600 mg, 2.35 mmol, 1 eq) in MeCN (6.35 mL, c=0.37) was added K₂CO₃ (0.83 g, 5.99 mmol, 2.55 eq) and MeI (333 mg, 235 mol, 1 eq) then string at room temperature overnight. The mixture was concentrated in vacuum. The crude product was pre-purified by column chromatography to afford pure product (262 mg, 43.16% yield).

Step 5: Preparation of 6

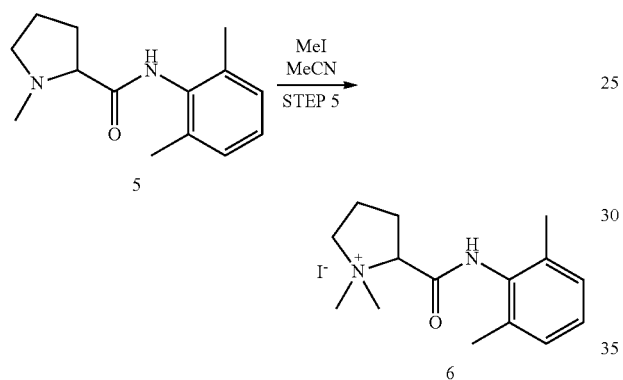

To a solution of 5 (91 mg, 0.43 mmol, 1 eq) in MeCN (4.3 mL, c=0.1) was added MeI (152 mg, 1.075 mmol, 2.5 eq). After addition, the reaction mixture was stirred at room temperature for 2 h. After completion, the reaction mixture was concentrated in vacuum to afford a white solid (140 mg, 87.5% yield).

Step 5: Preparation of 6

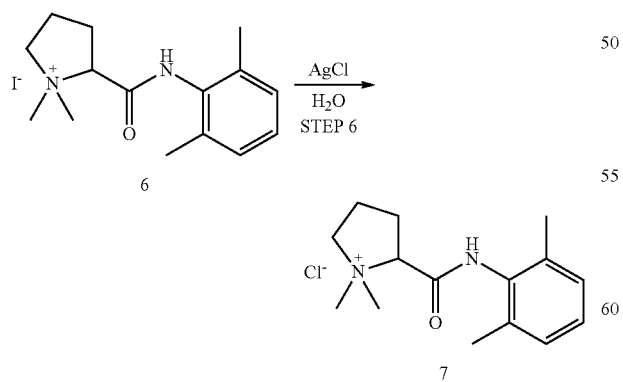

To a solution of 6 (140 mg, 0.288 mmol, 1 eq) in water (0.78 mL, c=0.37) was added AgCl (81 mg, 0.576 mmol, 2 eq). After addition, the reaction mixture was stirred at 60° C. overnight. After completion, the reaction mixture was filtered and lyophilization at 0° C. to give the desired product (92 mg, 80% yield) as a white solid. ¹H NMR (300 MHz, D₂O): δ 7.155~7.098 (m, 3H), 4.500~4.446 (t, J=8.1 Hz, 1H), 3.80~73.768 (m, 1H), 3.621~3.582 (m, 1H), 3.265 (s, 3H), 3.182 (s, 3H), 2.799~5.512 (m, 3H), 2.465~2.437 (m, 1H), 2.294~2.242 (m, 1H), 2.094 (s, 6H) ppm. HPLC purity: 99.07% at 220 nm; Mass: m/z=247.5 (M, ESI+).

Example 8. Synthesis of 2-(2,6-dimethylphenylcarbamoyl)-1,1-diethylpyrrolidinium chloride (Compound 14)

Synthetic Scheme

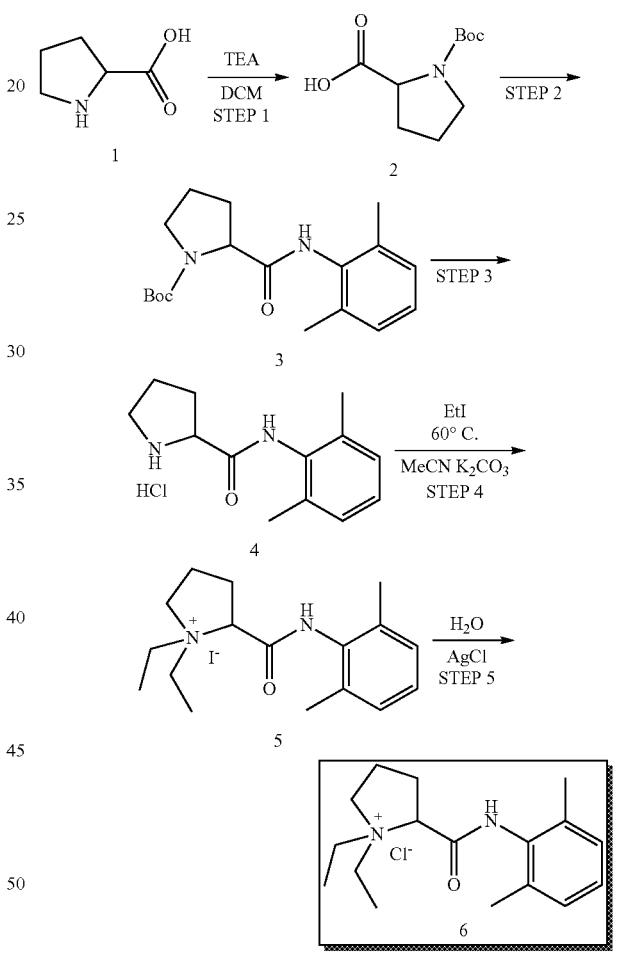

Step 1: Preparation of 2

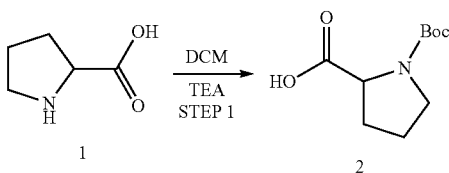 [SMILES: O=C(O)C1CCCN1 ; CC(C)(C)OC(=O)N1CCCC1C(=O)O]

To a mixture of 1 (10 g, 86.9 mmol, 1 eq) in DCM (189 mL, c=0.46) was added TEA (35.2 g, 347.6 mmol, 4 eq) and then dropwise (Boc)₂O (12.57 g, 99.03 mmol, 1.2 eq) at 0° C. After addition, the reaction mixture was warmed slowly to room temperature and stirred for 3 h. The reaction mixture was directed concentrated in vacuum to get a residue without further purification (18 g, 98.36% yield) as white oil.

Step 2: Preparation of 3

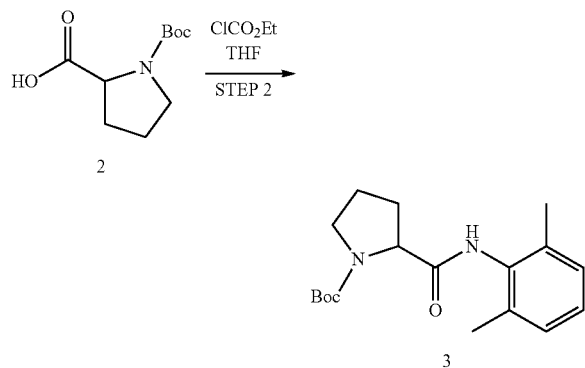

To a mixture of 2 (9 g, 42.6 mmol, 1 eq) in THF (106.5 ml, c=0.4) was added ClCO₂Et (5 g, 46.86 mmol, 1.1 eq) and then dropwise 2,6-dimethylaniline (5.16 g, 42.6 mmol, 1 eq) at 0° C. The reaction mixture was stirred at 60° C. and refluxed overnight. After completion, the reaction mixture was turned back to room temperature. Then the mixture was filtered, the filtrate was concentrated in vacuum. The crude product was purified by column chromatography to afford pure product (10.4 g, 74% yield).

Step 3: Preparation of 4

To a solution of 3 (3.4 g, 10.68 mmol, 1 eq) in MeOH (53 mL) was added 4N HCl/MeOH (5.34 mL, 21.36 mmol, 2 eq) at 0° C. After addition, the reaction mixture was stirred at room temperature for 3 h. After completion, the reaction mixture was concentrated in vacuum. The oil was washed with EA and then filtered to afford a white solid 2.02 g (74.6% yield).

Step 4: Preparation of 5

To a solution of 4 (1.5 g, 5.9 mmol, 1 eq) in MeCN (16 mL, c=0.37) was added K₂CO₃ (2 g, 5.99 mmol, 2.55 eq) and EtI (1.84 g, 11.8 mmol, 2 eq) then string at 60° C. overnight. The second day, the mixture was concentrated in vacuum. The crude product was purified by column chromatography to afford pure product (262 mg, 43.16% yield).

Step 5: Preparation of 6

To a solution of 6 (230 mg, 0.57 mmol, 1 eq) in water (0.78 mL, c=0.37) was added AgCl (163 mg, 1.14 mmol, 2 eq). After addition, the reaction mixture was stirred at 60° C. overnight. After completion, the reaction mixture was filtered and lyophilization at 0° C. to give the desired product (190 mg, 80% yield) as a white solid. ¹H NMR (300 MHz, D₂O): δ 7.162~7.090 (m, 3H), 4.529~4.511 (m, 1H), 3.710~3.358 (m, 6H), 2.682~2.534 (m, 1H), 2.382~2.183 (m, 3H), 2.089 (s, 6H), 1.361~1.273 (m, 6H) ppm. HPLC purity: 96.5% at 220 nm; Mass: m/z=275.5 (M, ESI+).

Example 9. Synthesis of 2-(2,6-dimethylphenylcarbamoyl)-1,1-diethylpiperidinium chloride (Compound 15)

Synthetic Scheme

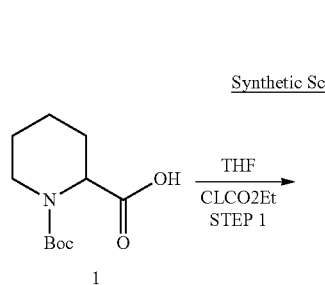

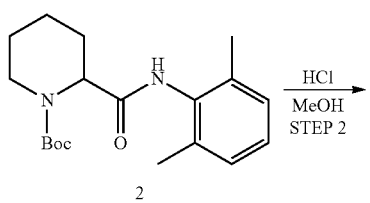

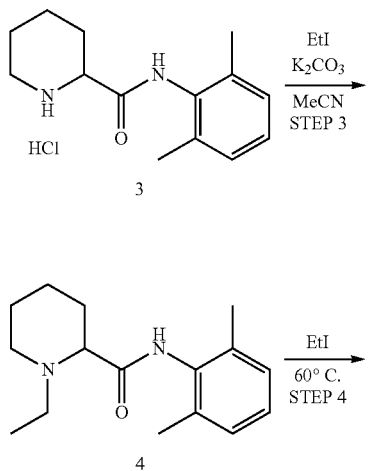

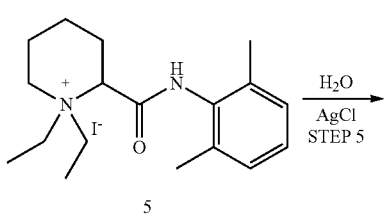

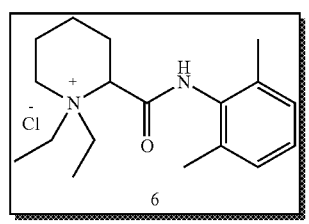

Step 1: Preparation of 2

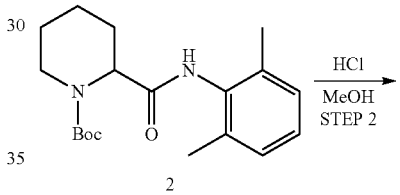

To a solution of 1 (10 g, 43.6 mmol, 1 eq) in THF (109 ml, c=0.4) was added ClCO$_2$Et (5.2 g, 47.9 mmol, 1.1 eq) and then dropwise 2,6-dimethylaniline (5.8 g, 47.9 mmol, 1 eq) at 0° C. The reaction mixture was stirred at 60° C. refluxed overnight. After completion, the reaction mixture was turned back to room temperature. Then the mixture was filtered, the filtrate was concentrated in vacuum. The crude product was purified by column chromatography to afford pure product (7.71 g, 53% yield).

Step 3: Preparation of 3

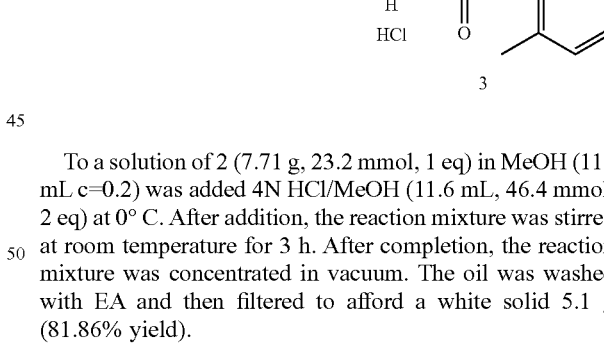

To a solution of 2 (7.71 g, 23.2 mmol, 1 eq) in MeOH (116 mL c=0.2) was added 4N HCl/MeOH (11.6 mL, 46.4 mmol, 2 eq) at 0° C. After addition, the reaction mixture was stirred at room temperature for 3 h. After completion, the reaction mixture was concentrated in vacuum. The oil was washed with EA and then filtered to afford a white solid 5.1 g (81.86% yield).

Step 4: Preparation of 4

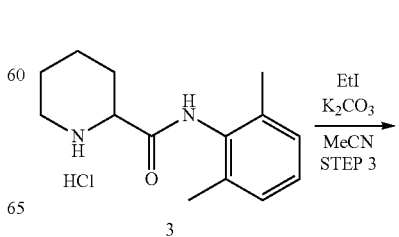

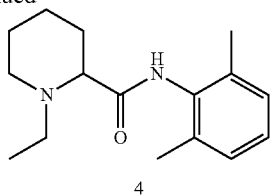

4

To a solution of 3 (2.5 g, 9.3 mmol, 1 eq) in MeCN (25 mL, c=0.37) was added K₂CO₃ (3.3 g, 23.7 mmol, 2.55 eq) and EtI (1.45 g, 9.3 mmol, 1 eq) then string at room temperature overnight. The mixture was concentrated in vacuum. The crude product was pre-purified by column chromatography to afford pure product (2 g, 80% yield).

Step 5: Preparation of 5

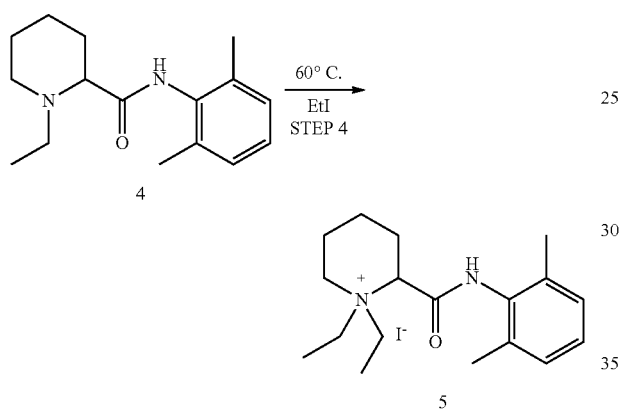

To a solution of 4 (0.5 g, 1.92 mmol, 1 eq) in MeCN (25 mL, c=0.37) was added, and EtI (749 mg, 4.8 mmol, 2.5 eq) then string at 60° C. overnight. The mixture was concentrated in vacuum. The crude product was washed with PE to afford pure product (200 mg, 38.75% yield).

Step 4: Preparation of 6

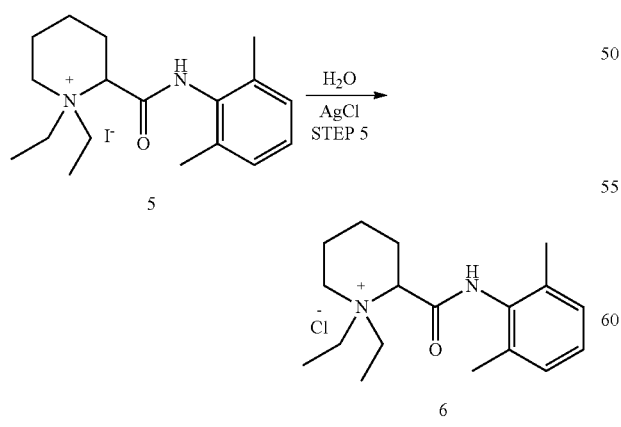

To a solution of 6 (217 mg, 0.52 mmol, 1 eq) in water (1.4 mL, c=0.37) was added AgCl (149 mg, 1.04 mmol, 2 eq).

After addition, the reaction mixture was stirred at 60° C. overnight. After completion, the reaction mixture was filtered and lyophilized at 0° C. to give the desired product (110 mg, 65% yield) as a white solid. ¹H NMR (300 MHz, D₂O): δ 7.127~7.107 (m, 3H), 4.292 (t, 1H), 3.896~3.765 (m, 1H), 3.733~3.412 (m, 4H), 3.365~3.254 (d, 1H), 2.457~2.310 (m, 1H), 2.283~2.231 (m, 1H), 2.083 (s, 6H), 1.875~1.526 (m, 4H), 1.290 (t, J=4.5, J=3, 6H) ppm. HPLC purity: 96.4% at 220 nm; Mass: m/z=289.5 (M, ESI+).

Example 10. Synthesis of 2-(4-fluoro-2,6-dimethylphenylcarbamoyl)-1,1-dimethylpiperidinium chloride (Compound 16)

Synthetic Scheme

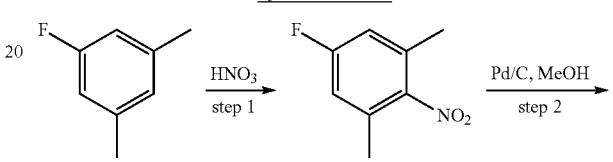

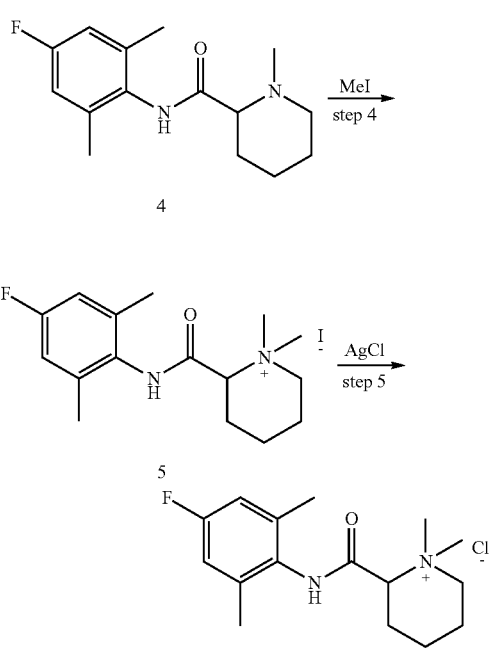

Step 1: Preparation of 5-fluoro-1,3-dimethyl-2-nitrobenzene

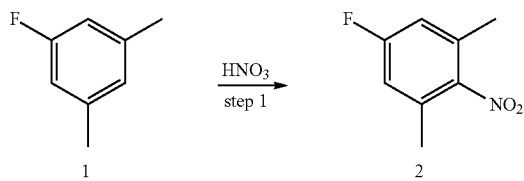

1 (6 g, 48.3 mmol, 1 eq) was cooled to −10° C. and nitric acid (9 g, 143.78 mmol, 3 eq) was added to it dropwise during 20 min. The mixture was stirred at −15° C. for 1 h, then allowed to reach RT carefully and kept for 3 hr with stirring. The mixture was poured into ice to give a yellow precipitate, filtered and the filter cake dissolved with DCM. The organic phase washed by brine, dried on $Na_2SO_4$, concentrated to give the desired product 2 (6.8 g, 83% yield) as a white powder.

Step 2: Preparation of 4-fluoro-2,6-dimethylaniline

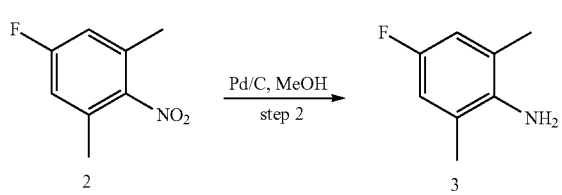

To a solution of 2 (16 g, 94.65 mmol, 1 eq) in MeOH (236 mL) was added Pd/C (1.6 g, 10% w/w) and a couple of drops of Conc.HCl under $H_2$. The mixture was stirred for 5 hr at RT, then filtered and the filtrate was concentrated. The residue was poured into ice, adjusted pH to 10 with 2N NaOH, extracted with EA. The organic phase was washed with brine (150 mL) and dried over anhydrous $Na_2SO_4$ and filtered. The residue after rotary evaporation was purified by column chromatography to give the desired product 3 (5 g, 38.4% yield).

Step 3: Preparation of N-(4-fluoro-2,6-dimethylphenyl)-1-methylpiperidine-2-carboxamide

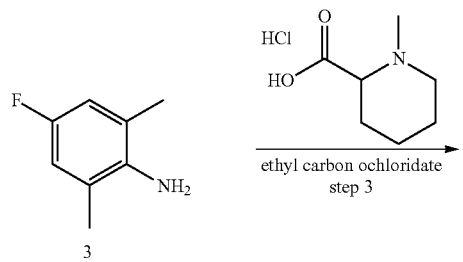

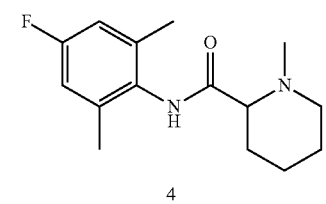

To a solution of 1-methylpiperidine-2-carboxylic acid hydrochloride (2.27 g, 12.65 mmol, 1.1 eq) in DCM (46 mL, c=0.25) was added TEA (5.12 g, 50.6 mmol, 4.4 eq) under nitrogen and stirred at RT for 30 min. The mixture was cooled to 0° C. at an ice-bath, then $ClCO_2Et$ was added dropwise slowly during a period of 20 min. To the mixture above was added 3 (1.6 g, 11.5 mmol, 1.0 eq) in DCM (2 mL) dropwise, stirred for overnight. The mixture after rotary evaporation was purified by column chromatography to give the desired product 4 (0.5 g, 16% yield).

Step 4: Preparation of 2-(4-fluoro-2,6-dimethylphenylcarbamoyl)-1,1-dimethylpiperidinium iodide

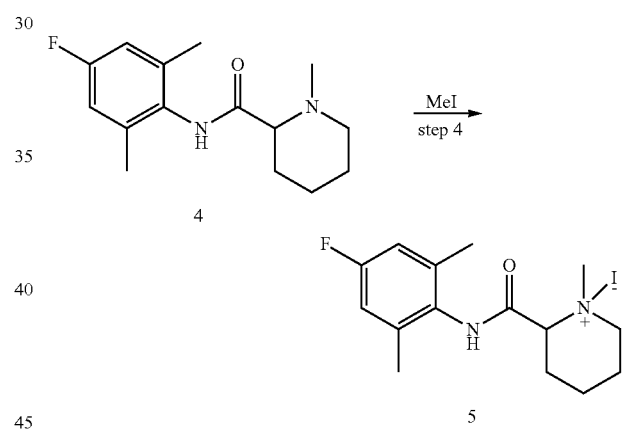

To a solution of 4 (0.5 g, 1.89 mmol, 1.0 eq) in MeCN (35.8 mL) was added MeI (1.025 g, 7.225 mmol, 2.5 eq), stirred at 90° C. in a 75 mL of sealed tube with stirring for 2 h. After completion, removed the solvent to give the desired product 5 (760 g, 99% yield).

Step 5: Preparation of 2-(4-fluoro-2,6-dimethylphenylcarbamoyl)-1,1-dimethylpiperidinium chloride

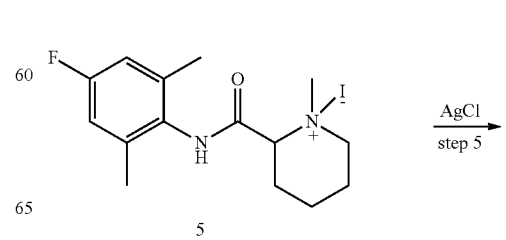

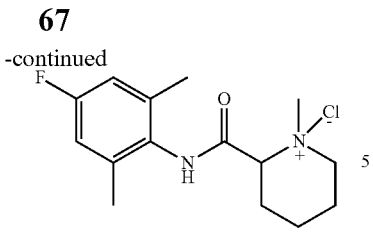

To a solution of 5 (0.3 g, 0.739 mmol, 1.0 eq) in deionized water (2.5 mL) was added AgCl (212 mg, 1.48 mmol, 2.0 eq), stirred at 60° C. with stirring for 30 min. After completion, the reaction was filtered, and the filtrate was lyophilized to give 6 (160 g, 73% yield). $^1$H NMR (300 MHz, D$_2$O-d$_6$): δ 6.90 (d, J=9.6 Hz, 2H), 4.21~4.11 (m, 1H), 3.69~3.60 (m, 1H), 3.48~3.35 (m, 1H), 3.27 (d, J=11.1 Hz, 6H), 2.30~2.18 (m, 2H), 2.17~2.00 (m, 6H), 1.95~1.55 (m, 5H) ppm.

Example 11. Synthesis of 2-(4-aminophenylamino)-N,N,N-triethyl-2-oxoethanaminium (Compound 22)

Synthetic Scheme

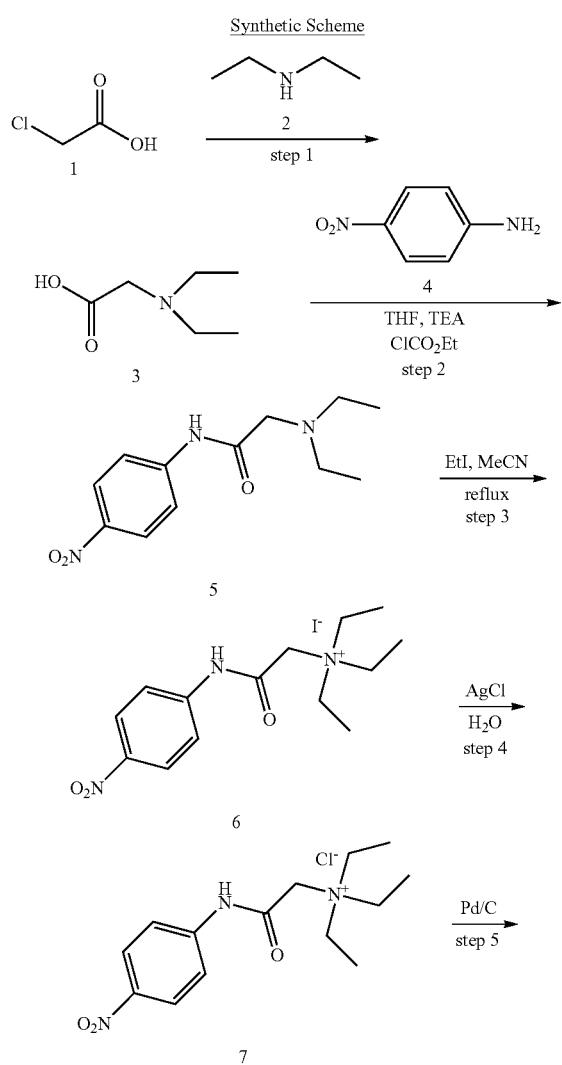

Step 1: Preparation of 3

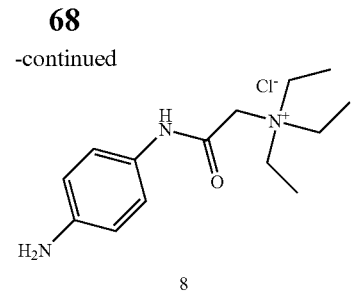

To a mixture of 2 (240 mL, 7.2 eq) was added 1 (30 g, 1.0 eq) in batches. The mixture was stirred at 30° C. overnight. After completion, the suspension was filtered and the filter cake washed with EA (30 mL×2), 150 mL EA was added to the filter cake and stirred for 30 min at 30° C. Then the suspension was filtered and the filter cake washed with EA (30 mL×2), the filtrate was concentrated under reduce pressure. The residue was added to 90 mL Acetonitrile/acetone (1:2) and stirred at RT. over night. The suspension was filtered and the filter cake was dried under reduce pressure to give the product (9.7 g, yield=23.3%).

Step 2: Preparation of 5

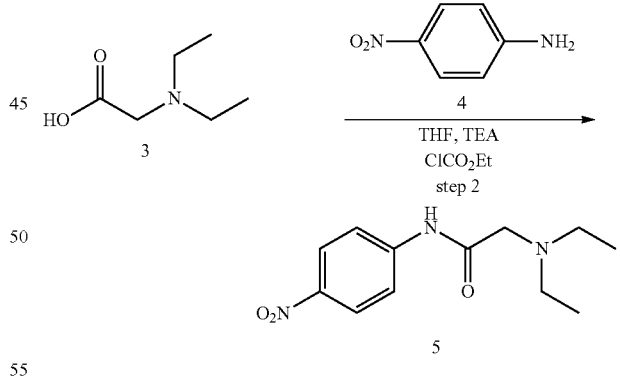

To a mixture of 3 (1.0 g, 7.6 mmol, 1.0 eq) and TEA (1.5 g, 15.2 mmol, 2.0 eq) in THF (19 ml, c=0.4) was added ClCO$_2$Et (0.9 g, 8.36 mmol, 1.1 eq). Then the solution was added 4 (1.15 g, 8.36 mmol, 1.1 eq). The reaction mixture was stirred at reflux overnight. Then the suspension was filtered and the filtrate was concentrated under reduce pressure. The residue was dissolved with EA and washed with acid-base to give the product (0.35 g, yield=20%). $^1$HNMR (300 MHz DMSO): δ 10.2268 (s, 1H), 8.2159 (d, J=9.18 Hz, 2H), 7.9377 (d, J=9.15 Hz, 2H), 3.2379 (s, 2H), 2.5458~2.6470 (dd, 4H), 1.0139 (t, 6H).

Step 3: Preparation of 6

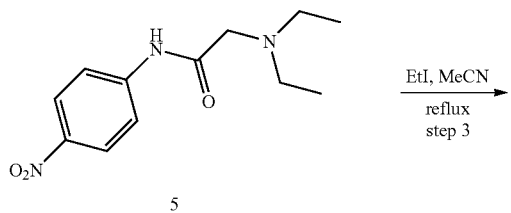

To a mixture of 5 (300 mg, 1.19 mmol, 1.0 eq) in MeCN (12 ml, c=0.1) was added EtI (651.5 mg, 4.18 mmol, 3.5 eq). The reaction mixture was heated to reflux overnight. After completion, the reaction solution was concentrated under reduce pressure to give the product (200 mg, yield=41%, HPLC: 98%).

Step 4: Preparation of 7

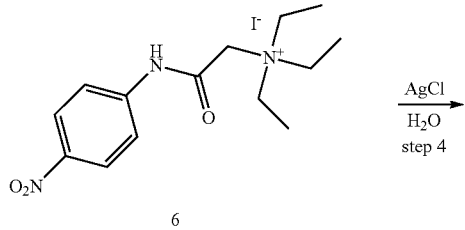

To a solution of 5 (200 mg, 0.49 mmol, 1.0 eq) in deionized water (4 mL, c=0.12) was added AgCl (140.8 mg, 0.98 mmol, 2.0 eq). Then the solution was heated to 60° C. and stirred overnight. After completion, the suspension was filtered and the filtrate was used to next step.

Step 5: Preparation of 8

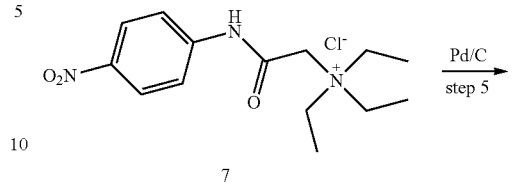

To the filtrate of step 3 was added Pd/C (30 mg, m/m=0.2) 2 drops of 2N HCl. The solution was displaced with H$_2$. Then the solution was stirred at 35° C. overnight. After completion, the suspension was filtered was lyophilized and the residue was washed with EA to give the product (92.4 mg, yield=66%). HPLC purity: 98.8% at 220 nm, 99% at 254 nm; Mass: M$_+$: M−35.5=250.5; M−: M=285.5; M+35.5=321.4. $^1$H NMR (300 MHz, D$_2$O): δ 7.4742 (d, J=8.7 Hz, 2H), 7.2281 (d, J=8.79 Hz, 2H), 4.1406 (s, 2H), 3.5985 (dd, J=7.2 Hz, 6H), 1.3526 (t, J=7.2 Hz, 9H). ppm.

Example 12. Synthesis of 2-(4-amino-2,6-dimethylphenylamino)-N, N, N-triethyl-2-oxoethanaminium chloride (Compound 23)

Synthetic Scheme

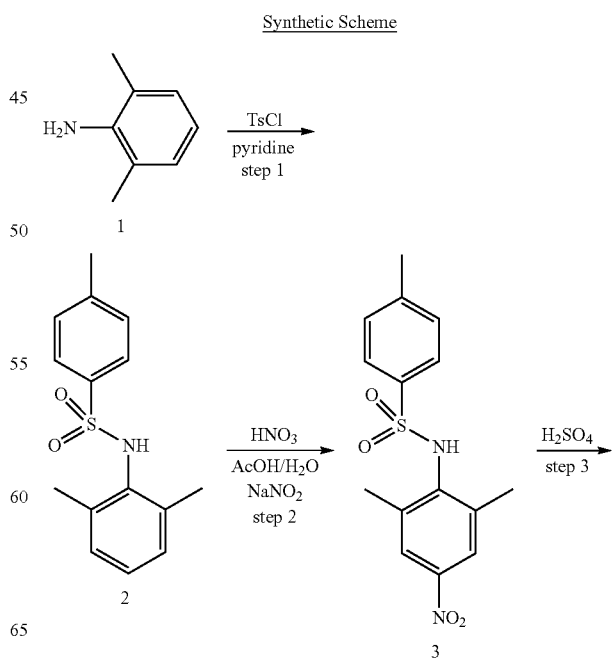

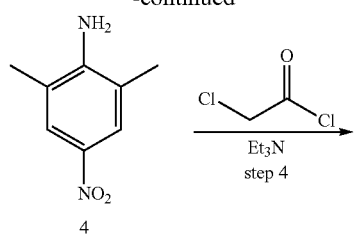

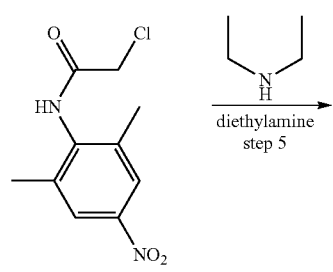

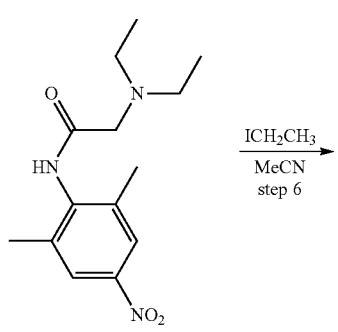

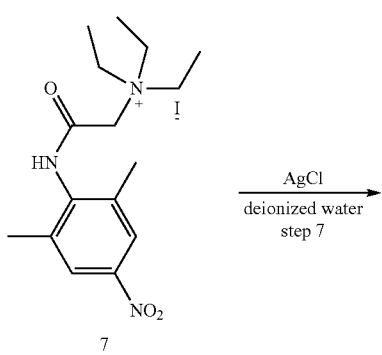

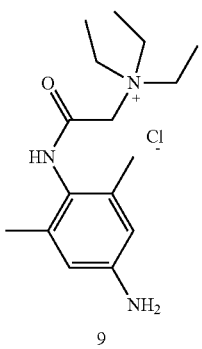

Step 1: Preparation of N-(2,6-dimethylphenyl)-4-methylbenzenesulfonamide

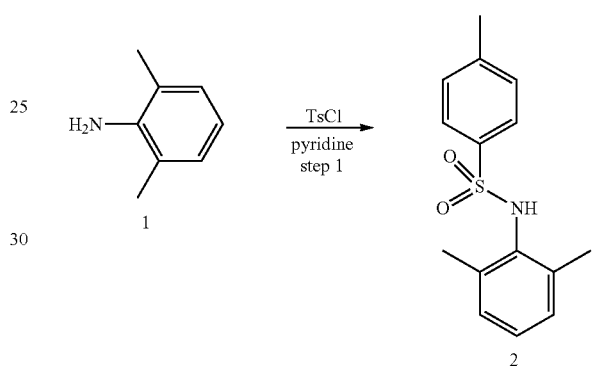

To a solution of 1 (15 g, 123.8 mmol, 1 eq) in Pyridine (334 mL, c=0.37) was added TsCl (28 g, 148.54 mmol, 1.2 eq), heated to reflux at 115° C. for 4 hours. The reaction mixture was cooled to RT, removed the solvent, adjusted pH to 6 with 2N HCl, washed with water, extracted with EA, washed by brine, concentrated and the residue recrystallized from hot ethanol to give the desired product 2 (19.8 g, 56% yield) as a white powder.

Step 2: Preparation of N-(2,6-dimethyl-4-nitrophenyl)-4-methylbenzenesulfonamide

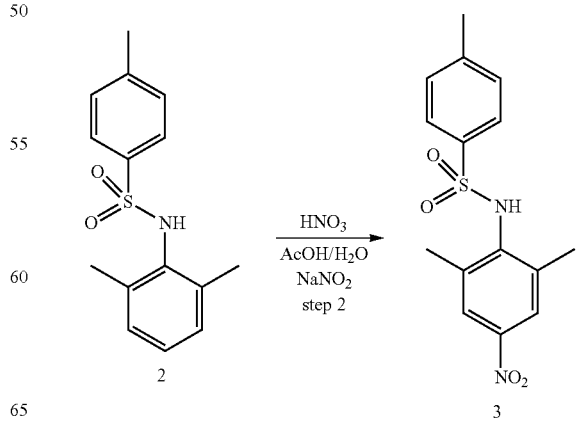

To a suspension of 2 (19.8 g, 71.9 mmol, 1 eq) in AcOH: H₂O (150 Ml: 100 mL) was added NaNO₂ under nitrogen with stirring, con.HNO₃ (9 g, 194 mmol, 2 eq) was added dropwise during a period of 10 min, refluxed at 110° C. for 5 hr. After completion, the reaction was diluted with H₂O (150 mL), extracted with EA (200 mL), adjusted pH to 8 with 1N NaOH. The organic phase was washed with brine (150 mL) and dried over anhydrous Na₂SO₄. The filtrate was evaporated in vacuum to give 3 (16 g, 70% yield) as a powder.

Step 3: Preparation of 2,6-dimethyl-4-nitroaniline

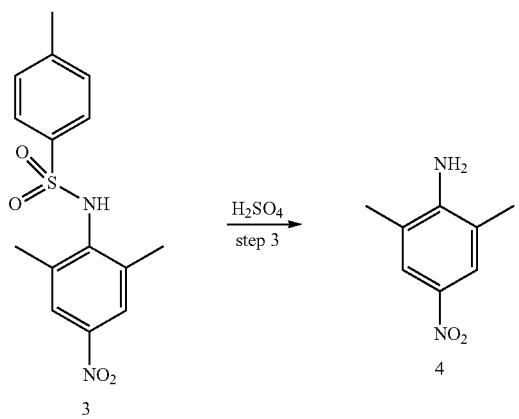

A solution of 3 (23 g, 72 mmol, 1.0 eq) in con.H₂SO₄ (232 mL, c=0.3) was heated at 60° C. for 1 h with stirring. After completion, the reaction was poured into ice (1000 mL) and adjusted pH=8 with 20% NaOH. extracted with EA (200 mL). The organic phase was washed with brine (15 mL) and dried over anhydrous Na₂SO₄ and filtered. The residue after rotary evaporation was purified by column chromatography to give the desired product 4 (8 g, 66% yield).

Step 4: Preparation of 2-chloro-N-(2,6-dimethyl-4-nitrophenyl) acetamide

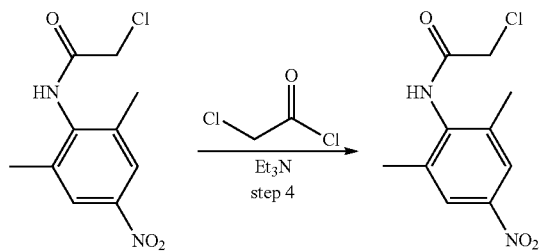 [SMILES: Cc1cc([N+](=O)[O-])cc(C)c1NC(=O)CCl ; O=C(Cl)CCl ; Cc1cc([N+](=O)[O-])cc(C)c1NC(=O)CCl]

To a mixture of 4 (4 g, 24 mmol, 1.0 eq) in DCM (30 mL, c=0.8) was added pyridine (2.28 g, 28.8 mmol, 1.2 eq), 2-chloroacetyl chloride (3.25 g, 28.8 mmol, 1.2 eq) dropwise at 0° C., stirred at RT for overnight with stirring. After completion, the reaction was filtered, and the cake was poured into water, adjusted pH to 4 with 2N HCl, filtered and the cake dried to give the desired product 5 (4.4 g, 76% yield).

Step 5: Preparation of 2-(diethylamino)-N-(2,6-dimethyl-4-nitrophenyl) acetamide

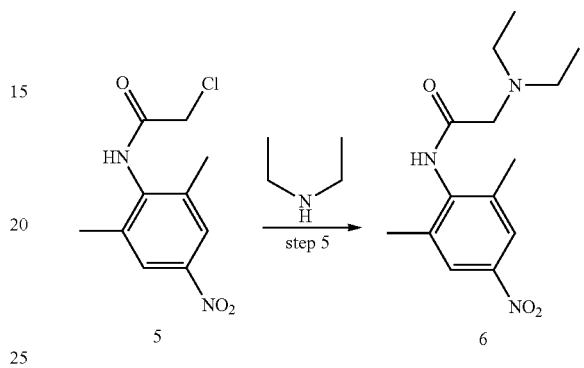

A mixture of 5 (4 g, 16.48 mmol, 1.0 eq) in diethylamine (46.7 mL, 639 mmol, 38.8 eq) was heated to reflux at 55° C. for 5 hr, removed solvent, poured into water, extracted with EA (100 mL×3). The organic phase was washed with brine (15 mL) and dried over anhydrous Na₂SO₄ and filtered. The residue after rotary evaporation was purified by column chromatography to give the desired product 6 (2.17 g, 47% yield).

Step 6: Preparation of 2-(2,6-dimethyl-4-nitrophenylamino)-N, N, N-triethyl-2-oxoethanaminium iodide

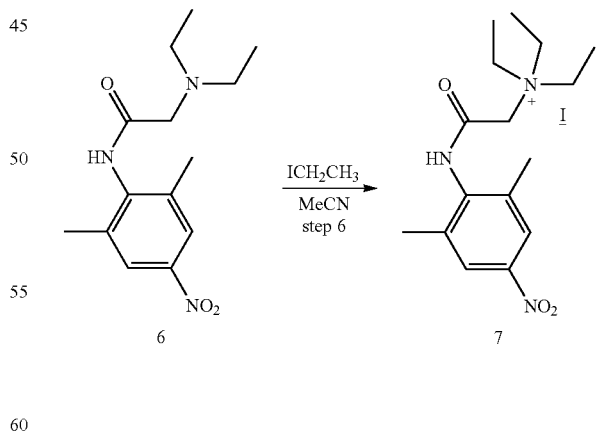

To a solution of 6 (1 g, 3.58 mmol, 1.0 eq) in MeCN (35.8 mL) was added EtI (1.4 g, 8.95 mmol, 2.5 eq), stirred at 90° C. in a 75 mL of sealed tube with stirring for 3 day. After completion, removed the solvent to give the desired product 7 (1.48 g, 95% yield).

Step 7: 2-(2,6-dimethyl-4-nitrophenylamino)-N, N, N-triethyl-2-oxoethanaminium chloride

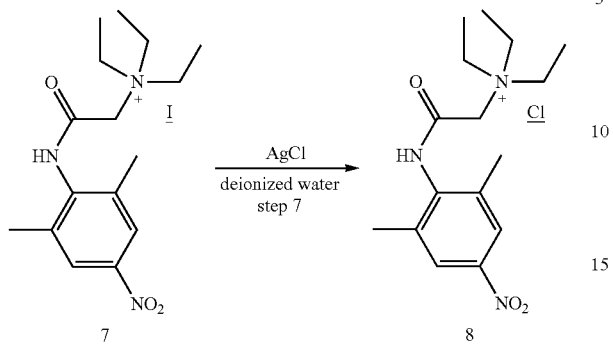

To a solution of 7 (0.5 g, 1.15 mmol, 1.0 eq) in deionized water (2 mL) was added AgCl (329 mg, 2.3 mmol, 2.0 eq), stirred at 60° C. with stirring for overnight. After completion, the reaction was filtered to give the filtrate 8.

Step 8: Preparation of N-(4-amino-2,6-dimethylphenyl)-2-(diethylamino)acetamide

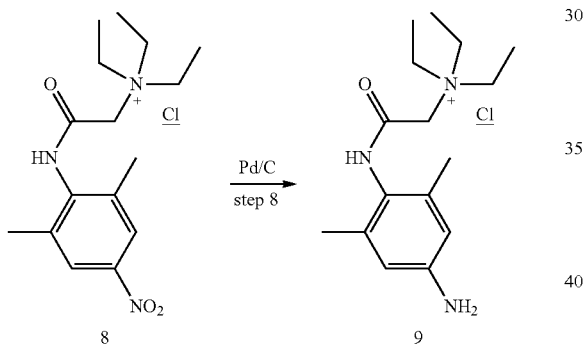

To a mixture of 8 above was added Pd/C (39.5 mg, 10% w/w), the suspension was degassed under vacuum and purged with $H_2$ several times, stirred for 6 hr at RT. After completion, the reaction was filtered, and the cake was washed with EA (1.5 mL), filtrated to give the desired product 9 (250 mg, 74% yield) as a white powder. $^1$H NMR (300 MHz, $D_2O$-$d_6$): δ 7.05 (s, 2H), 4.22 (s, 2H), 3.53~3.50 (m, 6H), 2.11 (s, 6H), 1.30~1.25 (m, 9H) ppm.

Example 13. Synthesis of 3-(2,6-dimethylphenylamino)-N,N,N-triethyl-3-oxopropan-1-aminium chloride (Compound 24)

Synthetic Scheme

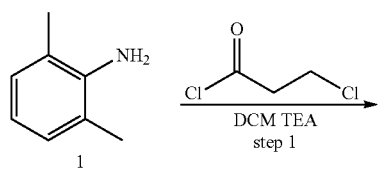

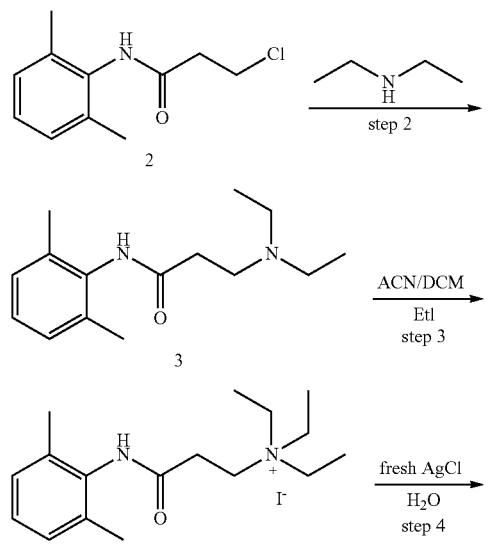

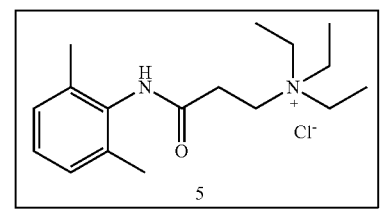

Step 1: Preparation of 2

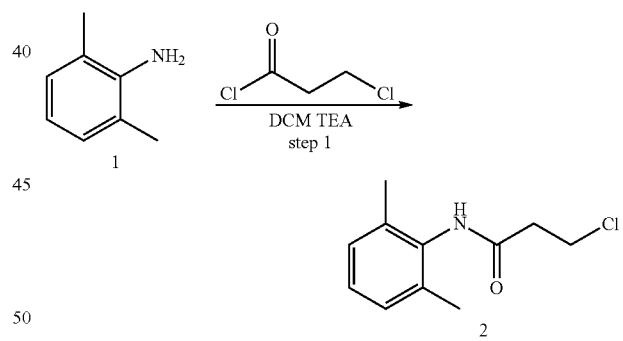

To a mixture of 1 (10 g, 82.52 mmol, 1 eq) in DCM (50 mL, c=1.6) was added TEA (10.02 g, 99.03 mmol, 1.2 eq) and was drop wised 3-chloropropanoyl chloride (12.57 g, 99.03 mmol, 1.2 eq) in DCM (50 mL, c=1.6) at 0° C. After addition, the reaction mixture was warmed slowly to room temperature and stirred for 2 h. After completion, the reaction solution was adjusted to pH=3-4 with 1N HCl and extracted with DCM (2×50 mL). The combined organic phases was adjusted to pH=7-8 with saturated $NaHCO_3$. The combined organic phases was washed with brine, dried over $Na_2SO_4$, filtered and concentrated in vacuum at 25° C. The residue was purified by column chromatography to give the desired product (12.46 g, 71.3% yield, included 46% N-(2,6-dimethylphenyl) acryl amide) as a white solid.

Step 2: Preparation of 3

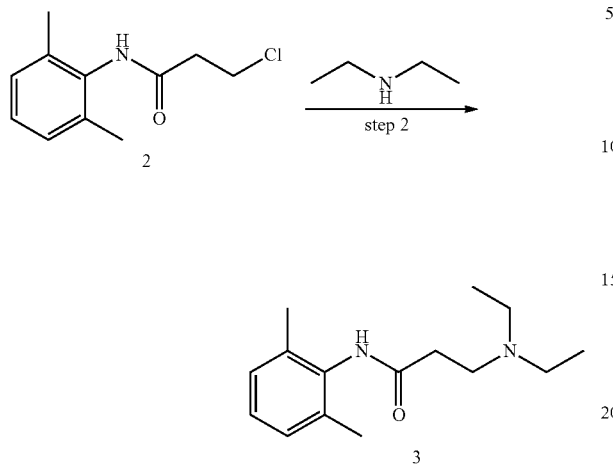

To 2 (8 g, 37.79 mmol, 1 eq) was added diethylamine (107.24 g, 1466.29 mmol, 38.8 eq). The reaction mixture was stirred at 55° C. overnight. After completion, the reaction mixture was concentrated in vacuum. And then the residue diluted with water (150 mL) and extracted with EA (3×100 mL). The combined organic phases was washed with brine, dried over $Na_2SO_4$, filtered and concentrated in vacuum. The residue was purified by column chromatography to give the desired product (5.75 g, 61% yield) as yellow oil.

Step 3: Preparation of 4

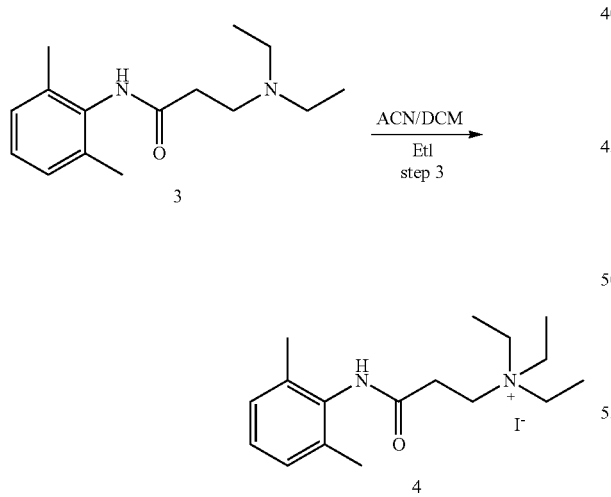

To a solution of 3 (3 g, 12.08 mmol, 1 eq) in ACN (121 Ml, c=0.1) was added EtI (5.65 g, 36.24 mmol, 3 eq). After addition, the reaction mixture was stirred at 85° C. overnight. After completion, the reaction mixture was concentrated in vacuum. The residue was purified by column chromatography to give the desired product (3.6 g, 74% yield) as a white solid.

Step 4: Preparation of 5

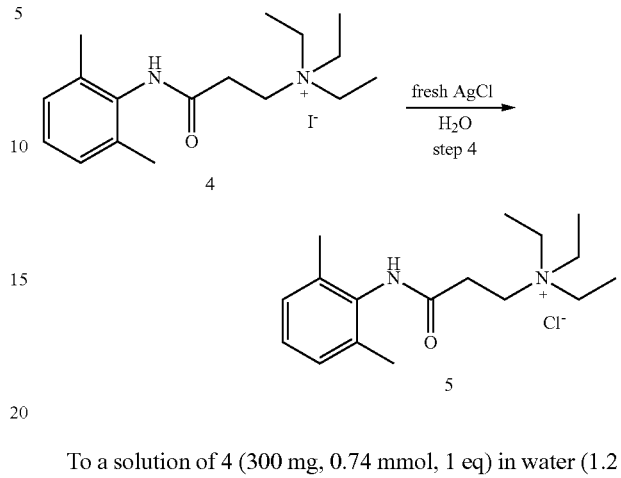

To a solution of 4 (300 mg, 0.74 mmol, 1 eq) in water (1.2 mL, c=0.6) was added fresh AgCl (212 mg, 1.48 mmol, 2 eq) at 6-7° C. After addition, the reaction mixture was stirred at 6-7° C. for 4 min. After completion, the reaction mixture was filtered and lyophilized at 0° C. to give the desired product (133 mg, 57% yield) as a white solid. $^1$H NMR (300 MHz, $D_2O$): δ 7.063~7.128 (m, 3H), 3.495 (t, J=7.8 Hz, J=8.1 Hz, 2H), 3.220~3.293 (m, 4H), 2.909 (t, J=7.8 Hz, J=8.1 Hz, 2H), 2.100 (d, J=22.5 Hz, 6H), 1.212 (t, J=7.2 Hz, 6H) ppm. HPLC purity: 99.7% at 220 nm.

Example 14. Synthesis of 2-(4-aminobenzamido)-N,N,N-triethylethanaminium chloride hydrochloride (Compound 26)

Synthetic Scheme

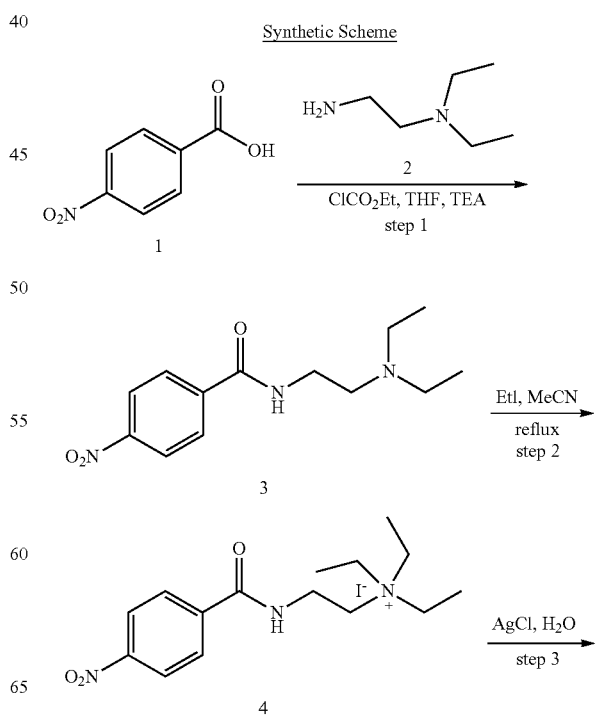

-continued

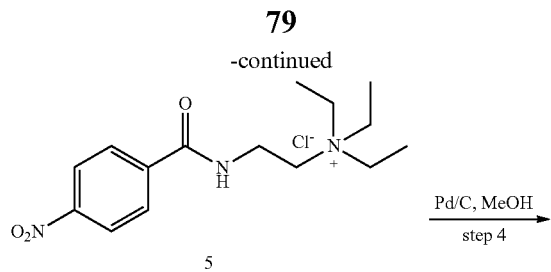

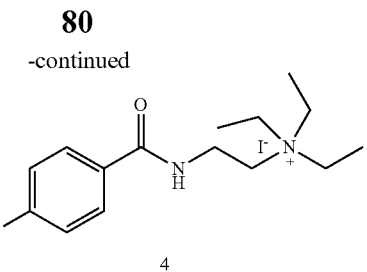

To a mixture of 3 (200 mg, 0.75 mmol, 1.0 eq) in MeCN (7.5 ml, c=0.1) was added EtI (293 mg, 1.88 mmol, 2.5 eq). The reaction mixture was heated to reflux overnight. After completion, the reaction solution was concentrated under reduce pressure to give the product (313.8 mg, yield=99.3%, LCMS: 100%).

Step 3: Preparation of 5

Step 1: Preparation of 3

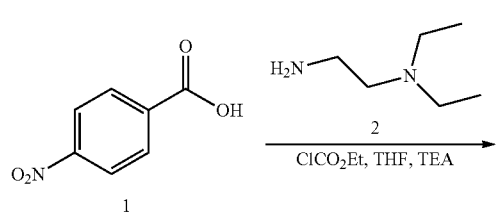

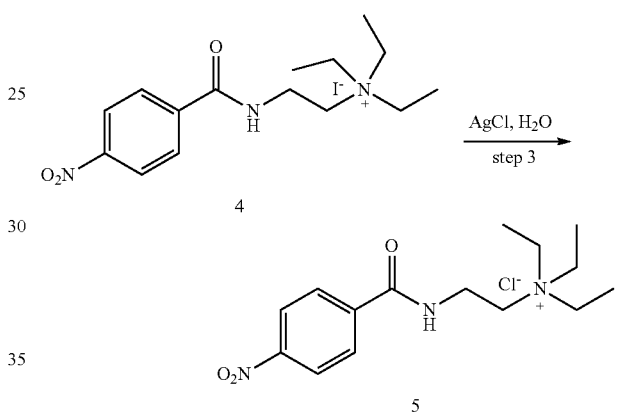

To a solution of 4 (195.7 mg, 0.46 mmol, 1.0 eq) in deionized water (4 mL, c=0.1) was added AgCl (133 mg, 0.93 mmol, 2.0 eq). Then the solution was heated to 60° C. and stirred overnight. After completion, the suspension was filtered and the filtrate was used to next step.

To a mixture of 1 (1.6 g, 9.46 mmol, 1.1 eq) and TEA (1.7 g, 17.2 mmol, 2 eq) in THF (25 mL, c=0.37) was added ClCO$_2$Et (1.0 g, 9.46 mmol, 1.1 eq) slowly. Then 2 (1.0 g, 8.6 mmol, 1 eq) was added to the mixture. The mixture was stirred at RT. for 5 h. After completion, the suspension was filtered and the filtrate was concentrated under reduce pressure. The residue was purified by column chromatography and washed with NaOH to give the product (1.0 g, yield=43.8%, HPLC: 99.8%).

Step 4: Preparation of 6

Step 2: Preparation of 4

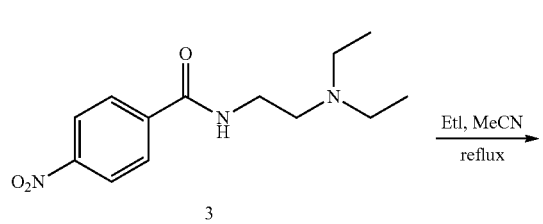

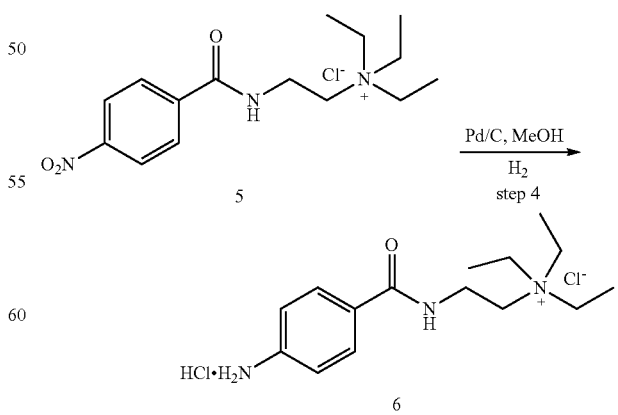

To the filtrate of step 3 was added MeOH (4 mL), Pd/C (15 mg, m/m=0.1), 2 drops of 2N HCl. The solution was displaced with $H_2$. Then the solution was stirred at 35° C. overnight. After completion, the suspension was filtered and the 4N HCl/MeOH (0.5 mL) was added to the solution and stirred for 30 min. Then the solution was lyophilized and the residue was washed with EA to give the product (55 mg, yield=36%). HPLC purity: 95.9% at 220 nm; 96.7% at 254 nm; Mass: $M_+$: M−35.5=264.5, M−: M+35.5=334.5; $^1$H NMR (300 MHz, $D_2O$): δ 7.8252 (d, J=8.3 Hz, 2H), 7.4115 (d, J=8.4 Hz, 2H), 3.7562 (t, J=6.6 Hz, 2H), 3.3613 (m, 9H), 1.2785 (t, J=7.5 Hz, 10H) ppm.

Example 15. Compound 6 has Greater Efficacy than QX-314 in Inhibiting Sodium Channels when Applied Inside Cells FIG. 1A shows the time course of peak sodium current as a function of time for cells dialyzed with either 100 micromolar QX-314 or 100 micromolar BW8186 (Compound 6) and stimulated with a series of 30-msec depolarizations to −20 mV from a holding potential of −100 mV. To induce use-dependent block, the depolarizations were delivered by series of increasing rates: 0.05 Hz for 1-min, 0.33 Hz for 1-min, 1 Hz for 1-min, 3 Hz for 1-min, 5 Hz for 30 seconds, 10 Hz for 30 seconds, with 1 minute rest between each series of pulses. After the series of pulses to induce use-dependent block, the time course of recovery was followed using pulses delivered at $C_1$. Hz (2-min) and 0.05 Hz (1-min). Peak sodium current was plotted as a function of experimental time (1-min per division on the time axis).

As can be seen in FIG. 1A, QX-314 and Compound 6 both show strong use dependent accumulation of block at stimulation frequencies from 1 to 10 Hz, with only partial recovery during 1-minute rest intervals. QX-314 produced use-dependent inhibition of sodium current to about 20% of the initial value, followed by partial recovery to about 40% of the initial value after 3 minutes of slow stimulation. Compound 6 produced more profound use-dependent block, to about 3% of the initial sodium current, and recovered very little during 3 minutes of slow stimulation, to about 5% of the initial value. Thus, compared with QX-314, Compound 6 shows more accumulation of use-dependent block and also strikingly less recovery from block during periods of no stimulation or a long period of slow stimulation (0.05 Hz) after development of block. This indicates that Compound 6 is trapped in the cell and may result in a prolonged analgesic effect in vivo.

Figure 1B:
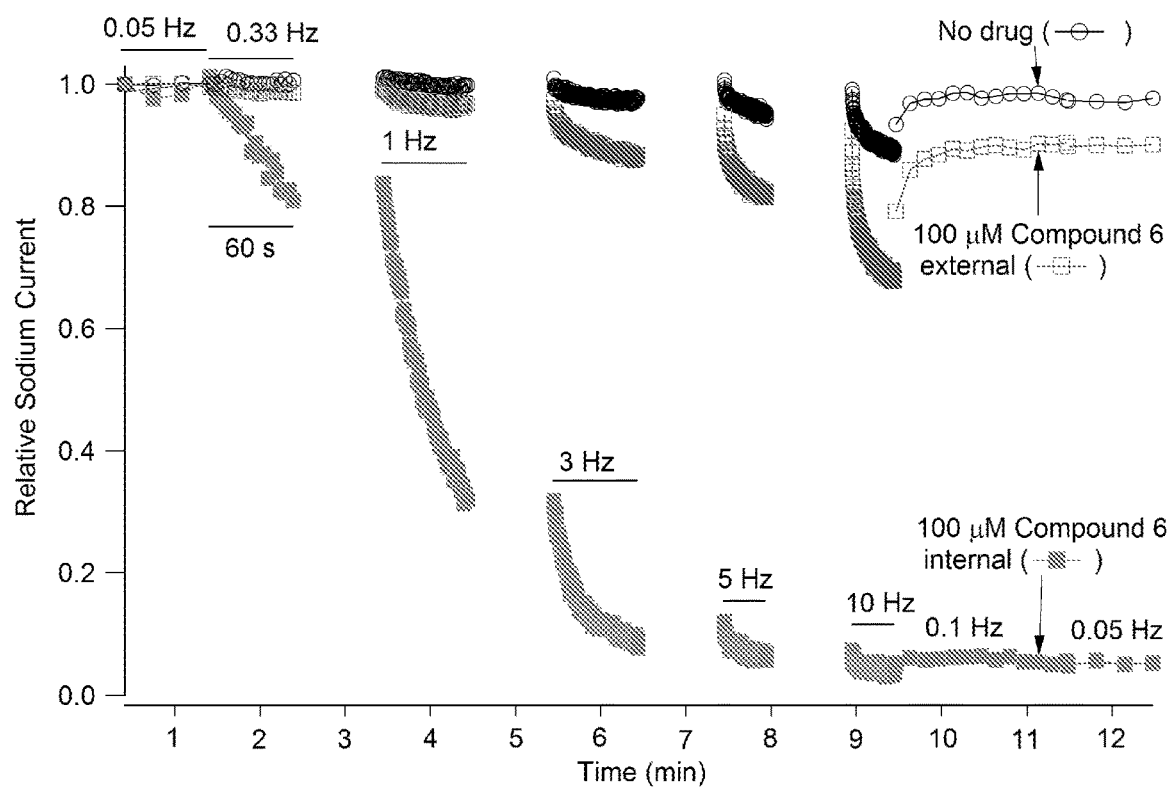
FIG. 1B shows that compound 6, applied externally (middle trace) has very little effect (comparable to the absence of drug) when tested with the same protocol.
Figure 2A:
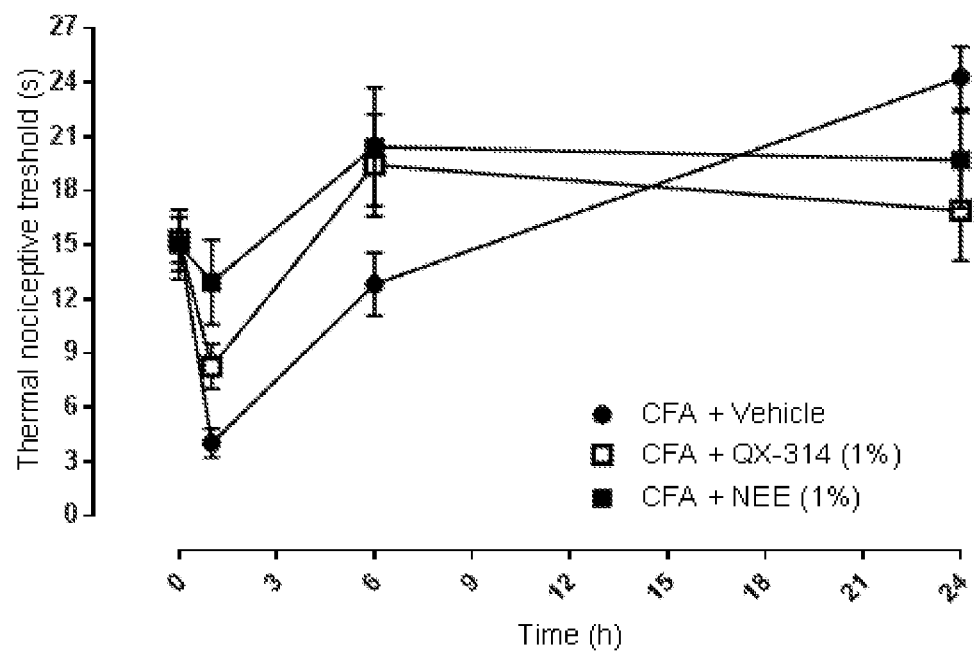
FIGS. 2A-2D show reversal of CFA-induced thermal hyperalgesia by charged sodium channel blockers.
Figure 2B:
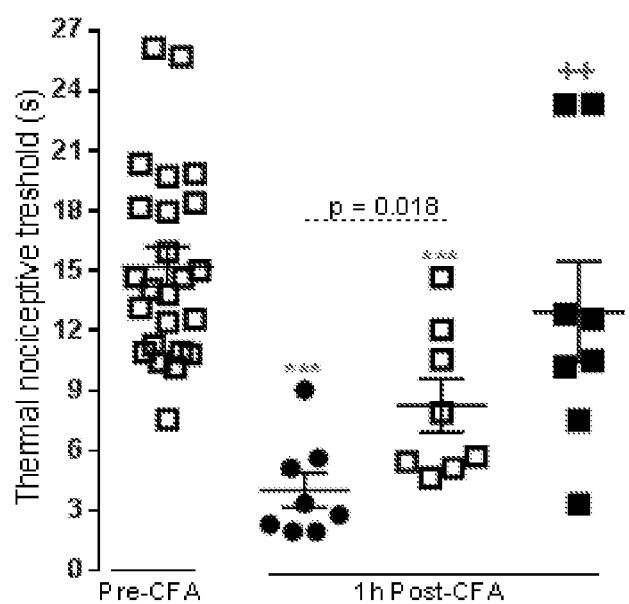
Figure 2C:
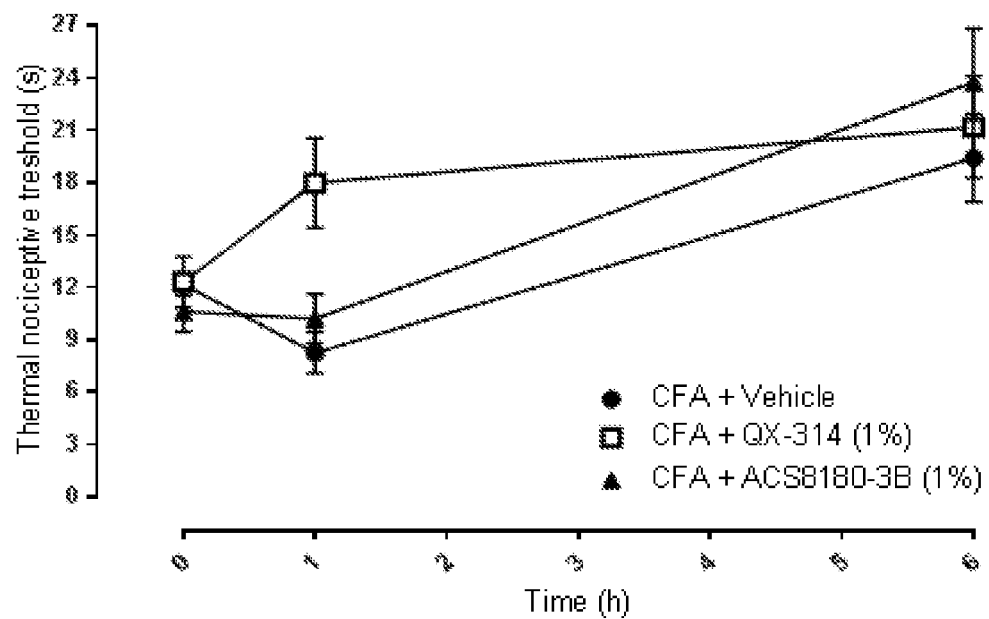
Figure 2D:
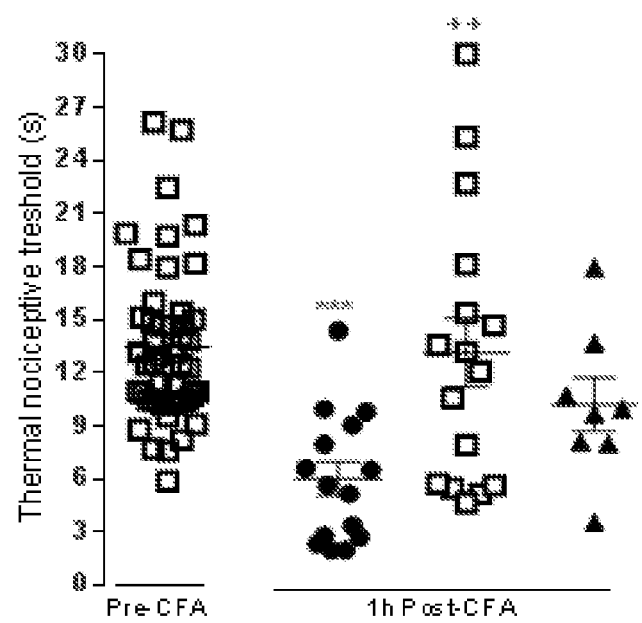

FIG. 1B shows that Compound 6 is far more effective when applied inside the cell (presented inside the recording pipette during whole cell recording so that the cell dialyzed) than when it is applied outside the cell. This supports the idea that, like QX-314, Compound 6 should have only weak effects on neuronal activity unless it can enter neurons through activated TRPV1, TRPA1, or other large-pore channels, present selectively in neurons mediating pain and itch.

Figure 3B:
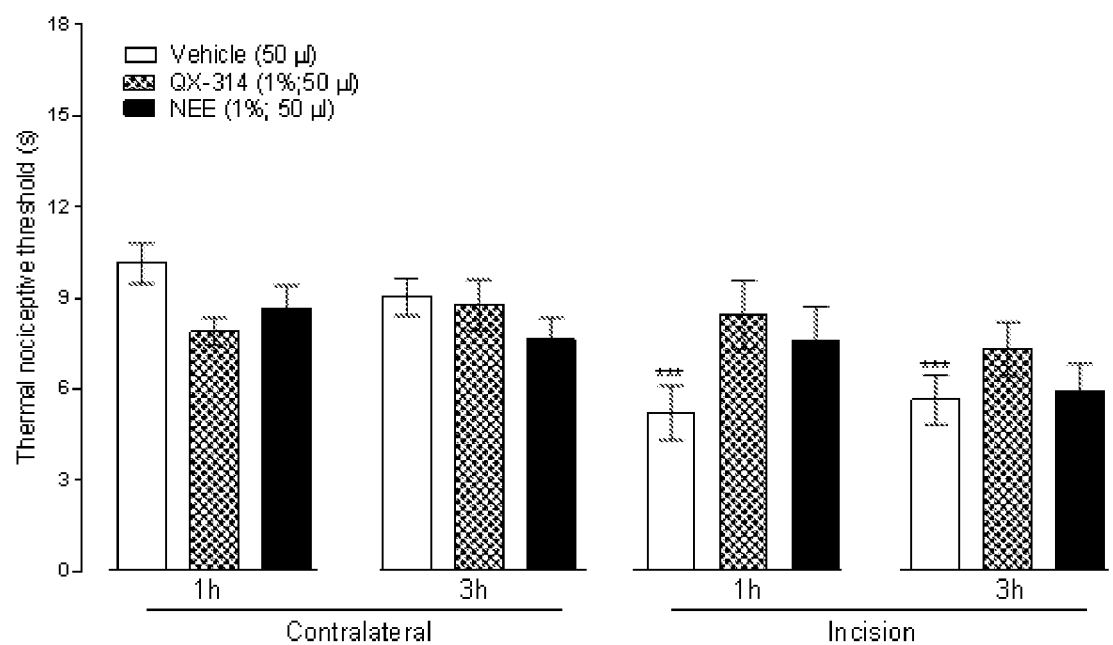
Figure 5A:
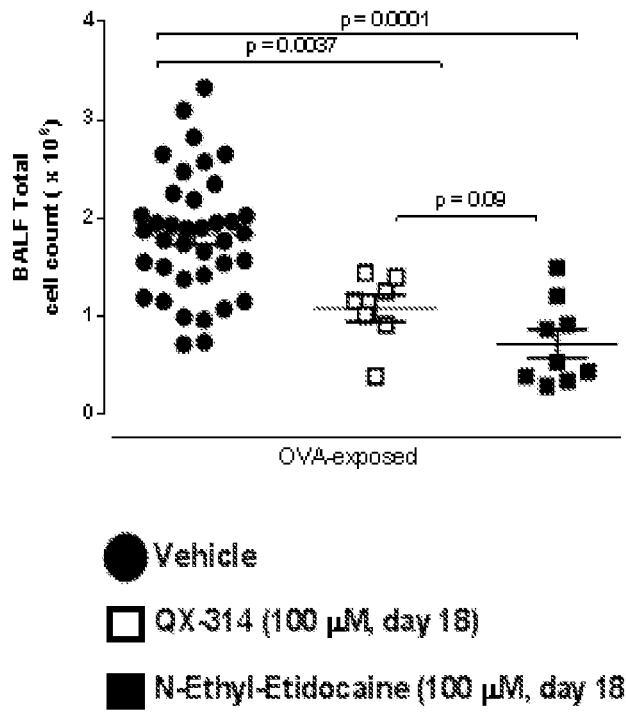
FIG. 5A-5E are results showing that lung sensory neuron silencing with N-ethyl-etidocaine (Compound 21) reduces allergic airway inflammation. OVA-exposed mice (day 21) develop increases in BALF total (FIG. 5A), and $CD45^+$ cells (FIG. 5B), including eosinophil (FIG. 5C), macrophage (FIG. 5D) and T-cell (FIG. 5E) counts. In comparison to vehicle treatment, the silencing of sensory neurons using aerosolized QX-314 (100 μM, hollow square) or N-ethyl-etidocaine (Compound 21) (100 μM, dark square) decreased these levels. N-ethyl-etidocaine (Compound 21) shows a tendency toward a greater decrease in comparison to QX-314. Data expressed as mean±S.E.M; Two-tailed unpaired Student's t-test (n=8-16 animals/group; 1-2 cohorts).
Figure 5B:
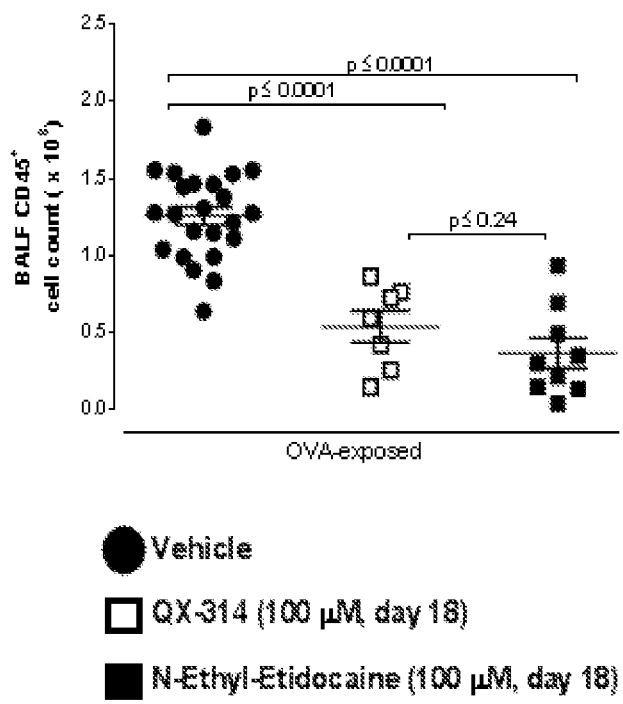
Figure 5C:
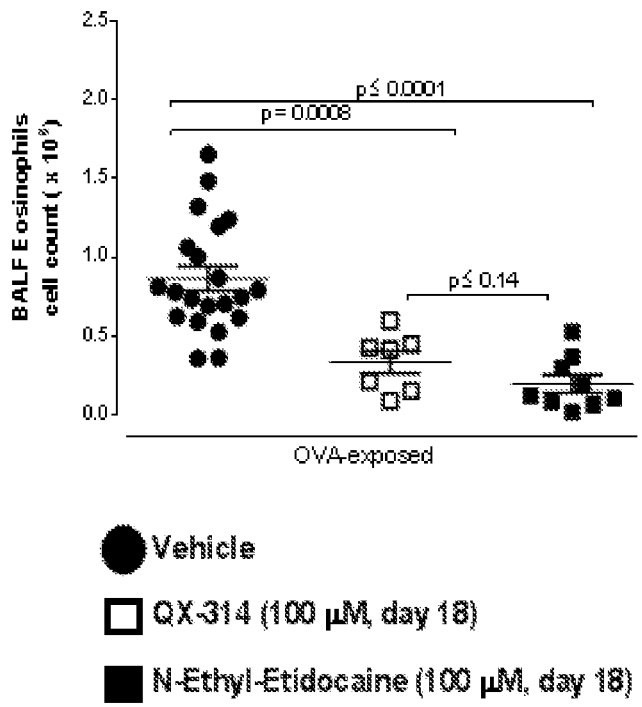
Figure 5D:
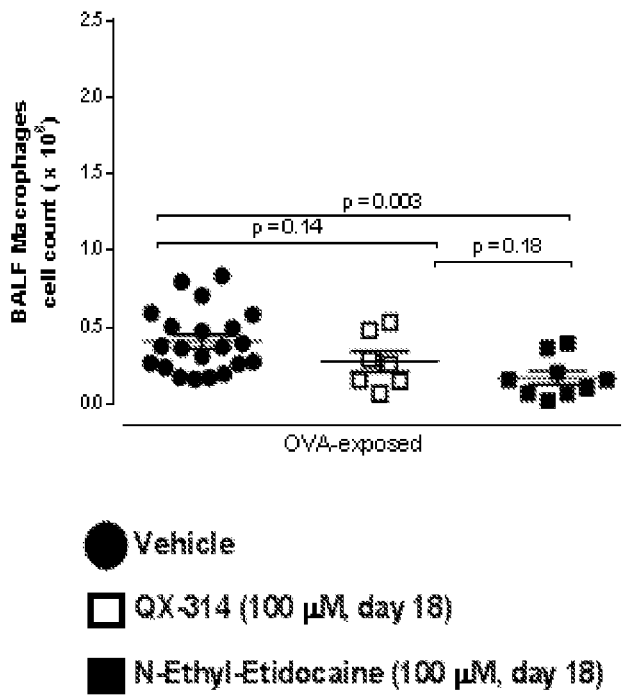
Figure 5E:
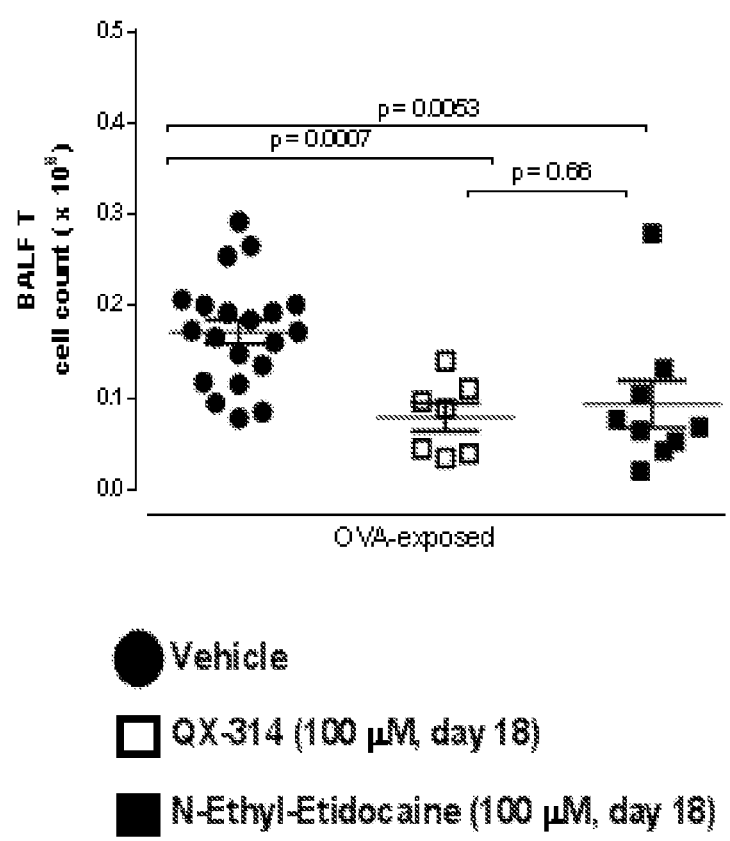

Example 16. Compound 21 was as Effective as QX-314 in Blocking Paw Incision-Induced Thermal Hyperalgesia The effects of N-ethyl etidocaine ("NEE", Compound 21) compared to QX-314 were tested in a mouse and rat models of thermal hyperalgesia. Inflammation-related hyperalgesia evoked by intraplantar injection of CFA in mice is reversed by Compound 21 (NEE) or by QX-314 (FIGS. 2A-2D). In rats (FIG. 3A), no differences in thermal nociceptive threshold were observed between the contralateral (untreated) paw and the hind paw that received an acute intraplantar injection (50 μl) of saline, QX-314 (0.5%) or N-ethyl etidocaine (Compound 21) (0.5%). One week later the rats underwent surgical incision to their left hindpaw. One hour later the rats received acute intradermal injections of compound 21 or QX-314 directly into the surgical wound. When compared to their untreated contralateral paw, the animals that received the saline treatment showed a significant thermal hyperalgesia at 1 and 3 hour post-treatment (FIG. 3B). This effect was absent in animals treated with QX-314 or Compound 21, suggesting that Compound 21 is as effective as QX-314 in decreasing pain sensitivity in conditions of thermal hyperalgesia.

Example 17. Compounds 3, 6, and 21 have Effects on Thermal Nociceptive Response Latency when Injected Alone Some data in the literature suggests that QX-314, when injected perineurally, can induce neurotoxicity 8 weeks post-treatment. To evaluate if such toxicity occurred with NEE (Compound 21), mice were injected with a combination of $CFA_+NEE$ (1%) 8 weeks prior to DRG extraction. DRGs extracted from these mice were stained for ATF3, a transcription factor specifically increased in injured neurons. No ATF3 expression was observed in the $CFA_+NEE$ (1%) treated mice (FIG. 4B and FIG. 4C). To confirm the validity of the staining, a DRG slice from an ATF3-GFP reporter mice that underwent a sciatic nerve injury was labeled in parallel and co-localization of the ATF3 antibody (dark shading) was observed with the ATF3 reporter staining (light shading) (FIG. 4A).

It is known that QX-314 reverses allergic airway inflammation by interrupting the interplay between the pain neuron and the immune system. To determine if NEE (Compound 21) works by the same mechanism, the effect of NEE (Compound 21) on airway inflammation was then assessed. Aerosolized NEE (Compound 21) (100 uM, 6%, 20 min, day 18) blocked bronchoalveolar lavage fluid immune cell influx (day 21), specifically CD45+ cells, including eosinophils, macrophages, and T cells, in a murine model of allergic airway inflammation induced by Ovalbumin (FIGS. 5A-5E).

Of the five new compounds that show an improved in vitro NaV1.7 use-dependent block over QX-314, ACS-3B (Compound 3) and N-ethyl-etidocaine (Compound 21) showed potent blockade of CFA-induced thermal hyperalgesia without long lasting analgesia in naïve animals. Further, N-ethyl-etidocaine (Compound 21) potently reversed lung allergic airway inflammation.

Other Embodiments

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A quaternary amine compound represented by formula (I)

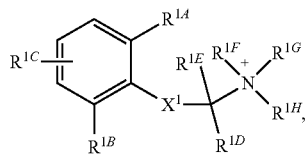

wherein
$R^{1F}$ and $R^{1G}$ together complete a 5- or 6-membered heterocyclic ring;
each of $R^{1A}$ and $R^{1B}$ is methyl;
$R^{1C}$ is selected from H, halogen, $C_{1-4}$ alkyl, $C_{2-4}$ alkenyl, $C_{2-4}$ alkynyl, $OR^{1J}$, $NR^{1J}R^{1K}$, $NR^{1L}C(O)R^{1M}$, $S(O)R^{1N}$, $SO_2R^{1O}$, $R^{1P}$, $SO_2NR^{1Q}R^{1R}$, $so_3R^{1S}$, $CO_2R^{1T}$, $C(O)R^{1U}$, and $C(O)NR^{1V}R^{1W}$; and each of $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, and $R^{1W}$ is, independently, selected from H, $C_{1-4}$ alkyl, $C_{2-4}$ alkenyl, $C_{2-4}$ alkynyl, and $C_{2-4}$ heteroalkyl;
$X^1$ is —$NR^{1Z}C(O)$—; and $R^{1Z}$ is H;
$R^{1D}$ is ethyl;
$R^{1E}$ is H or $C_{1-4}$ alkyl optionally substituted with halogen, $C_{3-8}$ cycloalkyl, aryl, or heteroaryl;
$R^{1H}$ is $C_{1-4}$ alkyl optionally substituted with halogen, $C_{3-8}$ cycloalkyl, aryl, or heteroaryl, or salt thereof.

2. The compound of claim 1, wherein said compound is (Compound 6)

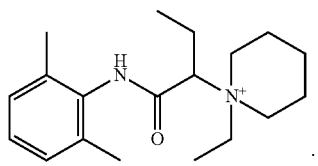

3. The compound of claim 1, wherein said compound is (Compound 3)

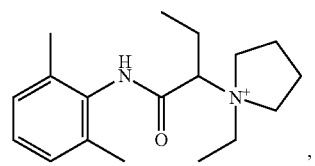

4. A composition comprising the quaternary amine compound of claim 1 and a pharmaceutically acceptable excipient.

5. The composition of claim 4, wherein said composition is formulated for oral, intravenous, intramuscular, rectal, cutaneous, subcutaneous, topical, transdermal, sublingual, nasal, vaginal, intrathecal, epidural, or ocular administration, or wherein said compound is formulated for administration by inhalation.

6. A method for treating pain, itch, or a neurogenic inflammatory disorder in a patient, wherein said neurogenic inflammatory disorder is selected from the group consisting of allergic inflammation, asthma, chronic cough conjunctivitis, rhinitis, psoriasis, inflammatory bowel disease, interstitial cystitis, and atopic dermatitis, said method comprising administering to said patient a composition comprising the quaternary amine compound of claim 1, wherein said compound inhibits one or more voltage-gated ion channels present in nociceptors and/or pruriceptors when applied to the internal face of said channels but does not substantially inhibit said channels when applied to the external face of said channels, and wherein said compound is capable of (i) entering nociceptors or pruriceptors through a channel-forming receptor when said receptor is activated and (ii) inhibiting said one or more voltage-gated ion channels present in said nociceptors and/or pruriceptors.

7. The method of claim 6, wherein said pain is selected from the group consisting of neuropathic pain, inflammatory pain, nociceptive pain, pain due to infections, and procedural pain.

8. The method of claim 6, wherein said quaternary amine compound is:

(Compound 6)

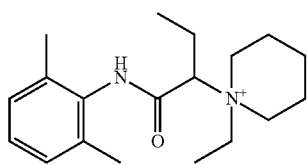

9. The compound of claim 1 wherein $R^{1C}$ is hydrogen.
10. The compound of claim 1 wherein $R^{1E}$ is hydrogen.
11. The compound of claim 1 wherein $R^{1H}$ is $C_{1-4}$ alkyl.
12. The composition of claim 4 wherein said composition is formulated for administration by inhalation.
13. The composition of claim 4 wherein said composition is formulated for topical administration.
14. A composition comprising the quaternary amine compound of claim 2 and a pharmaceutically acceptable excipient.
15. A method for treating pain, itch, or a neurogenic inflammatory disorder in a patient comprising administering to said patient a composition comprising the quaternary amine compound of claim 1.
16. A method for treating cough in a patient comprising administering to said patient a composition comprising the quaternary amine compound of claim 1.
17. A method for treating pain, itch, or a neurogenic inflammatory disorder in a patient comprising administering to said patient a composition comprising the quaternary amine compound of claim 2.
18. A method for treating cough in a patient comprising administering to said patient a composition comprising the quaternary amine compound of claim 2.

* * * * *